United States Patent [19]
Poole et al.

[11] Patent Number: 6,132,976
[45] Date of Patent: Oct. 17, 2000

[54] IMMUNOASSAYS FOR THE MEASUREMENT OF COLLAGEN DENATURATION AND CLEAVAGE IN CARTILAGE

[75] Inventors: Anthony Robin Poole, Baie d'Urfé, Canada; Anthony Peter Hollander, Greystones, United Kingdom; R. Clark Billinghurst, Fort Collins, Colo.

[73] Assignee: Shriners Hospitals for Children, Tampa, Fla.

[21] Appl. No.: 09/010,999

[22] Filed: Jan. 22, 1998

Related U.S. Application Data

[63] Continuation-in-part of application No. 08/448,501, Jul. 17, 1995, abandoned, which is a continuation of application No. 07/984,123, Dec. 4, 1992, abandoned.

[51] Int. Cl.$^7$ .................................................. G01N 33/53
[52] U.S. Cl. ........................... 435/7.1; 435/7.9; 435/792; 435/23; 435/328; 435/331; 435/975; 436/518; 424/1.49; 424/9.3; 424/9.34; 530/326; 530/327; 530/328; 530/388.1; 530/388.85; 530/391.1
[58] Field of Search .......................... 435/7.1, 7.9, 7.92, 435/23, 328, 331, 975; 436/518; 424/1.49, 9.3, 9.34; 530/326, 327, 328, 388.1, 388.85, 391.1

[56] References Cited

U.S. PATENT DOCUMENTS

| | | | |
|---|---|---|---|
| 3,949,073 | 4/1976 | Daniels et al. | 424/177 |
| 4,658,022 | 4/1987 | Knowles et al. | 530/402 |
| 4,973,666 | 11/1990 | Eyre | 530/323 |
| 5,128,360 | 7/1992 | Cerami et al. | 514/400 |
| 5,140,103 | 8/1992 | Eyre | 530/327 |
| 5,641,837 | 6/1997 | Eyre | 435/7.1 |

FOREIGN PATENT DOCUMENTS

| | | |
|---|---|---|
| 2 031 265 | 2/1991 | Canada. |
| 0 505 210 | 9/1992 | European Pat. Off.. |
| WO 89/04491 | 5/1989 | WIPO. |
| WO 91/08478 | 6/1991 | WIPO. |
| WO 94/18563 | 8/1994 | WIPO. |

OTHER PUBLICATIONS

Morgan et al., Identification of an Immunodominant B–cell Epitope in Bovine Type II Collagen and The Production of Antibodies to Type II Collagen By Immunization with A Synthetic Peptide Representing This Epitope, Immunology, 77:609–616 (1992).

Mort et al., "Direct Evidence For Active Metalloproteinases Mediating Matrix Degradation in Interleukin 1–Stimulated Human Articular Cartilage", Matrix, 13(2):95–102 (1993).

Morris et al., "Type XI Collagen Is A Heterotrimer With The Composition (1α, 2α, 3α) Retaining Non–Triple–Helical Domains", The Journal of Biological Chemistry, 262(23):11345–11350 (1987).

Dodge et al., "Immunohistochemical Detection And Immunochemical Analysis of Type II Collagen Degradation In Human Normal, Rheumatoid, And Osteoarthritic Articular Cartilages and In Explants of Bovine Articular Cartilage Cultured With Interleukin 1", J. Clin. Invest., 83(2):647–661 (1989).

Eyre et al., "All Three Chains of 1α2α3α Collagen From Hyaline Cartilage Resist Human Collagenase", Biochemical And Biophysical Research Communication, 118(3):724–729 (1984).

Nimni, "Collagen:Structure,Function, and Metabolism in Normal And Fibrotic Tissues", Seminars in Arthritis and Rheumatism, 13(1):1–85 (1993).

Hanson et al. "A Specific Immunoassay for Monitoring Human Bone . . . ," Journal of Bone and Mineral Research, 7(11):1251–1258 (1992).

Timpl "Immunology of The Collagens", in Extracellular Matrix Biochemistry (1984) pp 159–190.

Hopp et al. "Prediction of Protein Antigenic Determinants From Amino Acids Sequences," Proc. Nat. Acad. Sci. USA, 78(6):3824–3828 (1981).

Jissen "Practice and Theory of Enzyme Immunoassays in Laboratory Techniques in Biochemistry and Molecular Biology," 15:117–121 (1985).

Wu et al. "Identification of Hydroxypyridinium Cross–Linking Sites in Type II Collagen of Bovine Articular Cartilage", Biochemistry 23:1850–1857 (1984).

Kielty, et al. "Collagen: The Collagen Family: Structure, Assembly, and Organization in the Extracellular Matrix", in Connective Tissue and Its Heritable Disorders, pp 103–147 (1993).

(List continued on next page.)

*Primary Examiner*—Jeffrey Stucker
*Attorney, Agent, or Firm*—Foley & Lardner

[57] ABSTRACT

The present invention relates to a method for detecting cartilage degradation in a biological sample by identifying the presence of unwound type II collagen in the biological sample, said method comprising:

contacting the biological sample with a monoclonal antibody which does not bind to native helical collagen but which does bind to an epitope on unwound type II collagen chains or fragments thereof, wherein said epitope has the following sequence (SEQ ID NO: 4):

A-P(OH)-G-E-D-G-R-P(OH)-G-P-P(OH)-G-P; and detecting the presence of the bound monoclonal antibody. The present invention also relates to a method for detecting collagenase induced cartilage degradation in a biological sample by identifying the presence of an epitope on type II collagen which only becomes detectable following cleavage of said collagen by collagenase, said method comprising:

contacting the biological sample with a monoclonal antibody which binds to said epitope on type II collagen chains or fragments thereof containing said epitope; and detecting the presence of said monoclonal antibody bound to the type II collagen and fragments.

37 Claims, 25 Drawing Sheets

OTHER PUBLICATIONS

Antoniou, et al., "The Human Lumbar Endplate, Evidence of Changes in Biosynthesis and Denaturation of the Extracellular Matrix With Growth, Maturation, Aging, and Degeneration", Spine 21(10):1153–1161 (1996).

Alini, et al., The Extracellular Matrix of Cartilage in the Growth Plate Before and During Calcification: Changes in Composition and Degradation of Type II Collagen, Calcif Tissue Int. 50:327–335 (1992).

Dodge, et al., "The Degradation of Type II Collagen in Rheumatoid Arthritis: An Immunoelectron Microscopic Study", Matrix 11:330–338 (1992).

Antoniou, et al., "The Human Lumbar Intervertebral Disc: Evidence for Changes in the Biosynthesis and Denaturation of the Extracellular Matrix with Growth, Maturation, Ageing, and Degeneration", J. Clin. Invest. 98(4):996–1003 (1996).

Billinghurst, et al., "Enhanced Cleavage Type II Collagen by Collagenases in Osteoarthritic Articular Cartilage", J. Clin. Invest. 99(7):1534–1545 (1997).

Hollander, et al., "Damage to Type II Collagen In Aging and Osteoarthritis Starts at the Articular Surface, Originates Around Chondrocytes, and Extends into the Cartilage with Progressive Degeneration", J. Clin. Invest. 96:2859–2869 (1995).

"Practice and Theory of Enzyme Immunoassays", Ch. 7, pp 116–121, Elsever Science Publishers B.V. (Biomedical Division).

Honor B. Fell, et al., "The Capacity of Pig Articular Cartilage in Organ Culture to Regenerate . . . to Pig Erythrocytes", Calcif. Tiss. Res., No. 20:3–21 (1976).

Paul G. Scott, et al., "Semiquantitative Determination of Cyanogen Bromide Peptides of Collagen in SDS–Polyacrylamide Gels", Analytical Biochemistry, No. 70:251–257 (1976).

S. Fazekas de St. Groth, et al., "Production of Monoclonal Antibodies:Strategy and Tactics", Journal of Immunological Methods, No. 35:1–21 (1980).

Ervin H. Epstein, Jr., "[$\alpha 1(III)$]$_3$ Human Skin Collagen", The Journal of Biological Chemistry, vol. 249, No. 10:3225–3231 (1974).

Thorsten Kirsch, et al., "Isolation of Human Type X Collagen and Immunolocalization in Fetal Human Cartilage", Eur. J. Biochem. No. 196:575–580 (1991).

Subhash Pal, et al., "Structural Changes During Development in Bovine Fetal Epiphyseal Cartilage", Coll. Res. vol. 1:151–176 (1981).

Geihan Rizkalla, et al., "Studies of the Articular Cartilage Proteoglycan Aggrecan in Health and Osteoarthritis, Evidence for Molecular Heterogeneity and Extensive Molecular Changes in Disease", J. Clin. Invest., vol. 90:2268–2277 (1992).

Henry J. Mankin. et al., "Biochemical and Metabolic Abnormalities in Articular Cartilage from Osteo–Arthritic Human Hips", vol. 53A:523–537 (1971).

A. Robin Poole, et al., "Cellular Biology of Cartilage Degradation", Mechanisms and Models in Rheumatoid Arthritis. B. Henderson, J. Edwards and R. Pettipher, editors. Academic Press, London.

G.E. Kempson, et al., "The Tensile Properties of the Cartilage of Human Femoral Condyles Related to the Content of Collagen and Glycosaminoglycans", Biochimica et Biophysica Acta, vol. 297:456–472 (1973).

Shaw Akizuki, et al., "Tensile Properties of Human Knee Joint Cartilage: I. Influence of Ionic Conditions, Weight Bearing, and Fibrillation on the Tensile Modulus", Journal of Orthopaedic Research vol. 4:379–392 (1986).

Van C. Mow, et al., "Structure–Function Relationships of Articular Cartilage and the Effects of Joint Instability and Trauma on Cartilage Function", Cartilage Changes in Osteoarthritis, pp. 22–42 (1990).

A. Robin Poole, "Cartilage in Health and Disease", Arthritis and Allied Conditions, pp 279–333 (1993).

Geoffrey E. Kempson, "The Mechanical Properties of Articular Cartilage", The Joints and Synovial Fluid, vol. 2:177–238 (1980).

Mary Beth Schmidt, et al., "Effects of Proteoglycan Extraction on the Tensile Behavior of Articular Cartilage", Journal of Orthopaedic Research, vol. 8:353–363 (1990).

Geoffrey E. Kempson, "Age–Related Changes in the Tensile Properties of Human Articular Cartilage: A Comparative Study Between the Femoral Head of the Hip Joint and the Talus of the Ankle Joint", Biochimica et Biophysica Acta, vol. 1075:223–230 (1991).

M. Venn and A. Maroudas, "Chemical Composition and Swelling of Normal and Osteoarthritic Femoral Head Cartilage", Annals of the Rheumatic Diseases, vol. 36:121–129 (1977).

Masaaki Mohtai, et al., "Expression of 92–kD Type IV Collagenase/Gelatinase (Gelatinase B) in Osteoarthritic Cartilage and Its Induction in Normal Human Articular Cartilage by Interleukin 1", J. Clin. Invest., vol. 92:179–185 (1993).

A. Robin Poole, et al., "Methods for Evaluating Mechanisms of Cartilage Breakdown", Joint Cartilage Degradation, Basic and Clinical Aspects, pp 225–260 (1993).

David Eyre, et al., "Type XI or $1\alpha 2\alpha 3\alpha$ Collagen", Structure and Function of Collagen Types, pp. 262–281 (1987).

David R. Eyre, et al., "A Growing Family of Collagens in Articular Cartilage: Identification of 5 Genetically Distinct Types", Journal of Rheumatology, (Suplt.) vol. 14:25–27 (1987).

M.D. Humzah, et al., "Human Intervertebral Disc: Structure and Function", The Anatomical Record, vol. 220:337–356 (1988).

J.P. Thompson, et al., "Preliminary Evaluation of a Scheme for Grading the Gross Morphology of the Human Intervertebral Disc", Spine, vol. 15:411–415, No. 5 (1990).

Barrie Vernon–Roberts, "Disc Pathology and Disease States", The Biology of the Intervertebral Disc, vol. 2:73–119 (1988).

Sol Bernick, et al., "Age Changes to the Anulus Fibrosus in Human Intervertebral Discs", Spine, vol. 16:520–524, No. 5: (1991).

Richard H. Pearce, et al., "Degeneration and the Chemical Composition of the Human Lumbar Intervertebral Disc", Journal of Orthopaedic Research, vol. 5:198–205 (1987).

Richard H. Pearce, et al., "Magnetic Resonance Imaging Reflects the Chemical Changes of Aging Degeneration in the Human Intervertebral Disk", Journal of Rheumatology, (Suplt 27) vol. 18:42–43 (1991).

David R. Eyre, et al., "Quantitative Analysis of Types I and II Collagens in Human Intervertebral Discs at Various Ages", Biochimica et Biophysica Acta, vol. 492:29–42 (1977).

S. Roberts et al., "Collagen Types Around the Cells of the Intervertebral Disc and Cartilage End Plate: An Immunolocalization Study", 1991 Volvo Award in Basic Sciences, Spine, vol. 16:1030–1038, No. 9 (1991).

David R. Eyre, "Collagens of the Disc", The Biology of the Intervertebral Disc, vol. 1:171–188 (1988).

S. Roberts et al., "Biochemical and Structural Properties of the Cartilage End–Plate and its Relation to the Intervertebral Disc", Spine, vol. 14:166–174, No. 2 (1989).

Cahir A. McDevitt, "Proteoglycans of the Intervertebral Disc", The Biology of the Intervertebral Disc, vol. 1:151–170 (1988).

Mary C. Burleigh, et al., "A Lysosomal Enzyme That Degrades Native Collagen", Biochem. J. vol. 137:387–398 (1974).

A. P. Hollander, et al., "Human Cartilage is Degraded by Rheumatoid Arthritis Synovial Fluid but Not by Recombinant Cytokines in vitro", Clin. Exp. Immunol. vol. 83:52–57 (1991).

Colin Henderson, "Aminoalkylsilane: An Inexpensive, Simple Preparation for Slide Adhesion", The Journal of Histotechnology, vol. 12: 123–124, No. 2 (1989).

A.R. Poole, et al., "Localization of Proteoglycan Monomer and Link Protein in the Matrix of Bovine Articular Cartilage: An Immunohistochemical Study", The Journal of Histochemistry and Cytochemistry, vol. 28, No. 7:621–635 (1980).

Ference Gallyas, et al., "Cooper–$H_2O_2$ Oxidation Strikingly Improves Silver Intensification of the Nickel–Diaminobenzidine (Ni—DAB) End–Product of the Peroxidase Reaction", The Journal of Histochemistry and Cytochemistry, vol. 36, No. 7:807–810 (1988).

H. Birkedal–Hansen, et al., "Matrix Metalloproteinases: A Review", Critical Reviews in Oral Biology and Medicine, vol. 4, No. 2:197–250 (1993).

Vijay P. Chandnani, et al., "Knee Hyaline Cartilage Evaluated with MR Imaging: A Cadaveric Study Involving Multiple Imaging Sequences and Intraarticular Injection of Gadolinium and Saline Solution", Radiology vol. 178:557–561 (1991).

Manuel Baca, et al., "Antibody Humanization Using Monovalent Phage Display", The Journal of Biological Chemistry, vol. 272, No. 16:10678–10684 (1997).

Anthony P. Hollander, et al., "Enhanced Denaturation of the $\alpha 1(II)$ Chains of Type–II Collagen in Normal Adult Human Intervertebral Discs Compared with Femoral Articular Cartilage", Journal of Orthopaedic Research vol. 14, No. 1:61–66 (1996).

Anthony P. Hollander, et al., "Increased Damage to Type II Collagen in Osteoarthritic Articular Cartilage Detected by a New Immunoassay", J. Clin. Invest. vol. 93:1722–1732 (1994).

"Arthritis & Rheumatism", Abstract Supplement, National Scientific Meeting, American College of Rheumatology, vol. 40, No. 9, pp. S247 (1997).

James A. Fagin, et al., "High Prevalence of Mutations of the p53 Gene in Poorly Differentiated Human Thyroid Carcinomas", J. Clin. Invest. vol. 91:179–184 (1993).

| | | |
|---|---|---|
| N-1- | MIRLGAPQSL VLLTLLVAAV LRCQ | -SIGNAL P. |
| | GQDVRQ PGPKGQKGEP GDIKDIVGPK | -N-PRO-P |
| 51- | GPPGPQGPAG EQGPRGDRGD KGEKGAPGPR GRDGEPGTLG NPGPPGPPGP | |
| 101- | PGPPGLGGNF AA     C.LINK   STR   PEP   STR | |
| |                   QMAGGFDE KAGGA↓QL↓GV↓M Q | -N-TELO-P. |
| |                                       GPMGPMGPR GPPGPAGAPG | -TRIP. HEL. |
| 151- | PQGFQGNPGE PGEPGVSGPM GPRGPPGPPG KPGDDGEAGK PGKAGERGPP | CNBr:1/2/3 |
| 201- | GPQGARGFPG TPGLPGVKGH RGYPGLDGAK GEAGAPGVKG ESGSPGENGS | 4/6/12 |
| 251- | PGPM | |
| |      GPRGLP GERGRTGPAG AAGARGNDGQ PGPAGPPGPV GPAGGPGFPG | -TRIP. HEL. |
| 301- | APGAKGEAGP TGARGPEGAQ GPRGEPGTPG SPGPAGASGN PGTDGIPGAK | CNBr:11 |
| 351- | GSAGAPGIAG APGFPGPRGP PDPQGATGPL GPKGQTGKPG IAGFKGEQGP | |
| 401- | KGEPGPAGPQ GAPGPAGEEG KRGARGEPGG VGPIGPPGER GAPGNRGFPG | |
| 451- | QDGLAGPKGA PGERGPSGLA GPKGANGDPG RPGEPGLPGA RGLTGRPGDA | |
| 501- | GPQGKVGPSG APGEDGRPGP PGPQGARGQP GVM | |
| |                 CB11B | |
| |                                        GFPGPKG ANGEPGKAGE | -TRIP. HEL. |
| 551- | KGLPGAPGLR GLPGKDGETG AEGPPGPAGP AGERGEQGAP GPSGFQGLPG | CNBr:8 |
| 601- | PPGPPGEGGK PGDQGVPGEA GAPGLVGPRG ERGFPGERGS PGAQGLQGPR | |
| 651- | GLPGTPGTDG PKGASGPAGP PGAQGPPGLQ GM | |
| |                                PGERGAAG IAGPKGDRGD | -TRIP. HEL. |
| 701- | VGEKGPEGAP GKDGGRGLTG PIGPPGPAGA NGEKGEVGPP GPAGSAGARG | CNBr:10 |
| 751- | APGERGETGP PGTSGIAGPP GADGQPGAKG EQGEAGQKGD AGAPGPQGPS | |
| 801- | GAPGPQGPTG VTGPKGARGA QGPPGATGFP GAAGRVGPPG SNGNPGPPGP | |
| 851- | PGPSGKDGPK GARGDSGPPG RAGEPGLQGP AGPPGEKGEP GDDGPSGAEG | |
| 901- | PPGPQGLAGQ RGIVGLPGQR GERGFPGLPG PSGEPGQQGA PGASGDRGPP | |
| 951- | GPVGPPGLTG PAGEPGREGS PGADGPPGRD GAAGVKGDRG ETGAVGAPGA | |
| 1001- | PGPPGSPGPA GPTGKQGDRG EAGAQGPM | |
| |                                         GP SGFAGARGIQ GPQGPRGDKG | -TRIP. HEL. |
| 1051- | EAGEPGERGL KGHRGFTGLQ GLPGPPGPSG DQGASGPAGP SGPRGPPGPV | CNBr:5/9/7 |
| 1101- | GPSGKDGAMG IPGPIGPPGP RGRSGETGPA GPPGNPGPPG PPGPP | 14/15 |
| |                                                                 GPGID | -C-TELO-P. |
| 1151- | MSAFAGLGPK EKGPDPLQYM RA | |
| |                             DQAAGGLR QHDAEVDATL KSLNNQIESI | -C-PRO-P. |
| 1201- | RSPEGSRKNP ARTCRDLKLC HPEWKSGDYW IDPNQGCTID AMKVFCHMET | |
| 1251- | GETCVYPNPA NVPKKNWWSS KSKEKKHIWF GETINGGFHF SYGDDNLAPN | |
| 1301- | TANVQMTFLR LLSTEGSQNI TYHCKNCIAY LDEAAGNLKK ALLIQGSNDV | |
| 1351- | EIRAEGNSRF TYTALKDGCT KHTGKWGKTV IEYRSQKTSR LPIIDIAPMD | |
| 1401- | IGGPEQEFGV DIGPVCFL | -C |

| Immunizing peptide: | C G G E G P P(OH) G P Q G | | |
|---|---|---|---|
| | | PRIMARY COLLAGENASE CLEAVAGE SITE → | |
| TYPE II α1 | G A E G P P(OH) G P Q G$_{775}$ | | L A$_{776}$ G Q R G I V G |
| TYPE I α1 | G A P G T P G P Q G | | I A G Q R G V V G |
| TYPE I α2 | G P P G T P G P Q G | | L L G A P G I L G |
| TYPE III α1 | G P P G A P G P L G | | I A G I T G A R G |

FIG. 15

COL2-3/4C long mono in serum and urine samples

* Mann Whitney test

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 1418 amino acids
      (B) TYPE: amino acid
      (C) STRANDEDNESS:
      (D) TOPOLOGY: linear (ii) MOLECULE TYPE: protein (vi) ORIGINAL SOURCE:
      (A) ORGANISM: Human Type II Collagen (xi) SEQUENCE DESCRIPTION: SEQ ID NO:1:

```
Met Ile Arg Leu Gly Ala Pro Gln Ser Leu Val Leu Leu Thr Leu Leu
1               5                   10                  15

Val Ala Ala Val Leu Arg Cys Gln Gly Gln Asp Val Arg Gln Pro Gly
            20                  25                  30

Pro Lys Gly Gln Lys Gly Glu Pro Gly Asp Ile Lys Asp Ile Val Gly
        35                  40                  45

Pro Lys Gly Pro Pro Gly Pro Gln Gly Pro Ala Gly Glu Gln Gly Pro
    50                  55                  60

Arg Gly Asp Arg Gly Asp Lys Gly Glu Lys Gly Ala Pro Gly Pro Arg
65                  70                  75                  80

Gly Arg Asp Gly Glu Pro Gly Thr Leu Gly Asn Pro Gly Pro Pro Gly
                85                  90                  95

Pro Pro Gly Pro Pro Gly Pro Pro Gly Leu Gly Gly Asn Phe Ala Ala
            100                 105                 110

Gln Met Ala Gly Gly Phe Asp Glu Lys Ala Gly Gly Ala Gln Leu Gly
        115                 120                 125

Val Met Gln Gly Pro Met Gly Pro Met Gly Pro Arg Gly Pro Pro Gly
    130                 135                 140

Pro Ala Gly Ala Pro Gly Pro Gln Gly Phe Gln Gly Asn Pro Gly Glu
145                 150                 155                 160

Pro Gly Glu Pro Gly Val Ser Gly Pro Met Gly Pro Arg Gly Pro Pro
                165                 170                 175

Gly Pro Pro Gly Lys Pro Gly Asp Asp Gly Glu Ala Gly Lys Pro Gly
```

-continued

```
            180                 185                 190
Lys Ala Gly Glu Arg Gly Pro Pro Gly Pro Gln Gly Ala Arg Gly Phe
        195                 200                 205
Pro Gly Thr Pro Gly Leu Pro Gly Val Lys Gly His Arg Gly Tyr Pro
        210                 215                 220
Gly Leu Asp Gly Ala Lys Gly Glu Ala Gly Ala Pro Gly Val Lys Gly
225                 230                 235                 240
Glu Ser Gly Ser Pro Gly Glu Asn Gly Ser Pro Gly Pro Met Gly Pro
                245                 250                 255
Arg Gly Leu Pro Gly Glu Arg Gly Arg Thr Gly Pro Ala Gly Ala Ala
            260                 265                 270
Gly Ala Arg Gly Asn Asp Gly Gln Pro Gly Pro Ala Gly Pro Pro Gly
        275                 280                 285
Pro Val Gly Pro Ala Gly Gly Pro Gly Phe Pro Gly Ala Pro Gly Ala
        290                 295                 300
Lys Gly Glu Ala Gly Pro Thr Gly Ala Arg Gly Pro Glu Gly Ala Gln
305                 310                 315                 320
Gly Pro Arg Gly Glu Pro Gly Thr Pro Gly Ser Pro Gly Pro Ala Gly
                325                 330                 335
Ala Ser Gly Asn Pro Gly Thr Asp Gly Ile Pro Gly Ala Lys Gly Ser
            340                 345                 350
Ala Gly Ala Pro Gly Ile Ala Gly Ala Pro Gly Phe Pro Gly Pro Arg
        355                 360                 365
Gly Pro Pro Asp Pro Gln Gly Ala Thr Gly Pro Leu Gly Pro Lys Gly
        370                 375                 380
Gln Thr Gly Lys Pro Gly Ile Ala Gly Phe Lys Gly Glu Gln Gly Pro
385                 390                 395                 400
Lys Gly Glu Pro Gly Pro Ala Gly Pro Gln Gly Ala Pro Gly Pro Ala
                405                 410                 415
Gly Glu Glu Gly Lys Arg Gly Ala Arg Gly Glu Pro Gly Gly Val Gly
            420                 425                 430
Pro Ile Gly Pro Pro Gly Glu Arg Gly Ala Pro Gly Asn Arg Gly Phe
        435                 440                 445
Pro Gly Gln Asp Gly Leu Ala Gly Pro Lys Gly Ala Pro Gly Glu Arg
        450                 455                 460
Gly Pro Ser Gly Leu Ala Gly Pro Lys Gly Ala Asn Gly Asp Pro Gly
465                 470                 475                 480
Arg Pro Gly Glu Pro Gly Leu Pro Gly Ala Arg Gly Leu Thr Gly Arg
                485                 490                 495
Pro Gly Asp Ala Gly Pro Gln Gly Lys Val Gly Pro Ser Gly Ala Pro
            500                 505                 510
Gly Glu Asp Gly Arg Pro Gly Pro Pro Gly Pro Gln Gly Ala Arg Gly
        515                 520                 525
Gln Pro Gly Val Met Gly Phe Pro Gly Pro Lys Gly Ala Asn Gly Glu
        530                 535                 540
Pro Gly Lys Ala Gly Glu Lys Gly Leu Pro Gly Ala Pro Gly Leu Arg
545                 550                 555                 560
Gly Leu Pro Gly Lys Asp Gly Glu Thr Gly Ala Glu Gly Pro Pro Gly
                565                 570                 575
Pro Ala Gly Pro Ala Gly Glu Arg Gly Glu Gln Gly Ala Pro Gly Pro
            580                 585                 590
Ser Gly Phe Gln Gly Leu Pro Gly Pro Pro Gly Pro Pro Gly Glu Gly
        595                 600                 605
```

-continued

```
Gly Lys Pro Gly Asp Gln Gly Val Pro Gly Glu Ala Gly Ala Pro Gly
    610                 615                 620
Leu Val Gly Pro Arg Gly Glu Arg Gly Phe Pro Gly Glu Arg Gly Ser
625                 630                 635                 640
Pro Gly Ala Gln Gly Leu Gln Gly Pro Arg Gly Leu Pro Gly Thr Pro
                645                 650                 655
Gly Thr Asp Gly Pro Lys Gly Ala Ser Gly Pro Ala Gly Pro Pro Gly
                660                 665                 670
Ala Gln Gly Pro Pro Gly Leu Gln Gly Met Pro Gly Glu Arg Gly Ala
            675                 680                 685
Ala Gly Ile Ala Gly Pro Lys Gly Asp Arg Gly Asp Val Gly Glu Lys
            690                 695                 700
Gly Pro Glu Gly Ala Pro Gly Lys Asp Gly Gly Arg Gly Leu Thr Gly
705                 710                 715                 720
Pro Ile Gly Pro Pro Gly Pro Ala Gly Ala Asn Gly Glu Lys Gly Glu
                725                 730                 735
Val Gly Pro Pro Gly Pro Ala Gly Ser Ala Gly Ala Arg Gly Ala Pro
                740                 745                 750
Gly Glu Arg Gly Glu Thr Gly Pro Pro Gly Thr Ser Gly Ile Ala Gly
            755                 760                 765
Pro Pro Gly Ala Asp Gly Gln Pro Gly Ala Lys Gly Glu Gln Gly Glu
770                 775                 780
Ala Gly Gln Lys Gly Asp Ala Gly Ala Pro Gly Pro Gln Gly Pro Ser
785                 790                 795                 800
Gly Ala Pro Gly Pro Gln Gly Pro Thr Gly Val Thr Gly Pro Lys Gly
                805                 810                 815
Ala Arg Gly Ala Gln Gly Pro Pro Gly Ala Thr Gly Phe Pro Gly Ala
            820                 825                 830
Ala Gly Arg Val Gly Pro Pro Gly Ser Asn Gly Asn Pro Gly Pro Pro
            835                 840                 845
Gly Pro Pro Gly Pro Ser Gly Lys Asp Gly Pro Lys Gly Ala Arg Gly
850                 855                 860
Asp Ser Gly Pro Pro Gly Arg Ala Gly Glu Pro Gly Leu Gln Gly Pro
865                 870                 875                 880
Ala Gly Pro Pro Gly Glu Lys Gly Glu Pro Gly Asp Asp Gly Pro Ser
                885                 890                 895
Gly Ala Glu Gly Pro Pro Gly Pro Gln Gly Leu Ala Gly Gln Arg Gly
            900                 905                 910
Ile Val Gly Leu Pro Gly Gln Arg Gly Glu Arg Gly Phe Pro Gly Leu
            915                 920                 925
Pro Gly Pro Ser Gly Glu Pro Gly Gln Gln Gly Ala Pro Gly Ala Ser
            930                 935                 940
Gly Asp Arg Gly Pro Pro Gly Pro Val Gly Pro Pro Gly Leu Thr Gly
945                 950                 955                 960
Pro Ala Gly Glu Pro Gly Arg Glu Gly Ser Pro Gly Ala Asp Gly Pro
                965                 970                 975
Pro Gly Arg Asp Gly Ala Ala Gly Val Lys Gly Asp Arg Gly Glu Thr
            980                 985                 990
Gly Ala Val Gly Ala Pro Gly Ala Pro Gly Pro Pro Gly Ser Pro Gly
            995                 1000                1005
Pro Ala Gly Pro Thr Gly Lys Gln Gly Asp Arg Gly Glu Ala Gly Ala
            1010                1015                1020
```

```
Gln Gly Pro Met Gly Pro Ser Gly Pro Ala Gly Ala Arg Gly Ile Gln
1025                1030                1035                1040

Gly Pro Gln Gly Pro Arg Gly Asp Lys Gly Glu Ala Gly Glu Pro Gly
            1045                1050                1055

Glu Arg Gly Leu Lys Gly His Arg Gly Phe Thr Gly Leu Gln Gly Leu
            1060                1065                1070

Pro Gly Pro Pro Gly Pro Ser Gly Asp Gln Gly Ala Ser Gly Pro Ala
        1075                1080                1085

Gly Pro Ser Gly Pro Arg Gly Pro Pro Gly Pro Val Gly Pro Ser Gly
    1090                1095                1100

Lys Asp Gly Ala Met Gly Ile Pro Gly Pro Ile Gly Pro Pro Gly Pro
1105                1110                1115                1120

Arg Gly Arg Ser Gly Glu Thr Gly Pro Ala Gly Pro Pro Gly Asn Pro
            1125                1130                1135

Gly Pro Pro Gly Pro Pro Gly Pro Pro Gly Pro Gly Ile Asp Met Ser
            1140                1145                1150

Ala Phe Ala Gly Leu Gly Pro Arg Glu Lys Gly Pro Asp Pro Leu Gln
        1155                1160                1165

Tyr Met Arg Ala Asp Gln Ala Ala Gly Gly Leu Arg Gln His Asp Ala
    1170                1175                1180

Glu Val Asp Ala Thr Leu Lys Ser Leu Asn Asn Gln Ile Glu Ser Ile
1185                1190                1195                1200

Arg Ser Pro Glu Gly Ser Arg Lys Asn Pro Ala Arg Thr Cys Arg Asp
            1205                1210                1215

Leu Lys Leu Cys His Pro Glu Trp Lys Ser Gly Asp Tyr Trp Ile Asp
            1220                1225                1230

Pro Asn Gln Gly Cys Thr Leu Asp Ala Met Lys Val Phe Cys Asn Met
        1235                1240                1245

Glu Thr Gly Glu Thr Cys Val Tyr Pro Asn Pro Ala Asn Val Pro Lys
    1250                1255                1260

Lys Asn Trp Trp Ser Ser Lys Ser Lys Glu Lys Lys His Ile Trp Phe
1265                1270                1275                1280

Gly Glu Thr Ile Asn Gly Gly Phe His Phe Ser Tyr Gly Asp Asp Asn
            1285                1290                1295

Leu Ala Pro Asn Thr Ala Asn Val Gln Met Thr Phe Leu Arg Leu Leu
        1300                1305                1310

Ser Thr Glu Gly Ser Gln Asn Ile Thr Tyr His Cys Lys Asn Cys Ile
    1315                1320                1325

Ala Tyr Leu Asp Glu Ala Ala Gly Asn Leu Lys Lys Ala Leu Leu Ile
    1330                1335                1340

Gln Gly Ser Asn Asp Val Glu Ile Arg Ala Glu Gly Asn Ser Arg Phe
1345                1350                1355                1360

Thr Tyr Thr Ala Leu Lys Asp Gly Cys Thr Lys His Thr Gly Lys Trp
            1365                1370                1375

Gly Lys Thr Val Ile Glu Tyr Arg Ser Gln Lys Thr Ser Arg Leu Pro
            1380                1385                1390

Ile Ile Asp Ile Ala Pro Met Asp Ile Gly Gly Pro Glu Gln Glu Phe
        1395                1400                1405

Gly Val Asp Ile Gly Pro Val Cys Phe Leu
    1410                1415

(2) INFORMATION FOR SEQ ID NO:2:

(i) SEQUENCE CHARACTERISTICS:
```

(A) LENGTH: 279 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: CB11 peptide of Tpye II Collagen (xi) SEQUENCE DESCRIPTION: SEQ ID NO:2:

Gly Pro Arg Gly Leu Pro Gly Glu Arg Gly Arg Thr Gly Pro Ala Gly
1               5                   10                  15

Ala Ala Gly Ala Arg Gly Asn Asp Gly Gln Pro Gly Pro Ala Gly Pro
            20                  25                  30

Pro Gly Pro Val Gly Pro Ala Gly Pro Gly Phe Pro Gly Ala Pro
        35                  40                  45

Gly Ala Lys Gly Glu Ala Gly Pro Thr Gly Ala Arg Gly Pro Glu Gly
    50                  55                  60

Ala Gln Gly Pro Arg Gly Glu Pro Gly Thr Pro Gly Ser Pro Gly Pro
65                  70                  75                  80

Ala Gly Ala Ser Gly Asn Pro Gly Thr Asp Gly Ile Pro Gly Ala Lys
                85                  90                  95

Gly Ser Ala Gly Ala Pro Gly Ile Ala Gly Ala Pro Gly Phe Pro Gly
            100                 105                 110

Pro Arg Gly Pro Pro Gly Pro Gln Gly Ala Thr Gly Pro Leu Gly Pro
        115                 120                 125

Lys Gly Gln Thr Gly Lys Pro Gly Ile Ala Gly Phe Lys Gly Glu Gln
    130                 135                 140

Gly Pro Lys Gly Glu Pro Gly Pro Ala Gly Pro Gln Gly Ala Pro Gly
145                 150                 155                 160

Pro Ala Gly Glu Glu Gly Lys Arg Gly Ala Arg Gly Glu Pro Gly Gly
                165                 170                 175

Val Gly Pro Ile Gly Pro Pro Gly Glu Arg Gly Ala Pro Gly Asn Arg
            180                 185                 190

Gly Phe Pro Gly Gln Asp Gly Leu Ala Gly Pro Lys Gly Ala Pro Gly
        195                 200                 205

Glu Arg Gly Pro Ser Gly Leu Ala Gly Pro Lys Gly Ala Asn Gly Asp
    210                 215                 220

Pro Gly Arg Pro Gly Glu Pro Gly Leu Pro Gly Ala Arg Gly Leu Thr
225                 230                 235                 240

Gly Arg Pro Gly Asp Ala Gly Pro Gln Gly Lys Val Gly Pro Ser Gly
                245                 250                 255

Ala Pro Gly Glu Asp Gly Arg Pro Gly Pro Pro Gly Pro Gln Gly Ala
            260                 265                 270

Arg Gly Gln Pro Gly Val Met
        275

(2) INFORMATION FOR SEQ ID NO:3:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: CB11B peptide of Type II Collagen

```
         (ix) FEATURE:
              (A) NAME/KEY: Modified-site
              (B) LOCATION: 10
              (D) OTHER INFORMATION: /product= "Pro(OH)"

(ix) FEATURE:
              (A) NAME/KEY: Modified-site
              (B) LOCATION: 16
              (D) OTHER INFORMATION: /product= "Pro(OH)"

(ix) FEATURE:
              (A) NAME/KEY: Modified-site
              (B) LOCATION: 19
              (D) OTHER INFORMATION: /product= "Pro(OH)"

(xi) SEQUENCE DESCRIPTION: SEQ ID NO:3:

Cys Gly Lys Val Gly Pro Ser Gly Ala Xaa Gly Glu Asp Gly Arg Xaa
1               5                   10                  15

Gly Pro Xaa Gly Pro Gln Tyr
            20

(2) INFORMATION FOR SEQ ID NO:4:

(i) SEQUENCE CHARACTERISTICS:
              (A) LENGTH: 13 amino acids
              (B) TYPE: amino acid
              (C) STRANDEDNESS:
              (D) TOPOLOGY: linear (ii) MOLECULE TYPE: peptide (vi) ORIGINAL SOURCE:
              (A) ORGANISM: CB11B/H peptide of Type II Collegen (ix) FEATURE:
              (A) NAME/KEY: Modified-site
              (B) LOCATION: 2
              (D) OTHER INFORMATION: /product= "Pro(OH)"

(ix) FEATURE:
              (A) NAME/KEY: Modified-site
              (B) LOCATION: 8
              (D) OTHER INFORMATION: /product= "Pro(OH)"

(ix) FEATURE:
              (A) NAME/KEY: Modified-site
              (B) LOCATION: 11
              (D) OTHER INFORMATION: /product= "Pro(OH)"

(xi) SEQUENCE DESCRIPTION: SEQ ID NO:4:

Ala Xaa Gly Glu Asp Gly Arg Xaa Gly Pro Xaa Gly Pro
1               5                   10

(2) INFORMATION FOR SEQ ID NO:5:

(i) SEQUENCE CHARACTERISTICS:
              (A) LENGTH: 4 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:5:

Gly Gln Pro Gly
1

(2) INFORMATION FOR SEQ ID NO:6:

(i) SEQUENCE CHARACTERISTICS:
              (A) LENGTH: 7 amino acids
```

```
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Pro(OH)"

(xi) SEQUENCE DESCRIPTION: SEQ ID NO:6:

Gly Pro Xaa Gly Pro Gln Gly
1               5

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "Pro(OH)"

(xi) SEQUENCE DESCRIPTION: SEQ ID NO:7:

Cys Gly Gly Glu Gly Pro Xaa Gly Pro Gln Gly
1               5                   10

(2) INFORMATION FOR SEQ ID NO:8:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "Pro(OH)"

(xi) SEQUENCE DESCRIPTION: SEQ ID NO:8:

Gly Ala Glu Gly Pro Xaa Gly Pro Gln Gly Leu Ala Gly Gln Arg Gly
1               5                   10                  15

Ile Val Gly (2) INFORMATION FOR SEQ ID NO:9:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Gly Ala Pro Gly Thr Pro Gly Pro Gln Gly Ile Ala Gly Gln Arg Gly
1               5                   10                  15

Val Val Gly
```

(2) INFORMATION FOR SEQ ID NO:10:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

```
Gly Pro Pro Gly Thr Pro Gly Pro Gln Gly Leu Leu Gly Ala Pro Gly
 1               5                  10                  15

Ile Leu Gly
```

(2) INFORMATION FOR SEQ ID NO:11:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Gly Pro Pro Gly Ala Pro Gly Pro Leu Gly Ile Ala Gly Ile Thr Gly
 1               5                  10                  15

Ala Arg Gly
```

(2) INFORMATION FOR SEQ ID NO:12:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "Pro(OH)"

(xi) SEQUENCE DESCRIPTION: SEQ ID NO:12:

```
Cys Gly Gly Glu Gly Pro Xaa Gly Pro Gln Gly Leu
 1               5                  10
```

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "Pro(OH)"

(xi) SEQUENCE DESCRIPTION: SEQ ID NO:13:

```
Cys Gly Gly Glu Gly Pro Xaa Gly Pro Gln Gly Leu Ala
 1               5                  10
```

(2) INFORMATION FOR SEQ ID NO:14:

```
        (i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 7
            (D) OTHER INFORMATION: /product= "Pro(OH)"

(xi) SEQUENCE DESCRIPTION: SEQ ID NO:14:

Cys Gly Gly Glu Gly Pro Xaa Gly Pro Gln
1               5                   10

(2) INFORMATION FOR SEQ ID NO:15:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 7
            (D) OTHER INFORMATION: /product= "Pro(OH)"

(xi) SEQUENCE DESCRIPTION: SEQ ID NO:15:

Cys Gly Gly Glu Gly Pro Xaa Gly Pro
1               5

(2) INFORMATION FOR SEQ ID NO:16:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /product= "Pro(OH)"

(xi) SEQUENCE DESCRIPTION: SEQ ID NO:16:

Cys Gly Pro Xaa Gly Pro Gln Gly
1               5
```

IMMUNOASSAYS FOR THE MEASUREMENT OF COLLAGEN DENATURATION AND CLEAVAGE IN CARTILAGE

This application is a Continuation-in-Part of U.S. Ser. No. 08/448,501, filed Jul. 17, 1995, now abandoned, which is a Continuation-in-Part of U.S. Ser. No. 07/984,123, filed Dec. 4, 1992, now abandoned.

FIELD OF THE INVENTION

The invention relates to a method for evaluating cartilage degradation by determining the level of collagen cleavage products in a biological sample. In a preferred embodiment, the invention relates to an immunoassay for measuring type II collagen cleavage in cartilage.

BACKGROUND OF THE INVENTION

The physiological turnover of articular cartilage represents a fine balance between synthesis and degradation. It is a feature of normal growth and development and maintenance of cartilage in the adult. Net cartilage destruction with ensuing loss of joint function is a feature of the arthritides. An understanding of the factors mediating cartilage breakdown and its control, and the ability to detect and measure destruction, is therefore of great importance, since from this an approach can be made to monitor disease activity at the level of cartilage breakdown, and design therapies for the reduction of pathological cartilage destruction and the enhancement of repair in this tissue. Progress to this goal is dependent on identifying the degradative events occurring in articular cartilage and correlating these with the many degradative agents potentially active in the tissue.

The destruction of articular cartilage is due, in part, to the degradation of the extracellular matrix. Type II collagen constitutes the bulk of the fibrillar backbone of cartilage matrix, just as type I collagen forms the fibrillar organization of the extracellular matrix of most other tissues such as skin, bone, ligaments and tendons. These collagens are composed of a tightly wound triple helix. In articular cartilage, type II collagen fibrils are responsible for the tensile strength whereas the proteoglycans provide the compressive stiffness necessary for normal articulation and function. The precise mechanisms by which these connective tissue components are degraded are not fully understood (11). In mammals, one mechanism involves collagenases, enzymes capable of a site-specific cleavage of helical collagen.

Incapable of maintaining a helical structure at physiological temperatures, collagenase-cleaved fibrillar collagens unwind and become susceptible to further degradation by other proteinases in the extracellular space. In this regard, collagenases can be considered the rate limiting enzymes involved in collagen degradation. There are three types of human collagenase that are known to cleave the human fibrillar type I, and II collagens. They are the matrix metalloproteinases (MMP): MMP-1 (interstitial collagenase or collagenase-1); MMP-8 (neutrophil collagenase or collagenase-2) and MMP-13 (collagenase III). Collagenases cleave type II collagen between residues 775 and 776 to produce the characteristic ¼ and ¾ length α-chain fragments that are identifiable by polyacrylamide gel electrophoresis. Once cleaved by collagenase, the three strands of the collagen molecule begin to unwind and become susceptible to further degradation by the same and other proteinases in the extracellular space. Cleavage results in the release of fragments of type II collagen which can be detected in culture media. In vivo, these fragments are diffused into body fluids. They are present in the synovial fluid from which they may enter the lymphatics and drain eventually into peripheral blood. Fragments may also enter urine following filtration in the kidney.

Detection and measurement of arthritis-related type II collagen derived degradation products poses difficulty for clinicians. Traditional methods for the detection of collagen loss from cartilage have relied on the use of stains such as van Gieson's. The latter was used by Fell and her collaborators (2) to detect collagen loss in cartilage which results in a loss of the normal bright-pink staining. This method, like others of its kind, is, however, of unproven specificity. At the present time, damage to cartilage in joints is recorded by X-ray which reveals a loss of joint space as cartilage is destroyed and lost. This change is a particular feature of osteoarthritis and of rheumatoid arthritis. X-ray does not constitute a particularly sensitive tool for diagnosis of arthritis, as a significant amount of cartilage damage must occur before it becomes detectable by this method. As such, X-ray cannot be used to measure early damage to cartilage. Furthermore, X-ray cannot usually be used in studies of less than one year (rheumatoid arthritis) or two years (osteoarthritis) in duration to monitor the subtle effects of drug treatment on cartilage breakdown. This is a particularly significant problem as recent research indicates that drug treatment of arthritis symptoms (principally pain and inflammation) may actually exacerbate cartilage degradation over time. As such, it has become more important to monitor the direct effects of the disease and of drug treatment on cartilage. This is especially necessary since loss of joint function in arthritis results primarily from skeletal damage, particularity to cartilage.

Attempts have been made to develop methods to detect cartilage breakdown, other than by X-ray. However, initially immunogenic techniques were not promising as, for a long time, collagenous proteins were considered non-immunogenic. Furthermore, monoclonal antibodies against collagens often are only capable of binding a low percentage of antigen, i.e. they demonstrate partial binding (52). Dodge et al (1989) (1) described a polyclonal antibody to an epitope on unwound type II collagen. However, polyclonal antibodies prepared in animals have the disadvantage of having a heterogenous composition and may have a different reactivity from animal to animal.

U.S. Pat. No. 5,140,103 (Eyre, Aug. 18, 1992) and U.S. Pat. No. 5,641,837 (Eyre, Jun. 24, 1997) describe a method of determining collagen degradation by detection of a C-terminal type II collagen telopeptide containing a hydroxylysyl pyridinoline cross-link. However, the telopeptide antigen detected by this assay is not produced by cleavage with collagenase, the enzyme believed to be directly responsible for arthritis-related collagen breakdown as shown recently by Billinghurst et al (49).

Accordingly, a need exists for an assay to detect and measure degradation of type II collagen caused by collagenase so as to provide a mechanism for early detection of arthritis and joint damage and for monitoring disease activity, progression and the efficacy of arthritis treatment. In particular, there is a need for such an assay which can be performed using body fluids such as urine, synovial fluid and serum.

SUMMARY OF THE INVENTION

In accordance with the present invention, there is provided methods for the detection and quantitative determination of cartilage degradation.

A method is provided for detection of cartilage breakdown in a biological sample by identifying the presence of unwound type II collagen. The method comprises contacting the biological sample with a monoclonal antibody which binds to an epitope on unwound type II collagen chains, or fragments thereof, and which does not bind to native helical collagen and detecting the presence of the bound monoclonal antibody.

A method is provided whereby cartilage degradation is quantitatively determined by measurement of the amount of unwound type II collagen present in a biological sample through the binding of unwound collagen with a monoclonal antibody, said method comprising:

contacting the biological sample with a monoclonal antibody which does not bind to native helical collagen but which does bind to an epitope on unwound type II collagen chains or fragments thereof, wherein said epitope has the following sequence (SEQ ID NO: 4):

A-P(OH)-G-E-D-G-R-P(OH)-G-P-P(OH)-G-P; and detecting the presence of the bound monoclonal antibody.

The invention also provides a method for measuring total collagen content in a biological sample. The method comprises treating the biological sample to solubilize and unwind collagen without degrading the epitope recognized by the antibody. The amount of unwound collagen and fragments thereof present in the solubilized biological sample is then measured by contacting the biological sample with a monoclonal antibody which has the ability to bind an epitope on unwound collagen chains or fragments thereof containing the epitope. The monoclonal antibody does not bind to native helical collagen. The amount of unwound collagen and fragments thereof bound to the monoclonal antibody is then determined.

In one aspect, the invention provides a method for the determination of cartilage degradation in a biological sample by quantifying the amount of unwound type II collagen in the biological sample, said method comprising:

(a) contacting the biological sample with a first enzyme which cleaves unwound type II collagen chains in the biological sample into collagen fragments without cleaving an antibody-reactive epitope on said unwound type II collagen chains;

(b) extracting the collagen fragments produced by said enzyme from said biological sample to produce an enzyme extract and remaining biological sample;

(c) treating said remaining biological sample with a second enzyme to solubilize and unwind remaining native collagen contained therein without degrading the epitope to produce a solubilized biological sample;

(d) separately contacting said extract and said solubilized biological sample with a monoclonal antibody which binds an epitope on unwound type II collagen chains or fragments thereof containing said epitope, wherein said monoclonal antibody does not bind to native helical collagen;

(e) determining the amount of unwound type II collagen and fragments thereof in said extract and said solubilized biological sample by separately determining the amount of bound monoclonal antibody; and (f) quantifying the amount of type II collagen that is unwound in said sample by comparing the amount of unwound type II collagen in said extract to the amount of type II collagen in said solubilized biological sample.

In another aspect, the invention provides a method for measuring total type II collagen content in a biological sample, said method comprising:

(a) treating the biological sample to solubilize and unwind collagen contained therein, without degrading an epitope that binds to a monoclonal antibody to produce a solubilized biological sample containing unwound collagen;

(b) measuring the amount of unwound collagen present in said solubilized biological sample by contacting said solubilized biological sample with the monoclonal antibody which binds an epitope on unwound type II collagen chains or fragments thereof containing said epitope, wherein said monoclonal antibody does not bind to native helical collagen; and (c) determining the amount of said unwound collagen and fragments thereof bound to said monoclonal antibody.

The present invention also relates to a monoclonal antibody which has the ability to bind to an epitope on unwound collagen chains or fragments thereof containing this epitope. The monoclonal antibody is also characterized in that it does not bind to native helical collagen. The invention also includes a cell line producing this monoclonal antibody.

Also in accordance with the present invention is a kit for the measurement of cartilage degradation products in a biological sample. The kit comprises a monoclonal antibody which has the ability to bind to an epitope on unwound collagen chains or fragments thereof containing the epitope. The monoclonal antibody is also characterized in that it does not bind to native helical collagen. The kit also comprises a solid support for binding proteins and a labelled antibody to measure the binding of the monoclonal antibody to the unwound collagen. Finally, the kit comprises an enzyme which solubilizes and unwinds native helical type II collagen without degrading the antibody reactive epitope on unwound type II collagen.

The invention also includes an immunogenic synthetic peptide sequence. This sequence is characterized in that it has a sufficient number of residues to allow for sufficient antibody activity when used as an immunogen. It comprises at least a portion of a hydrophilic domain of peptide CB11 of type II collagen α-chains and it does not include hydroxylysine residues.

The invention further relates to an assay for detection of collagenase related cartilage degradation which comprises detection of an epitope on type II collagen adjacent to the collagenase cleavage site. The epitope is detectable only following collagenase cleavage of type II collagen and it is detected using a monoclonal antibody. The assay can be performed on biological samples including serum, synovial fluid and plasma.

The invention further relates to a monoclonal antibody which binds with high specificity to an epitope on type II collagen adjacent to the collagen cleavage site and which is only accessible following collagenase cleavage. The invention also relates to a cell line which produces this monoclonal antibody.

The assays of the present invention have potential for monitoring cartilage collagen degradation in children with impaired growth, in adults with rheumatoid arthritis and osteoarthritis and related arthritides and in patients with osteoporosis. As well, the assays can be used to determine and predict disease activity and the effects of therapy in vivo. The assays of the present invention can also be used to measure collagen degradation in intervertebral discs. Also, they have much potential in studying effects of new drugs on cartilage metabolism in vitro and in experimental arthritis in animals in drug development by pharmaceutical companies.

The present invention will be more readily illustrated by referring to the following description which is not intended to be limiting.

IN THE DRAWINGS

FIG. 1 represents the complete amino acid sequence (SEQ ID NO:1) of type II collagen. The peptide fragments obtained through cyanogen bromide degradation of the triple helical region are identified as CNBr peptides 1–15. Abbreviations are as follows: P., peptide; Trip. Hel., triple helix; C.Link, cross-link; STR, stromelysin cleavage site; PEP, pepsin cleavage site; N-PRO-P, amino propeptide; C-PRO-P, carboxy propeptide; TELO-P, telopeptide.

FIG. 3 represents the amino acid sequences of:

a. synthetic peptide CB11B (SEQ ID NO:3); and b. synthetic peptide CB11/H (SEQ ID NO:4).

The latter represents the epitope in CB11B that is seen by monoclonal antibody COL2-3/4m.

Figure 4:
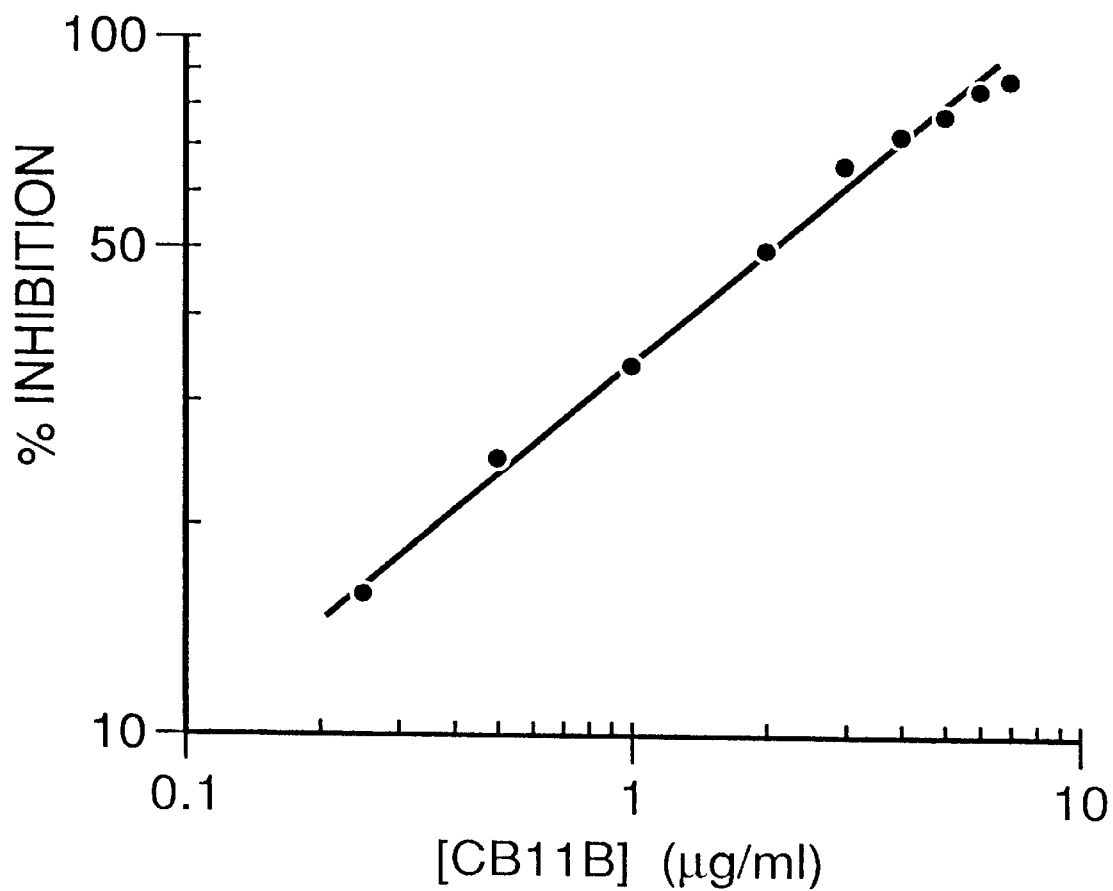

FIG. 4 represents the standard curve of the percentage of inhibition against the concentration of peptide CB11B in an inhibition ELISA.

FIG. 5 represents:

5a. µg/ml, or 5b. molar concentration/response profiles for inhibition in an ELISA assay by heat denatured collagen (HDC) compared with peptide CB11B.

Figure 6:
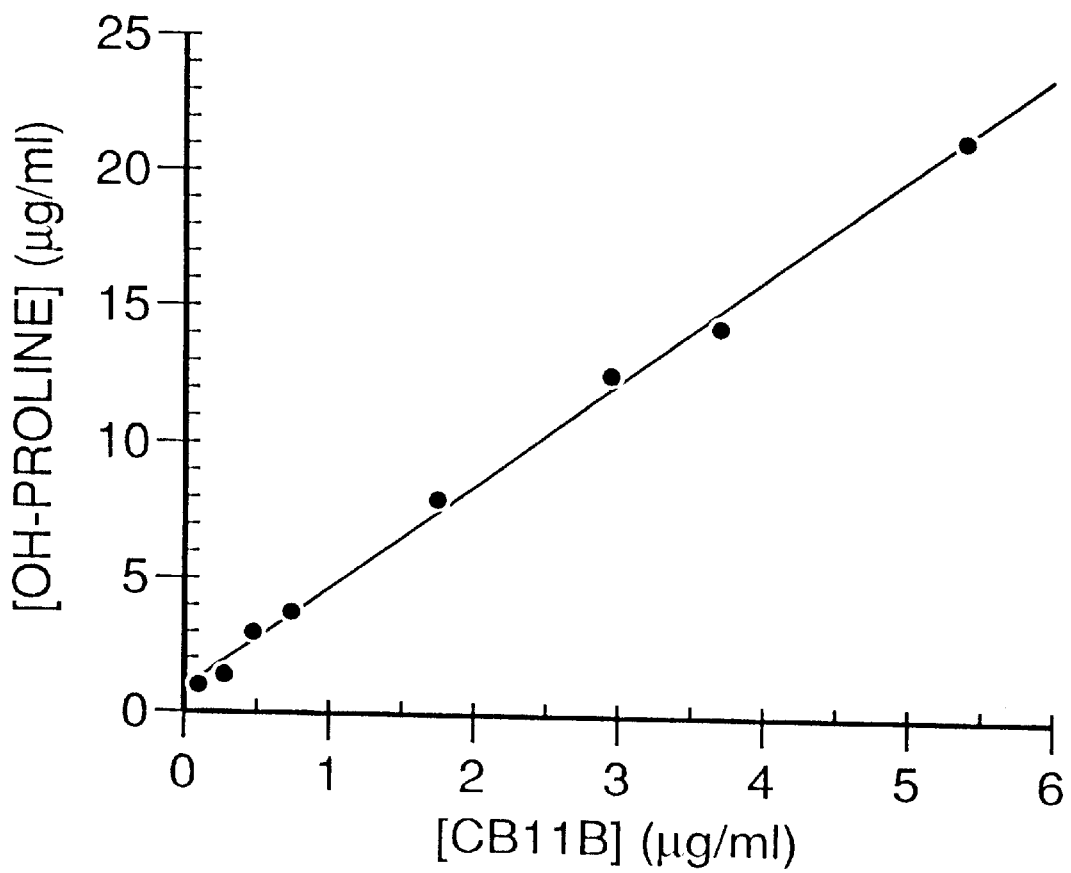

FIG. 6 represents a comparison of the concentration of CB11B and hydroxyproline in different HDC samples $r=0.9984$ ($p<0.0001$).

Figure 7:
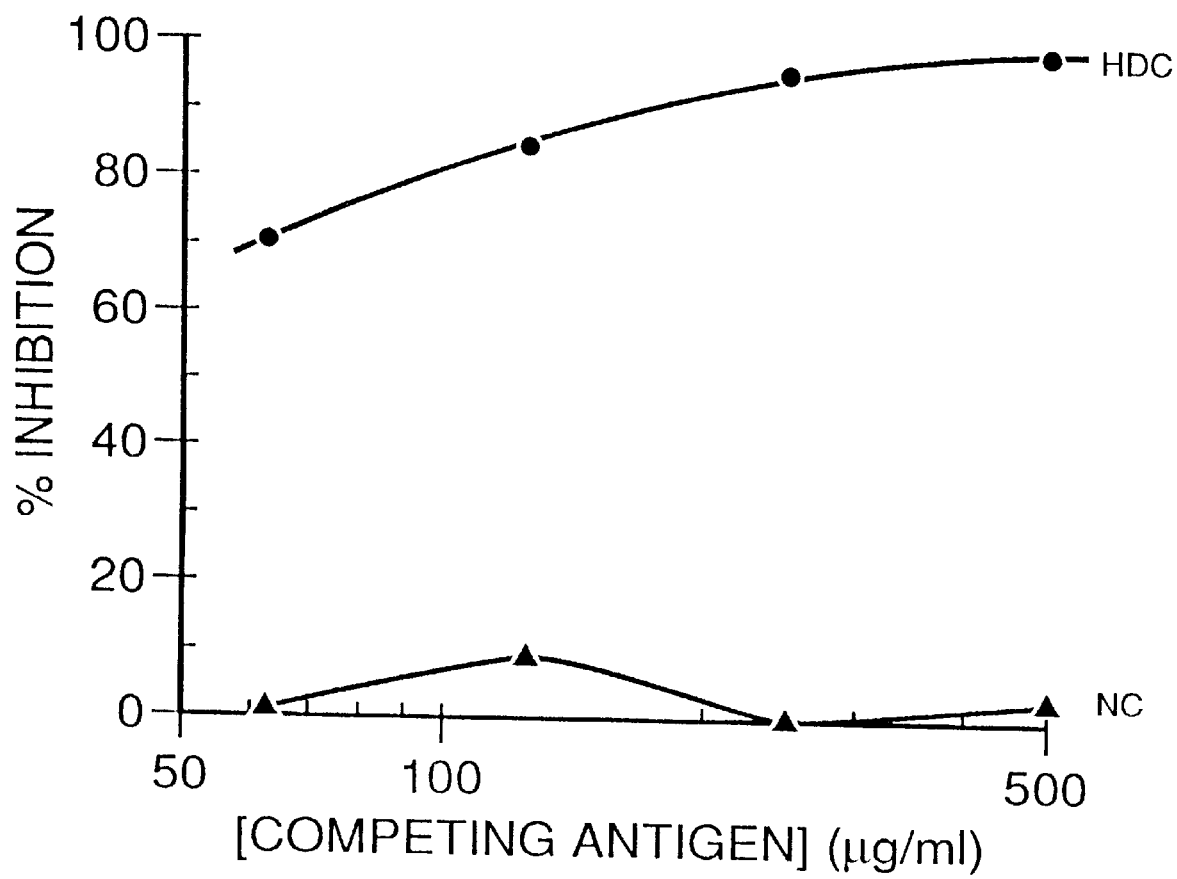

FIG. 7 represents a comparison between the percentage inhibition by heat denatured collagen (HDC) and native collagen (NC) detected by the method of the present invention.

Figure 8:
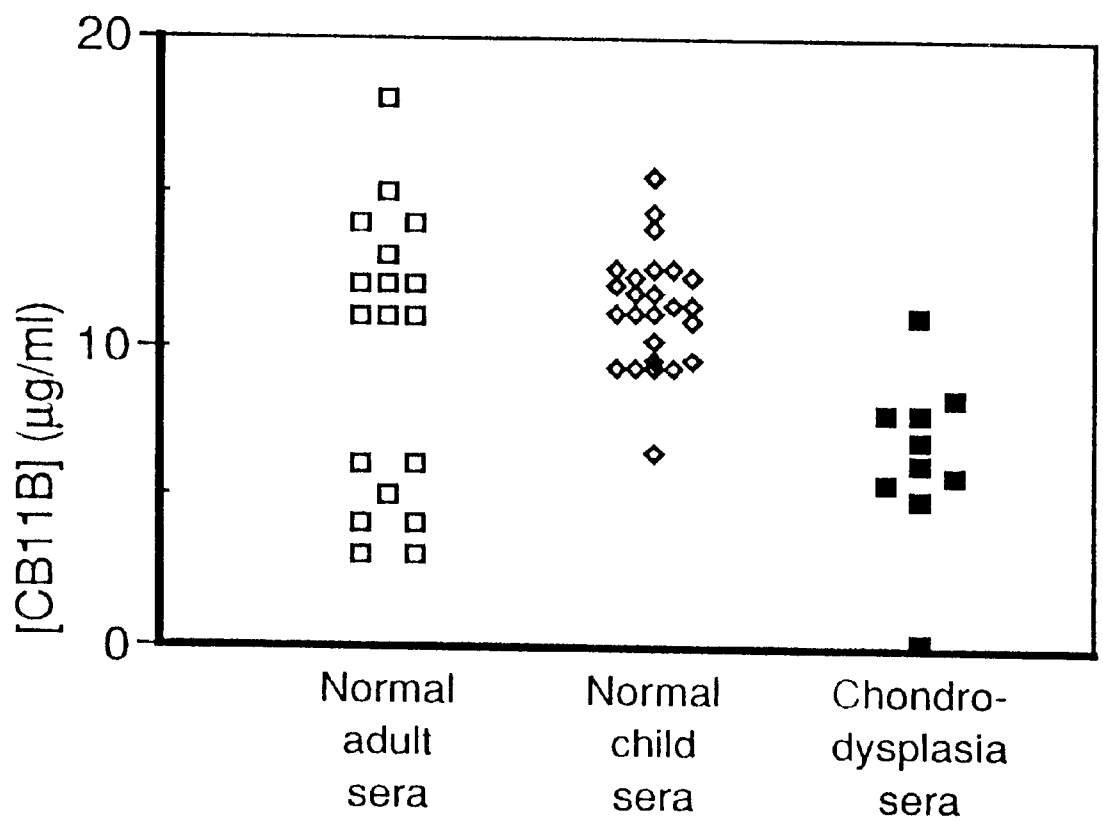

FIG. 8 represents the relative concentrations of the CB11B epitope in sera of normal children and adults and in children with chondrodysplasias.

Figure 9:
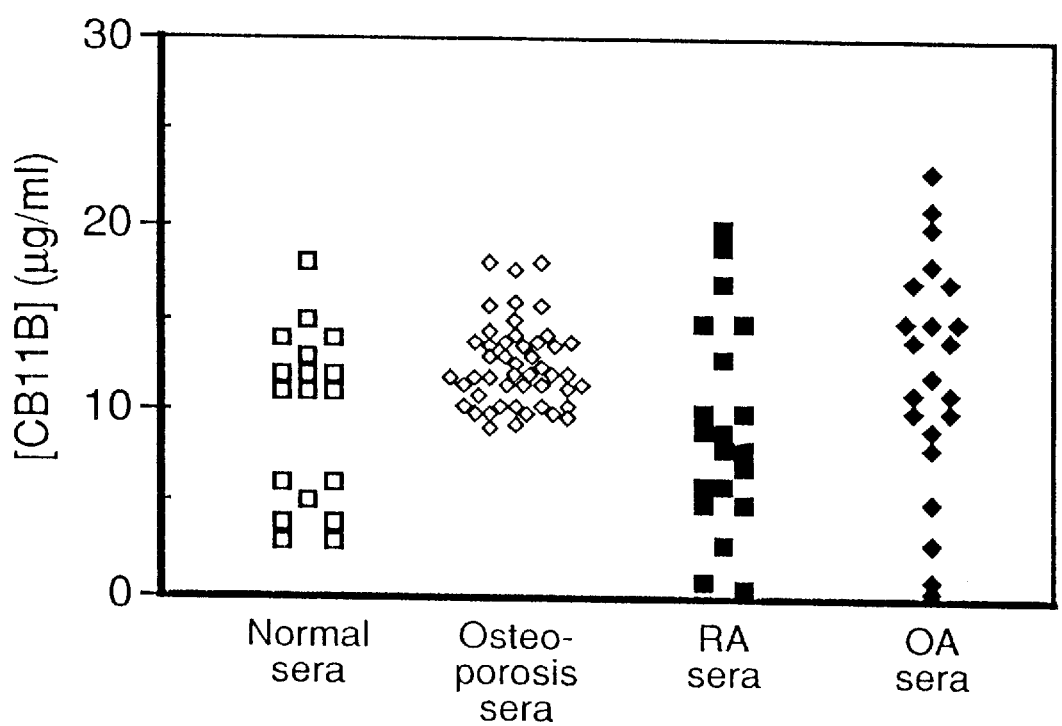

FIG. 9 represents the relative concentrations of the CB11B epitope in sera from normal adults and patients with osteoporosis, rheumatoid arthritis (RA) and osteoarthritis (OA).

Figure 10:
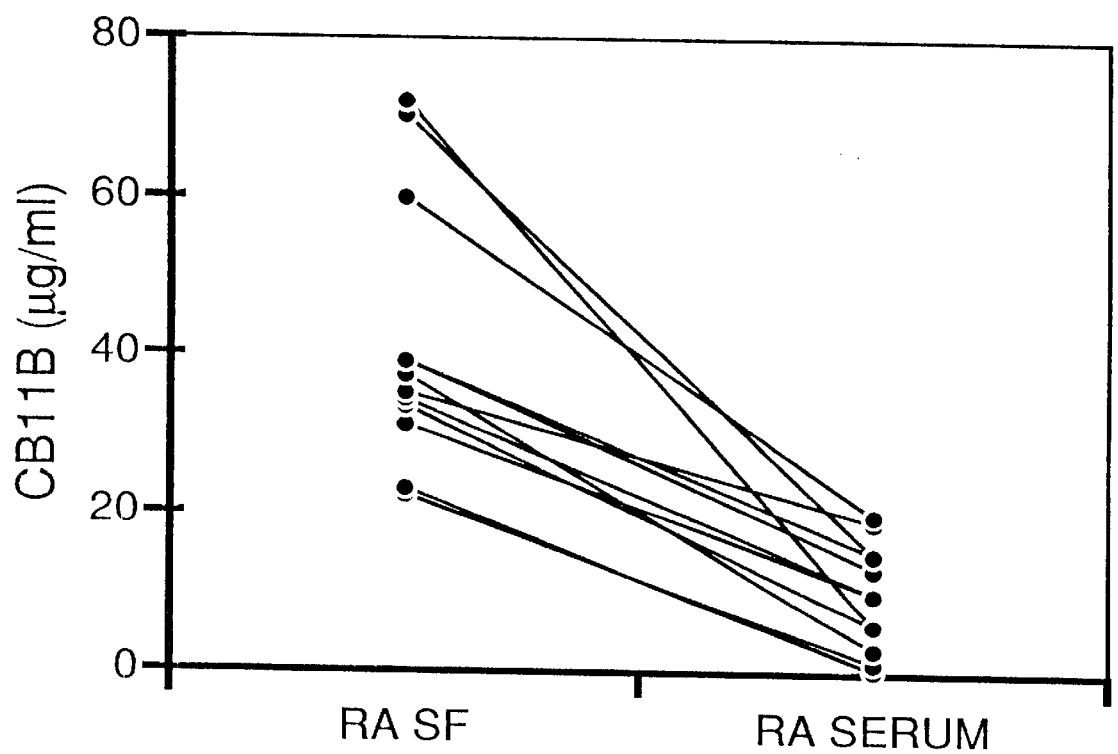

FIG. 10 represents the relative concentration of the CB11B epitope in synovial fluid (SF) and paired serum from individual patients with rheumatoid arthritis. Each line represents one patient.

Figure 11:
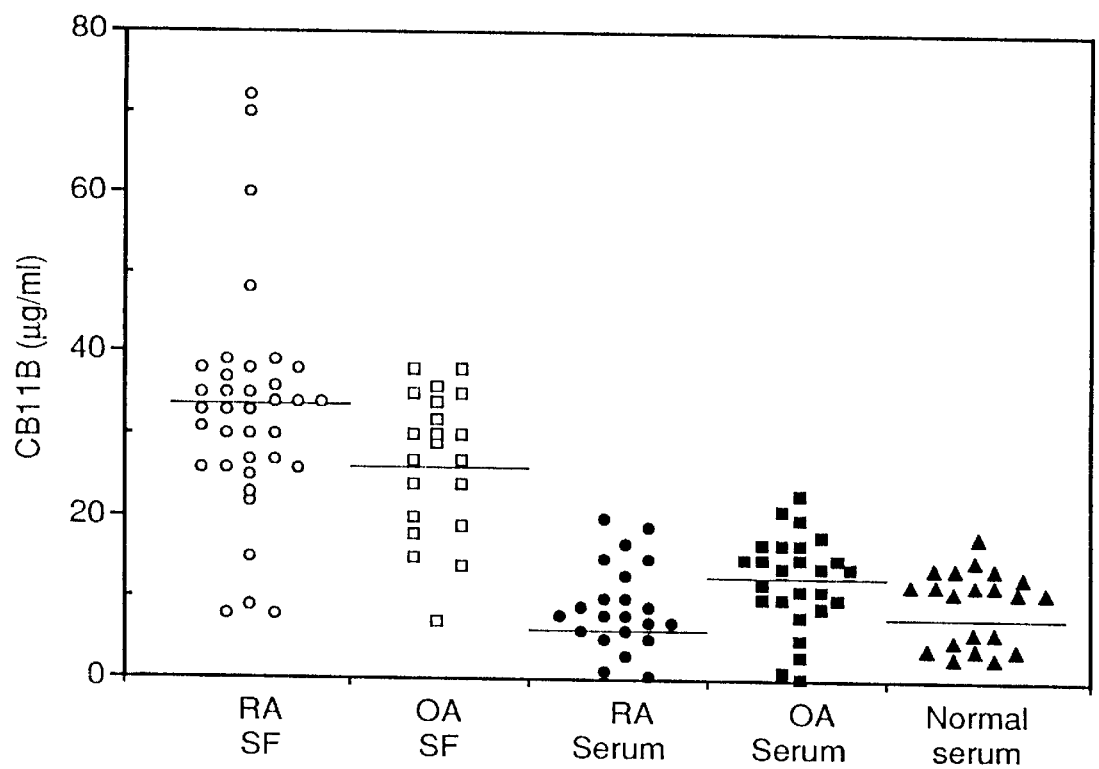

FIG. 11 represents the relative concentrations of the CB11B epitope in patients with rheumatoid arthritis (RA), osteoarthritis (OA) or in normal groups in sera and synovial fluids (SF).

Figures 12A, 12B, 12C:
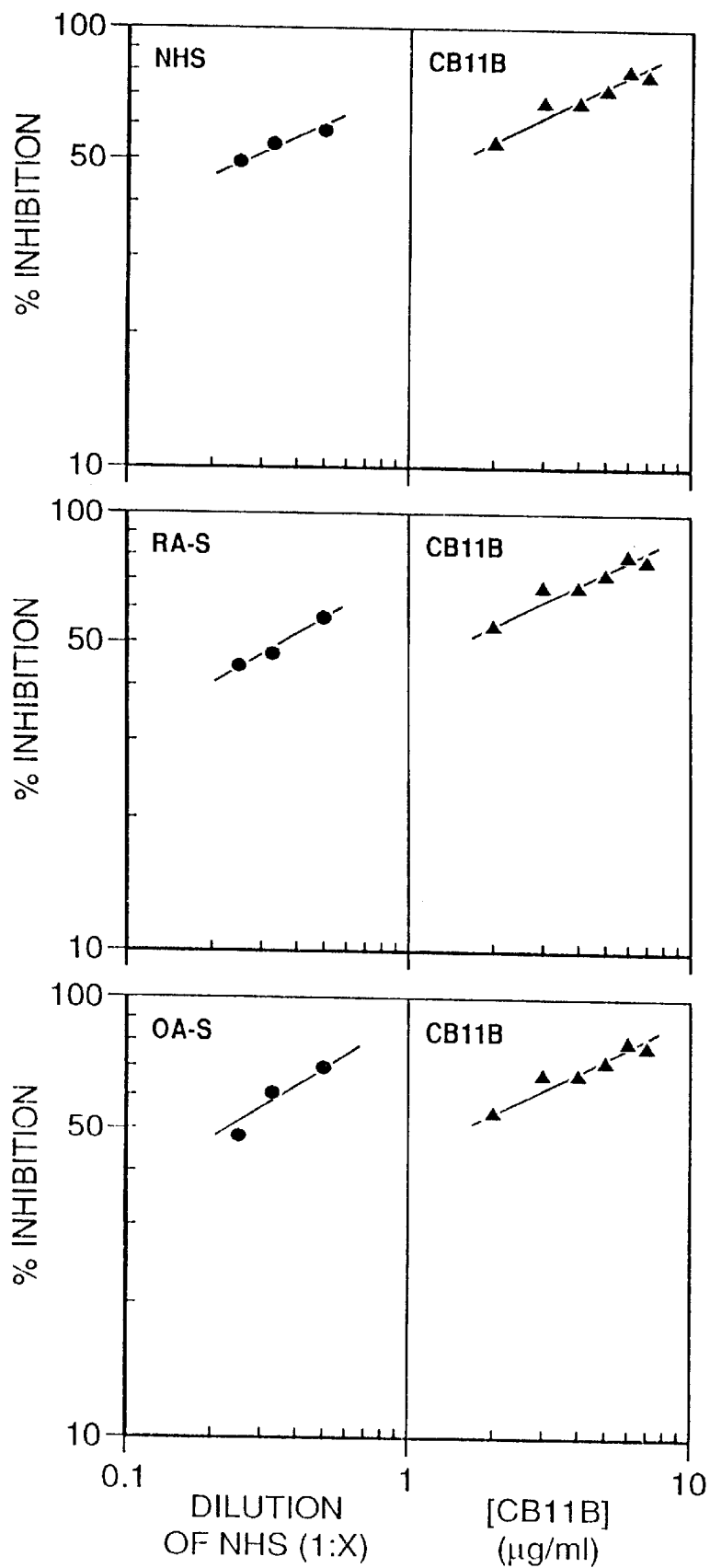

FIG. 12 represents results of immunoassays of: 12a normal human serum (NHS) 12b serum from rheumatoid arthritis (RA), and 12c osteoarthritis (OA) patients. The percentage inhibition of COL2-3/4m antibody binding by each serum is shown to exhibit parallelity to percentage inhibition produced by the CB11B peptide.

Figure 13:
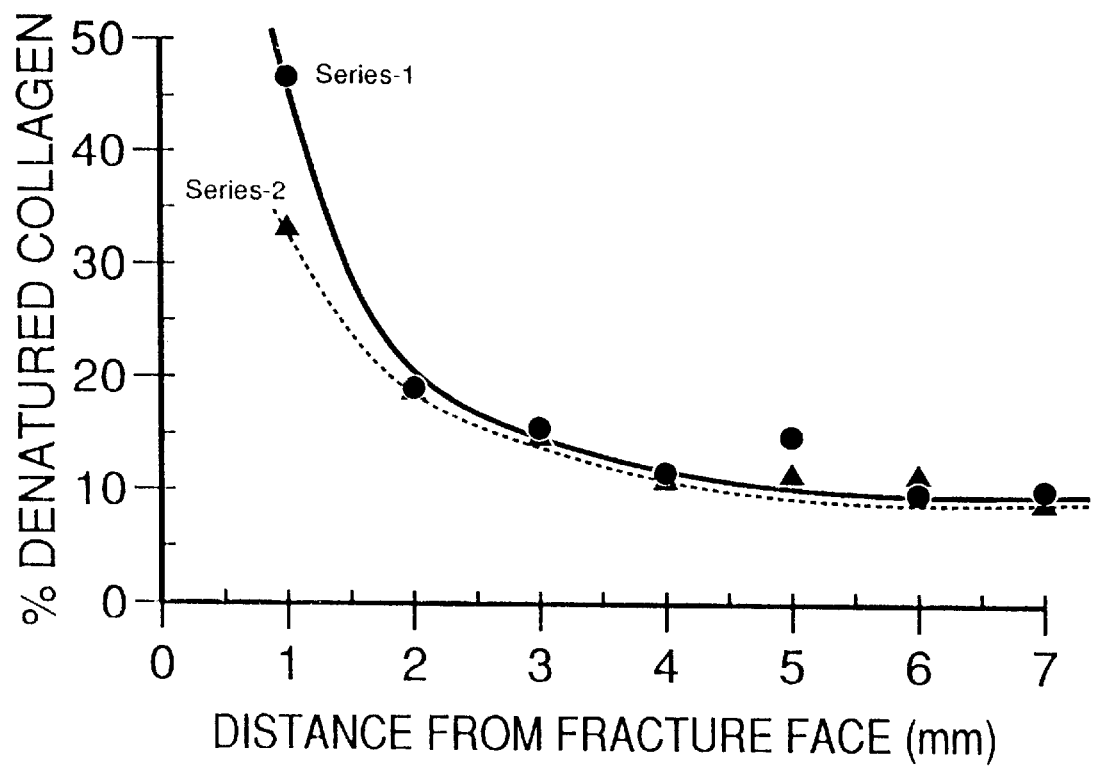

FIG. 13 represents the percentage denatured collagen in two separate bovine foetal epiphyseal and groeth plate cartilage discs labelled as series 1 and series 2.

Figure 14:
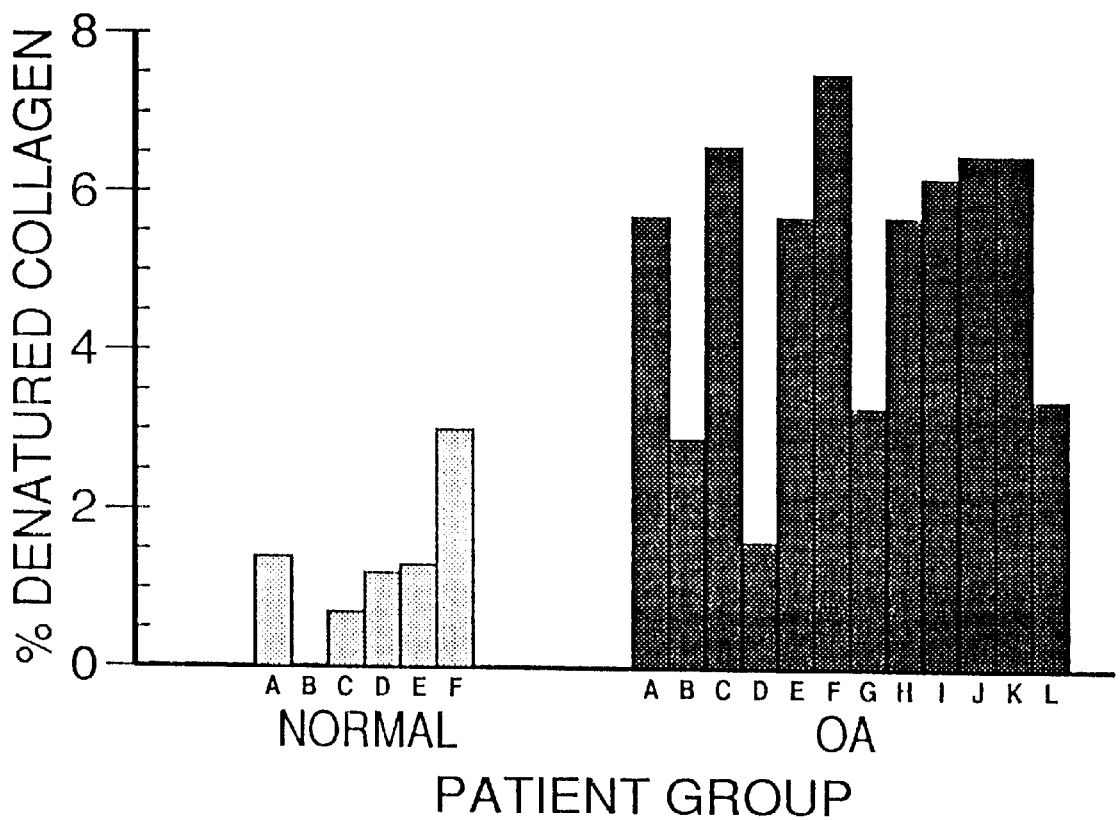

FIG. 14 represents the analysis of type II collagen denaturation (unwinding) in human femoral condylar articular cartilage from non-arthritic (normal) and osteoarthritic (OA) patients. Each bar represents one patient.

FIG. 15 (SEQ ID NOS 7–11, respectively) shows the sequence of the collagenase cleavage site on types I, II and III collagen and the sequence of the immunizing peptide used to produce the monoclonal antibody, COL2-3/4C$_{long\ (mono)}$.

Figure 16A:
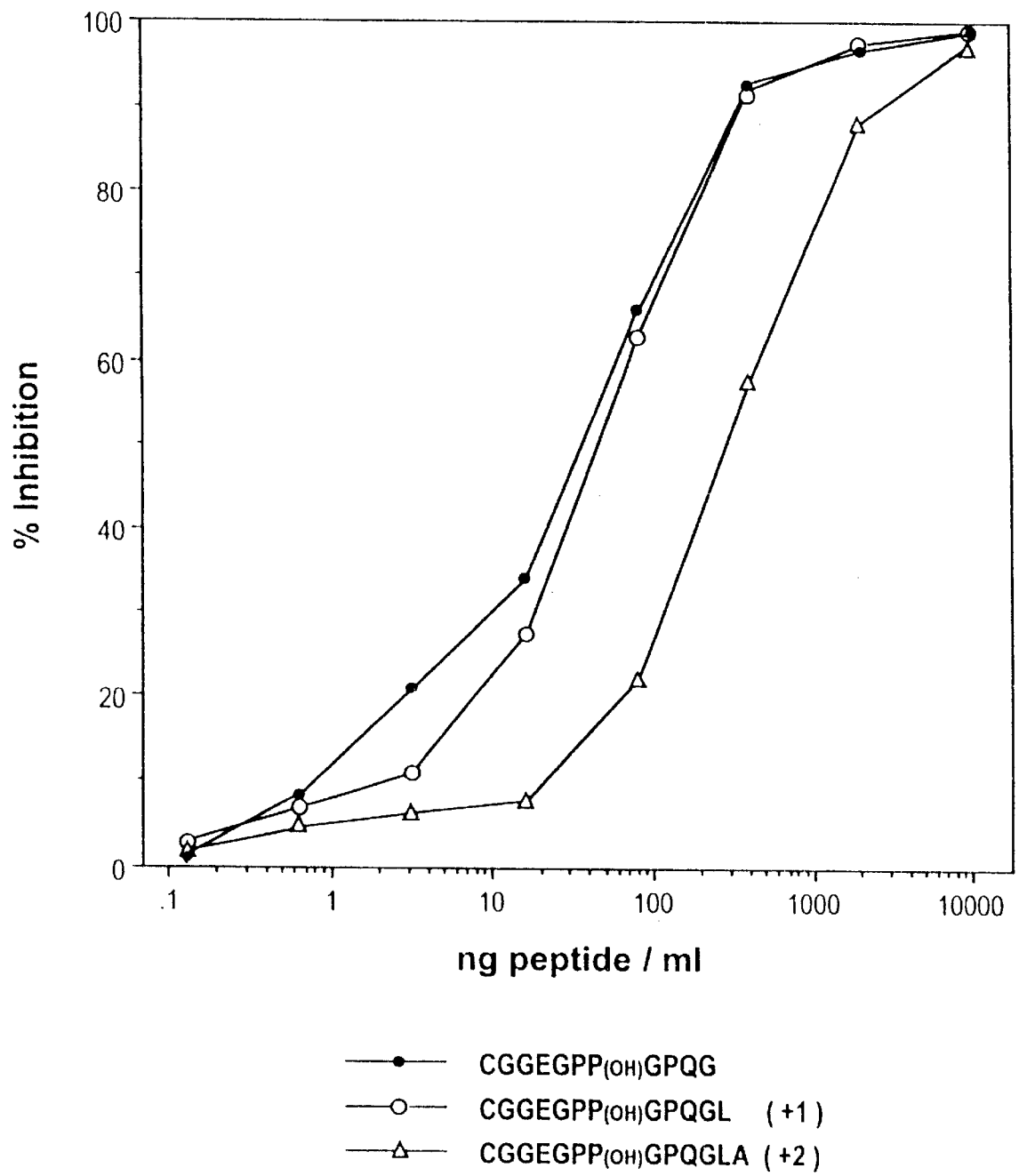

FIG. 16a (SEQ ID NOS 7 & 12–13, respectively) and 16b (SEQ ID NOS 7 & 14–16, respectively) are graphs which demonstrate the epitope specificity of the monoclonal antibody COL2-3/4C$_{long(mono)}$ as determined using competing synthetic peptides in inhibition ELISA. The sequence identified as COL2-3/4Cs is that recognized by the rabbit antibody COL2-3/4Cshort described in reference 49.

Figure 17:
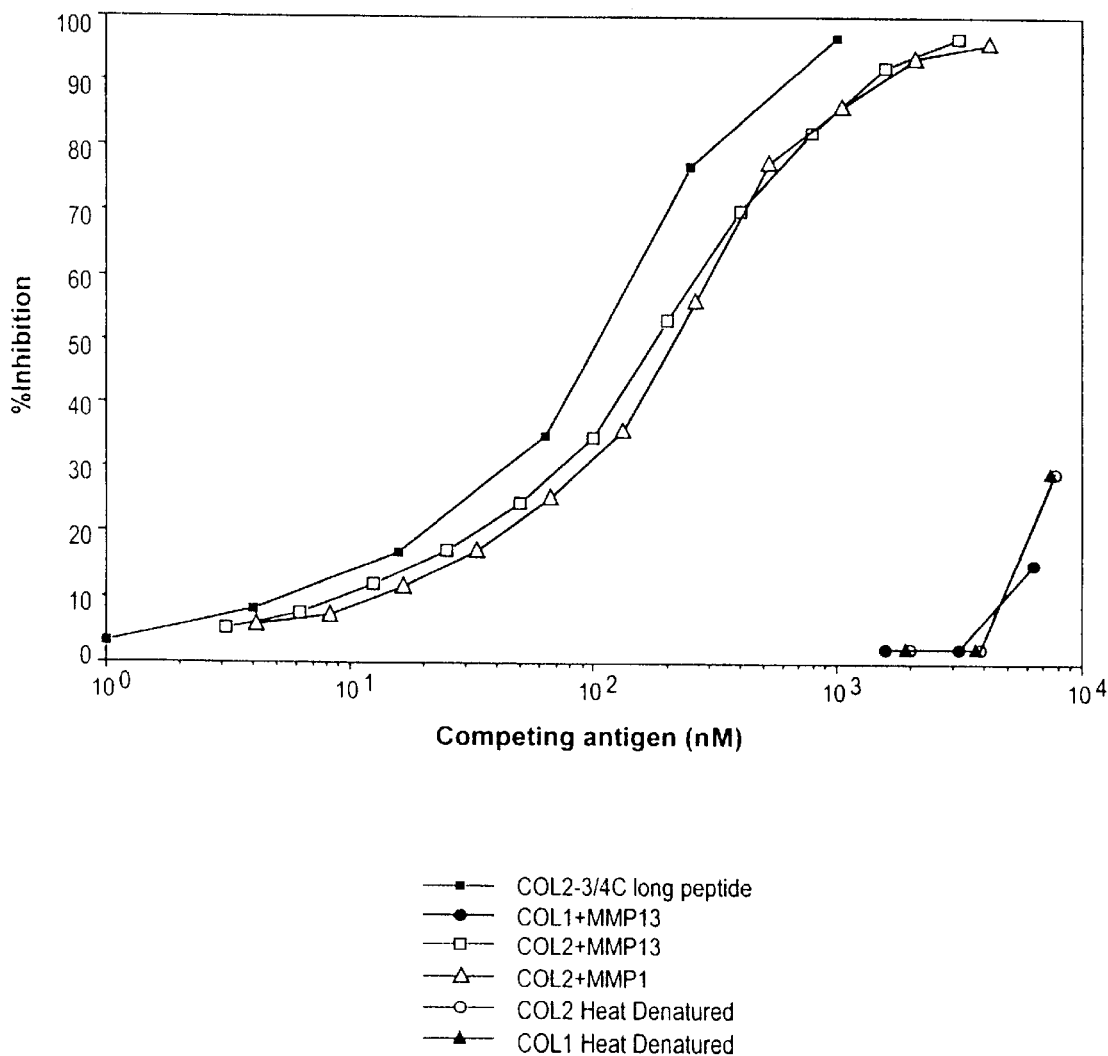

FIG. 17 is a graph which illustrates the specificity of the monoclonal antibody COL2-3/4C$_{long(mono)}$ for type II collagen (COL2) cleaved by human collagenases (+MMP-1 or +MMP-13) and which compares the reactivity of the antibody with heat denatured type II or I (COL1) collagens and with collagenase-cleaved type I collagen.

Figure 18A:
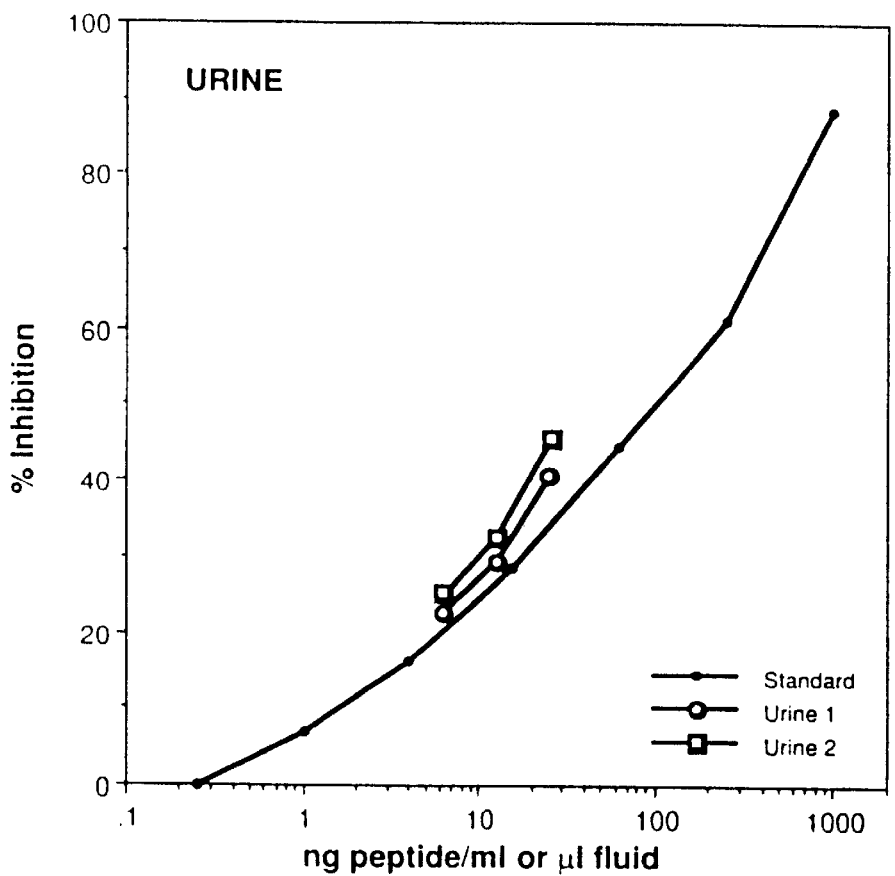
Figure 18B:
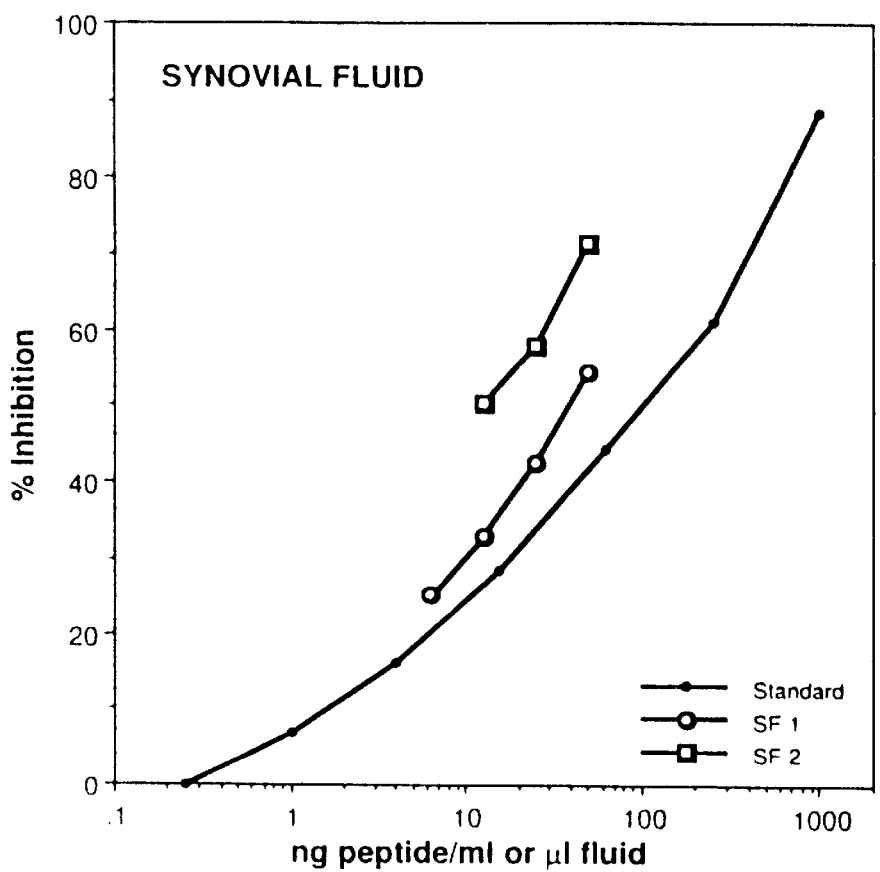
Figure 18C:
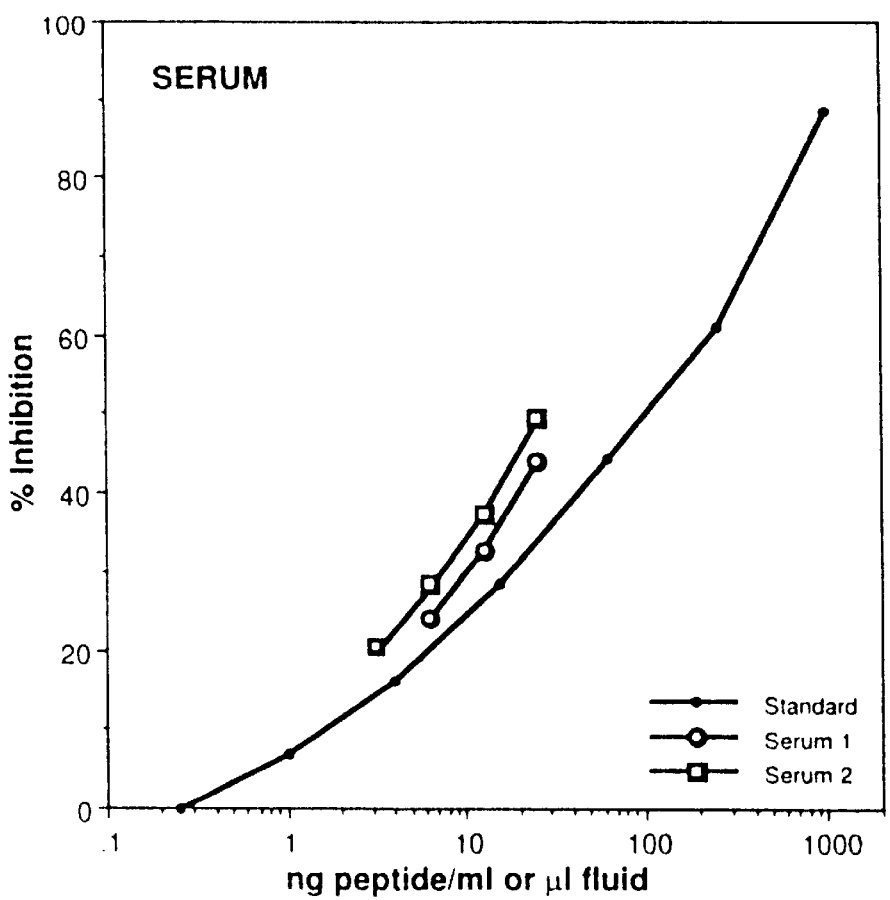

FIGS. 18a, 18b and 18c are graphs which illustrate the reactivity of the monoclonal antibody COL2-3/4C$_{long(mono)}$ in human urine, synovial fluid and serum respectively in comparison with reactivity with the immunizing peptide.

Figure 19A:
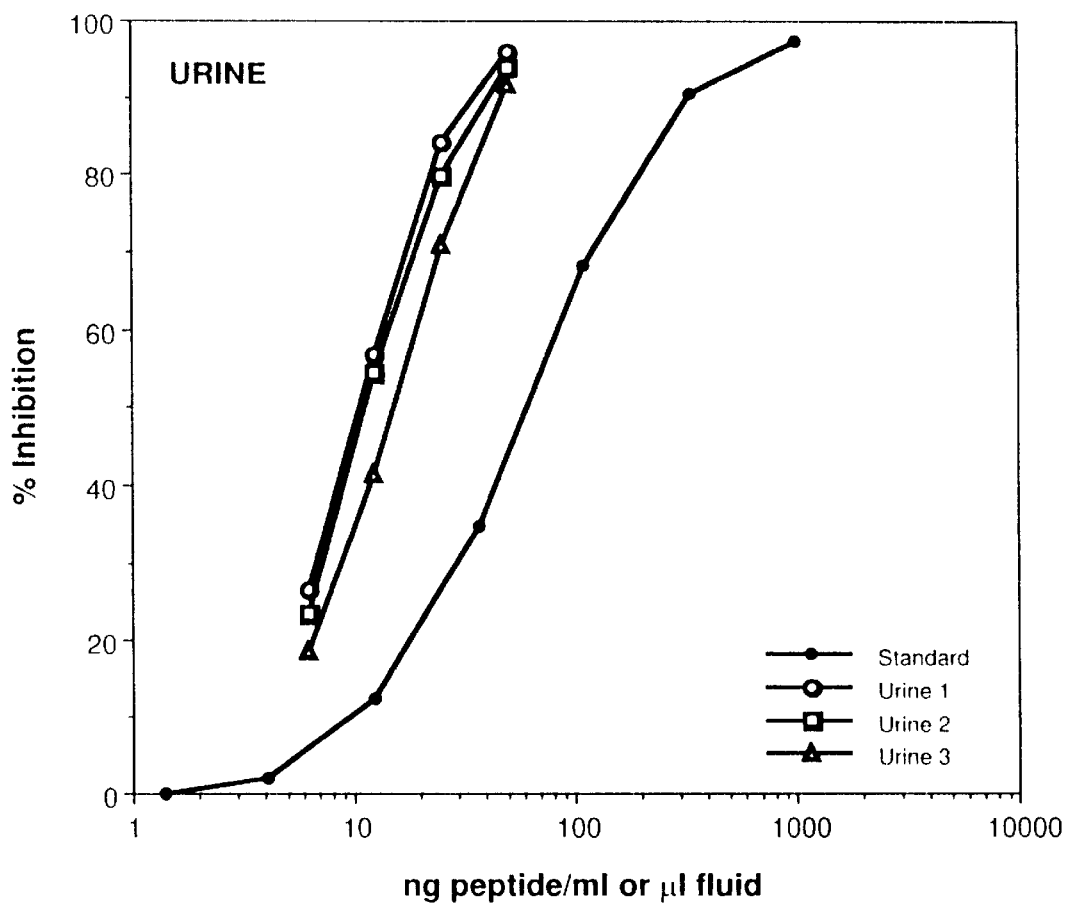
Figure 19B:
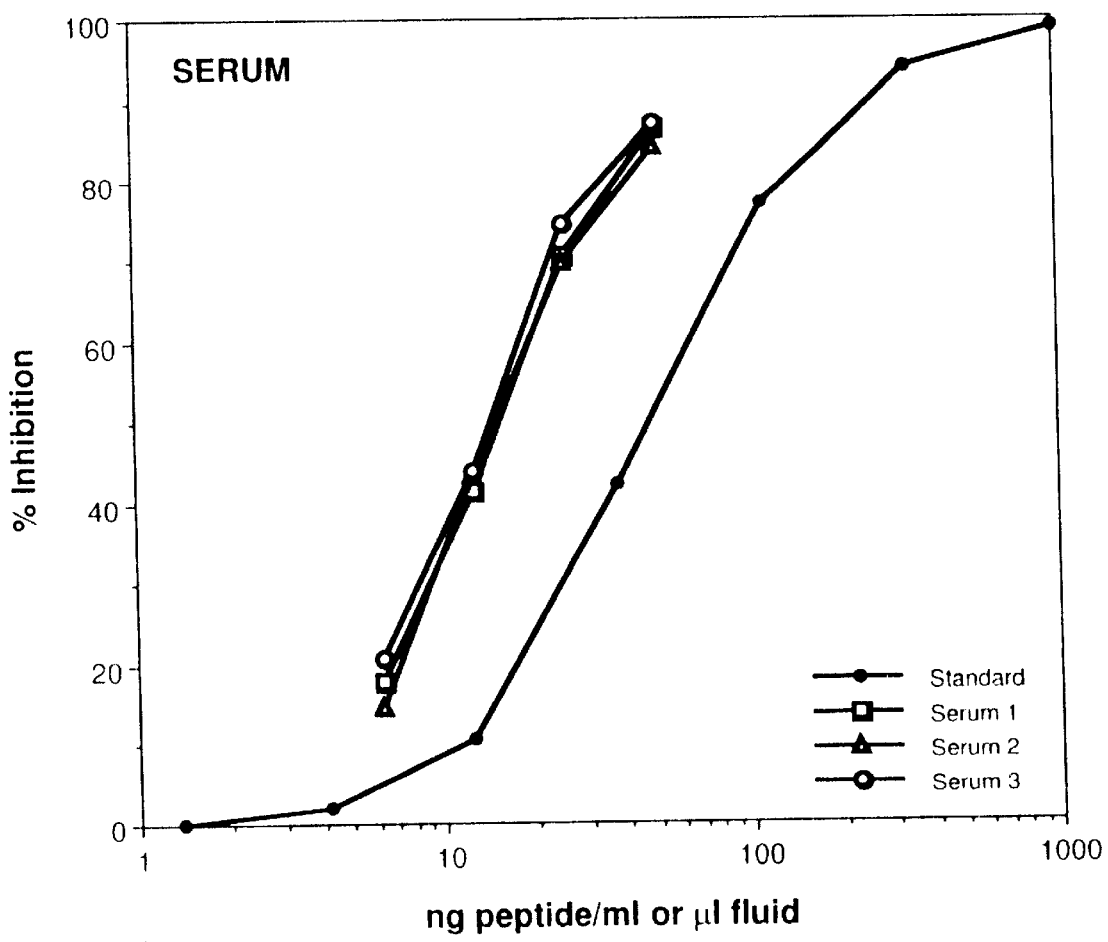

FIGS. 19a and 19b are graphs which illustrate the reactivity of the monoclonal antibody COL2-3/4C$_{long(mono)}$ in rabbit urine and serum, respectively, in comparison with reactivity with the immunizing peptide.

Figure 20A:
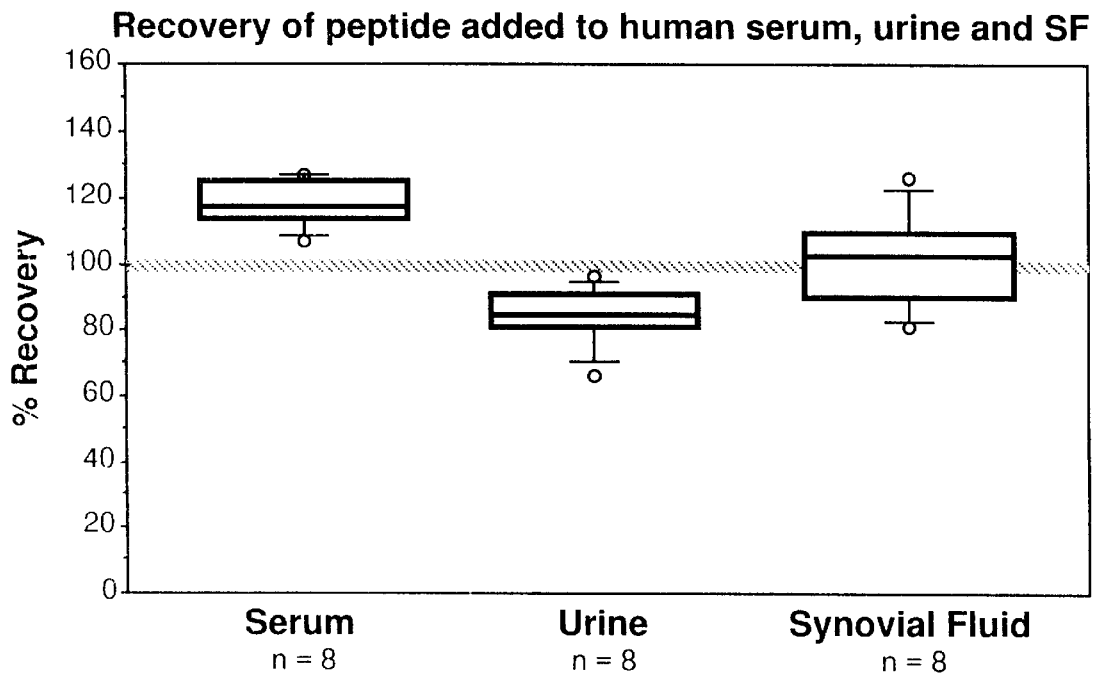
Figure 20B:
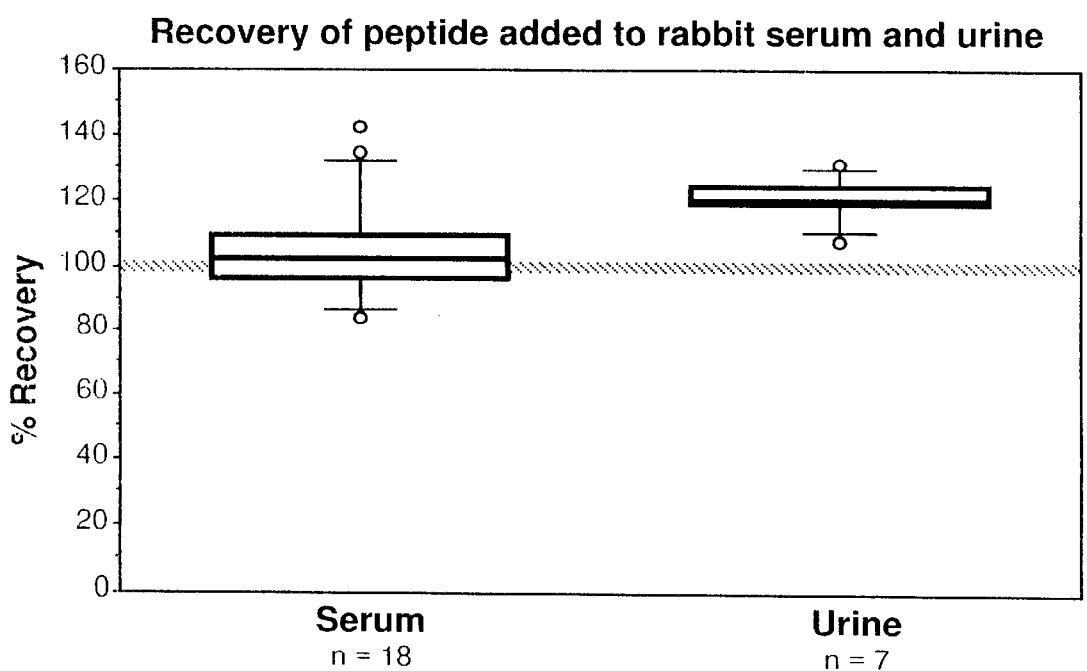

FIGS. 20a and 20b are bar graphs which illustrate the percentage recovery of immunizing peptide added to samples of urine, synovial fluid and serum from humans and serum and urine from rabbits, respectively, as determined by assay using the monoclonal antibody COL2-3/4C$_{long(mono)}$.

Figure 21A:
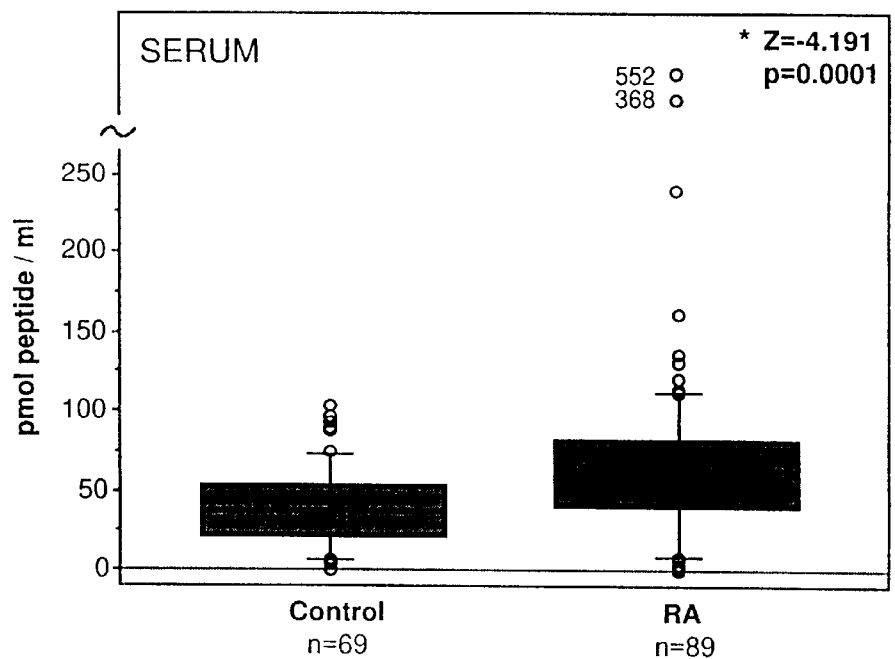
Figure 21B:
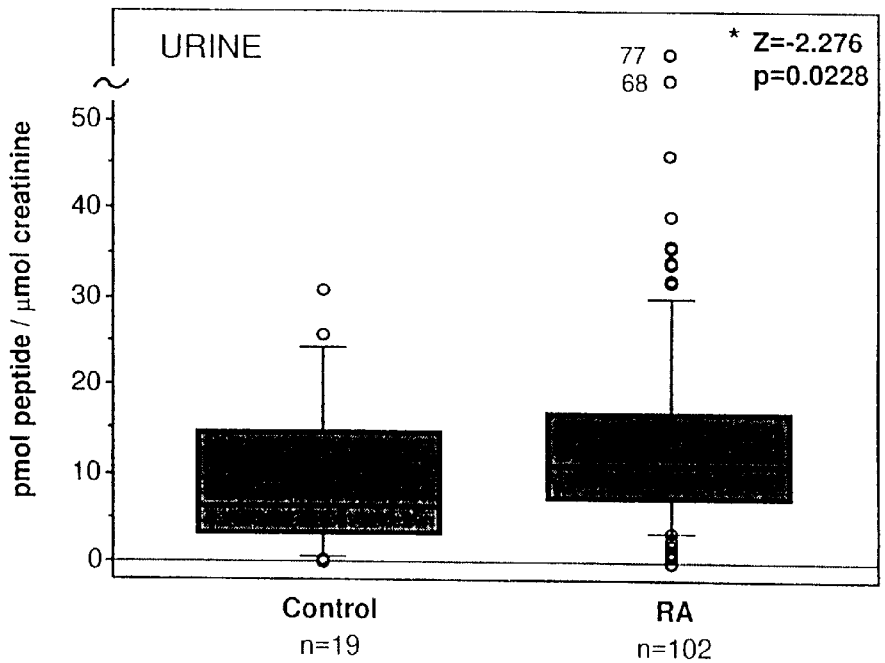

FIGS. 21a and 21b are graphs which illustrate the levels of the COL2-3/4C$_{long(mono)}$ epitope in human serum and urine.

DETAILED DESCRIPTION OF THE INVENTION

The invention relates to immunoassays for the detection and measurement of cartilage cleavage. The assays are performed by detection and/or measurement of epitopes on type II collagen which only become accessible following collagenase cleavage. The assays are constituted by providing a monoclonal antibody to a synthetic peptide, the sequence of which is derived from a segment that is specific to type II collagen. A synthetic peptide is produced on the basis of a sequence of human type II collagen α-chains. The antibody reacts with both this peptide and the three identical α-chains found in human, bovine, rat, hamster, rabbit and mouse collagen. It also recognizes fragments of type II collagen.

Immunoassay for Epitope on Unwound Type II Collagen

When type II collagen is cleaved in the helical region by collagenase, it unwinds. In one embodiment of the invention, the synthetic peptide is based on an epitope on type II collagen which is only accessible for antibody binding when the chains of the collagen molecule become unwound. A monoclonal antibody to this epitope will bind to unwound chains and fragments but not to native triple helical type II collagen. To the extent possible, the peptide chosen to prepare the antibody is specific to type II collagen. However, the antibody can cross-react with a very minor component (~1%) of cartilage collagen fibrils showing the same structure, namely type XI collagen α$_3$-chain, without affecting the overall accuracy of the assay. The epitope (CB11 B/H) which is recognized by the antibody, is not present in any other protein, according to protein sequence analyses.

The use of the antibody will hopefully assist us in identifying any other cleavage sites within the collagen molecule that may accompany the unwinding of the triple helix. Suffice it to say that the unwinding of the triple helix is not accompanied by such rapid secondary cleavage as to remove all α-chain fragments bearing the CB11B epitope and render them non-detectable. Such secondary trimming can occur by proteinases such as the 72 kD and 92 kD gelatinases, the expression of which are increased in OA cartilage as well as collagenase (11,15,20).

The antibody is used to develop an enzyme-linked immunoassay to detect unwinding of helical collagen when it is degraded in situ. This antibody can be used for quantitative assay, for immunohistochemistry and for isolation of type II collagen α-chains or fragments thereof containing the peptide sequence recognized by the antibody. Also, by radiolabelling the monoclonal antibody of the invention, it can be used for clinical imaging of sites of cartilage degradation.

In order to raise antibodies that can be efficiently used in the method of the present invention, it is necessary to determine from which portion of the overall collagen chain synthetic peptides having suitable immunogenic properties can be prepared. In one of the preferred embodiments of the invention, efforts were concentrated on a specific region of the type II collagen α-chain identified as the CB11 region, named after peptide 11 of the cyanogen bromide degradation method described by Scott et al (3) hereby incorporated by reference. Sites on the CB11 fragment of type II collagen that have hydrophilic domains were studied further for immunogenic properties. It was determined that criteria for the selection of a suitable peptide sequence are as follows:

a) the peptide should not include any lysine or hydroxylysine residues since hydroxylysines are also likely to be substituted with carbohydrate) or could involve cross-links; these modifications could block antibody-binding;

b) the peptide sequence should be well-conserved between species (to permit species cross-reactivity); and c) the peptide sequence should have minimal homology with sequences from the α-chains of other collagens besides type II.

Once a given portion of the collagen chain has been identified, based on the criteria set forth above as being suspected of possessing the desired immunogenic properties, the appropriate immunogenic sequence can then be chemically synthesized using standard chemistry and equipment such as the Applied Biosystems Model 431A solid phase peptide synthesizer. Once the appropriate peptide has been prepared, it can be coupled to an immunogenic vehicle, such as ovalbumin, to immunize mice from which monoclonal antibodies can be prepared. The resulting antibodies are then evaluated for reactivity to the peptide and heat denatured type II collagen (HDC) to determine whether they can be used to establish an inhibition assay.

As mentioned previously, the monoclonal antibody to be used in the context of the present embodiment has the ability to bind to an epitope on unwound collagen chains or fragments of collagen chains containing this epitope. The monoclonal antibody is also characterized in that it does not bind to native helical collagen.

The antibodies are prepared by immunizing animals with a peptide having the characteristics referred to above, conjugated to an appropriate immunogen. A preferred peptide for immunization is the above described CB11B peptide coupled to ovalbumin. The techniques employed to prepare the monoclonal antibodies are standard techniques which are known to those skilled in the art, details of which are provided further in the examples.

Alternatively, monoclonal antibodies which recognize heat denatured type II collagen, the immunizing peptide and one sub-peptide can be used.

The monoclonal antibodies that are to be used in the present invention are tested for inhibition with heat denatured type II collagen and the peptide used for immunization. Good inhibition would tend to indicate that the immunoassay can be used as such without further modification. The selective binding of the monoclonal antibody to the peptide used in immunization or native unwound collagen is important in order to have an assay that will be sufficiently sensitive to allow quantitative determination of cartilage breakdown. Cross-reactive antibodies are to be avoided if possible and this is where the selection of the synthetic peptide used in the production of the antibodies is important.

With the preferred antibodies prepared in the context of the present invention, it was demonstrated that antibody binding could be inhibited with the synthetic peptide on an ELISA plate. However, if denatured type II collagen α-chains were bound on the plate, a more sensitive assay was achieved upon inhibition with the synthetic peptide. With heat-denatured type II collagen provided on the ELISA plate, the synthetic peptide and HDC (heat denatured collagen) produced similar inhibition on a molar basis. The antibody did not react with native helical type II collagen.

In situations where the determination of cartilage breakdown is conducted based on a tissue sample, it is not preferable to simply react the tissue sample with a monoclonal antibody as described above because there is a strong likelihood that denatured helical collagen domains might be retained in the tissue by cross-linking and fibrillar packaging. To address this problem, the biological sample is first contacted with an enzyme having the ability to selectively cleave unwound collagens without cleaving the antibody-reactive epitope. The fragments of unwound collagen are then extracted from the biological sample to produce an extract of unwound collagen fragments. This extract can then be assayed by being contacted with the monoclonal antibody described above.

It is important to select a protease that will not cleave or degrade a region of the epitope that is reactive to the monoclonal antibody used in the assay. This can be achieved by either preparing an antibody that binds to an epitope not cleaved by the desired enzyme or by selecting an enzyme that cleaves collagen in a region outside the targeted epitope. In the context of the present invention, chymotrypsin is one preferred enzyme that can be used to cleave unwound collagen chains. Another suitable enzyme is trypsin. These enzymes are capable of cleaving unwound type II collagen but ordinarily cannot cleave the helical regions of native collagen. Unsuitable enzymes include papain and pepsin.

In order to assess the level of unwinding of collagen in a biological sample, it is necessary to measure the total amount of native helical collagen present in the analyzed sample. The native collagen fragments must first be unwound and solubilized because in their helical state, the epitopes which can bind to the monoclonal antibodies described above are not accessible. Various techniques can be used to achieve this purpose. Among them is the proteolytic cleavage and solubilization of native collagen by selected enzymes. Among these enzymes, proteinase K is a preferred choice although when it is used, it is necessary to heat the mixture of proteinase K and the solubilized collagen to ensure complete unwinding of the helical chains as well as destroy the proteinase K activity.

The use of the enzymes referred to above is important as they permit the measurement of the degree of cartilage degradation in a given biological sample.

The immunoassay for an epitope on unwound type II collagen has at least three potential applications. Firstly, it can be used to detect and/or measure collagen degradation products in a biological sample through the use of the monoclonal antibodies described above. Secondly, it can be used to determine the amount of cartilage degradation in tissues by combining these antibodies with enzymes having the ability to cleave unwound collagen as well as means for unwinding remaining native helical collagen. Thirdly, it can be used to measure total collagen content in a biological sample.

In situations where it is desired to monitor collagen degradation in a biological sample, such as a body fluid, the monoclonal antibody is contacted with the sample and incubated for a period of time sufficient to provoke the desired immunological reaction.

The evaluation of collagen unwinding in a body fluid can be carried out through a kit which first comprises a monoclonal antibody having the characteristics described above.

The kit also comprises a solid support for binding proteins. A wide variety of solid supports can be used. Nitrocellulose sheets or similar materials can be used but in particular, it is contemplated to use as the solid sorbent a plastic material such as polystyrene, a polyvinyl or other plastics which could include polyethylene, polypropylene, nylon and derivatized glass. The proteins that are bound to the solid support can be either the antibody itself, the synthetic peptide against which the antibodies were raised or heat-denatured collagen.

Also, the kit comprises a labelled antibody to measure the binding of the monoclonal antibody to unwound collagen. This antibody can be radioactively or enzymatically labelled through techniques that are within the knowledge of the person skilled in the art. Preferred in the context of the present invention is an alkaline phosphatase-conjugated antibody used in combination with an alkaline phosphatase substrate which produces a coloured reaction product.

When the kit of the present invention is to be used for quantitative measurement of cartilage degradation from a tissue sample, it further comprises an enzyme having the ability to selectively cleave unwound collagen chains in the biological sample without cleaving antibody-reactive epitope on the collagen chains. The kit can further comprise another enzyme having the ability to solubilize helical collagen from cartilage without cleaving antibody-reactive epitope. It is to be noted that although the enzymes referred to above are not absolutely necessary to carry out the method of the present invention when a biological fluid is assayed, these enzymes could be optionally used in body fluid samples.

If it is to be used in total collagen degradation, the kit comprises the monoclonal antibody having the characteristics described above, a solid support for binding proteins as well as a labelled antibody to measure the binding of the monoclonal antibody to unwound collagen. Ideally, the kit also comprises means for unwinding the collagen present in the biological sample to be analyzed.

The monoclonal antibody described above could also be used for detecting in vivo the presence of damaged collagen in joints. By employing the Fab portion of the antibody, which can penetrate cartilage, in vivo diagnostic imaging of collagen degradation in joints can be performed. For this application, the Fab portion of the antibody is preferably radiolabelled with a short lived radioactive emitter such as Yttrium or Indium. The labelled antibody is injected in patients. It is bound and retained in sites of damage to type II collagen, such as in arthritic cartilage in diseased joints. Using radiological imaging with a gamma-camera, it is possible to detect the radioactivity and hence collagen damage in cartilage in joints.

Immunoassay for Epitope Near the Collagenase Cleavage Site

In a second embodiment of the invention, an antibody is raised to a synthetic peptide based on an epitope on type II collagen which is near the site of collagenase cleavage. The ability of an antibody to bind to this epitope is not dependant on unwinding of the collagen chains, but rather, is dependant on cleavage by collagenase.

The primary collagenase cleavage site in type I, II and III collagens is located between residues 775 and 776. However, as shown in FIG. 15, the amino acid sequence of type II collagen is distinct from that of types I and III collagens in the domain immediately amino terminal to the cleavage site. The sequences of types I and II collagens are identical for the first four residues (SEQ ID NO:5) (GQPG) in the $\alpha_1$(II), $\alpha_1$(I) and $\alpha_2$(I) chains, although P may or may not be hydroxylated, but immediately thereafter the sequences are different. This gives rise to the possibility of preparing an antibody to an epitope in this region that may be specific for type II collagen. However, since the four residues adjacent to the collagenase cleavage site are the same, it is not possible to predict that an antibody that has specificity for type II collagen and also reacts with fragments generated by a collagenase could be prepared.

The inventors of the subject application have succeeded in developing a mouse monoclonal antibody termed COL2-3/4C$_{long(mono)}$ that reacts specifically with type II collagen but only after cleavage by collagenase. The antibody does not react with type I collagen after cleavage with collagenase. Furthermore, the inventors have developed an immunoassay using this monoclonal antibody which is capable of detecting collagenase-generated fragments of type II collagen in human serum, plasma and synovial fluid. An advantage of this particular assay is that it does not require enzymatic treatment to isolate unwound collagen fragments. A kit for performing the assay is also provided which contains a solid support for binding proteins as described above, and the monoclonal antibody to the epitope near the collagenase cleavage site which can be radioactively or enzymatically labelled through techniques that are known to those skilled in the art. Preferred in the context of the present invention is an alkaline phosphatase-conjugated antibody used in combination with an alkaline phosphatase substrate which produces a coloured reaction product.

The following examples are provided to further illustrate the present invention.

EXAMPLE 1

Preparation of Immunogenic Peptide CB11B

Figure 2:
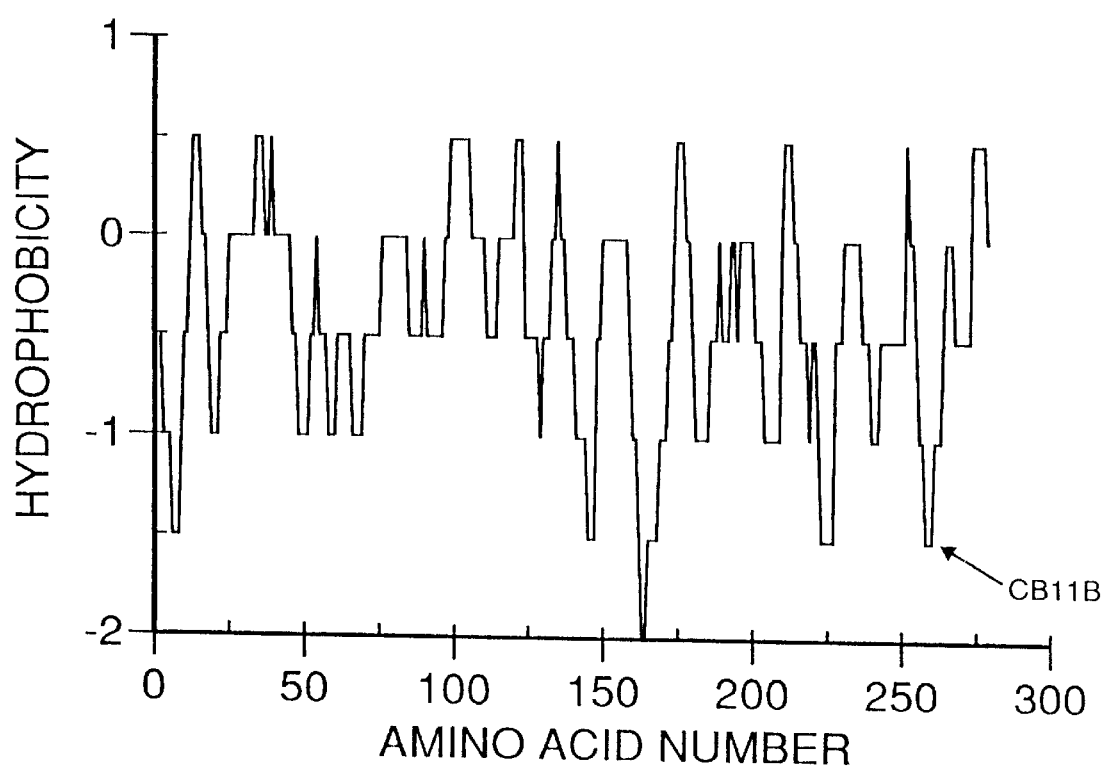
FIG. 2 represents the hydrophobicity/hydrophilicity plot for the CB11 peptide of type II collagen. A negative hydrophobicity value represents a hydrophilic region of the amino acid sequence.

A. Identification of an Immunogenic Epitope on Peptide CB11 and Preparation of a Synthetic Peptide Five hydrophilic domains (hydrophilicity less than 1.0) were identified from the hydrophobicity/hydrophilicity profile of the CB11 peptide of human type II collagen. The sequence of type II collagen is shown in FIG. 1 and SEQ ID NO:1. The CB11 peptide (referred to a CNBr:11 on FIG. 1) is shown to span from aa 255 to aa 533 and is shown in SEQ ID NO:2. The hydrophobicity/hydrophilicity plot for the CB11 peptide is shown in FIG. 2. A 21 amino acid sequence from one of these domains satisfied the three additional criteria for peptide sequence selection, that is no lysine or hydroxylysine residues, conservation of the peptide sequence between species and minimal homology with sequences from α-chains of other collagens besides type II. The sequence of this peptide, termed CB11B, is shown in FIG. 3 and SEQ ID NO:3. The peptide was synthesized with an additional N-terminal cysteine for conjugation to ovalbumin and a C-terminal tyrosine (for possible radiolabelling with $^{125}$I) at a 0.25 mole scale, using standard FAST-MOC chemistry on an Applied Biosystems Model 431A solid phase peptide synthesizer. The 23 amino acid peptide (termed CB11B, SEQ ID NO:3) has the formula:

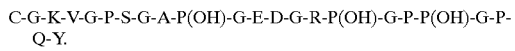

In the above formula, (OH) represents hydroxylation of proline, C is used to bind to ovalbumin and Y can be used for labelling with 125, if required for radio-immunoassay applications.

In the case of this peptide, it was assumed that all proline residues in the "Y" position of the Gly-X-Y repeat sequence were hydroxylated. However, the hydroxyl group does not appear to contribute significantly to the hydrophilicity of the overall CB11 peptide since the hydrophilicity profile was almost identical when hydroxyproline values were compared to those of proline. Crude peptides were purified by reverse phase chromatography (Prep-10 aquapore C8 column, Applied Biosystems) using an acetonitrile gradient in 0.1% trifluoroacetic acid.

B. Coupling of Synthetic Peptide to Ovalbumin

The bifunctional reagent bromoacetic acid-N-hydroxy succinimide ester (Sigma) was prepared fresh at 60 μg/ml in dimethyl formamide. For coupling, 0.2 ml of this solution was added, dropwise, with continuous stirring to 2 ml of ovalbumin (25 mg/ml; Sigma) dissolved in 0.1M phosphate buffer, pH 7.0, containing 1 mM EDTA, at 4° C. The mixture was then allowed to equilibrate to room temperature over 30 minutes. The activated ovalbumin was separated from unreacted coupling reagent by gel filtration using a Sephadex G25 column (27×2.2 cm) eluted with the EDTA/phosphate buffer described above. The peptide to be coupled was dissolved in 0.1M phosphate buffer, pH 7.0 and 5 mg was added to approximately 4 mg of activated ovalbumin (about 1.5 ml of the Sephadex G25-eluate peak fractions). The mixture was stirred for 2 h at room temperature and then incubated overnight at 4° C. The conjugate solution was dialysed exhaustively against azide-free phosphate buffered saline (PBS). Success of the coupling reaction was determined by confirming a reduced electrophoretic mobility of the peptide-ovalbumin conjugate compared to unconjugated ovalbumin.

EXAMPLE 2
Preparation of Monoclonal Antibodies to Synthetic Peptide CB11B
A. Preparation of Hybridoma Cells Four 8–10 week-old female BALB/c mice were each immunized by intra-peritoneal (i.p.) injection with 100 μg of the synthetic peptide of Example 1 conjugated to ovalbumin in 100 μl PBS and emulsified with 100 μl of Freund's complete adjuvant. Each mouse received four subsequent i.p. immunizations with the same quantity of antigen emulsified in Freund's incomplete adjuvant, at two week intervals. Serum samples were collected, 10 days after the second and fifth immunizations, by retro-orbital bleeding and tested in an ELISA for positive reactivity with both the synthetic peptide of Example 1 and heat denatured type II collagen (HDC) and negative reactivity against helical (native) type II collagen.

The mouse showing the best serum antibody response was given a sixth immunization, with unconjugated peptide in azide-free PBS (100 μg i.p. and 100 μg intravenous). Three days later, the animal was sacrificed by asphyxiation and the spleen removed. The splenocytes were isolated by gently grinding the tissue through a sterile metal mesh. They were fused to SP2/0 myeloma cells and cloned as described by de Fazekas and Scheidegger (4) hereby incorporated by reference. Hybridoma cells from the best clone (COL2-3/4m) were injected i.p. into female retired breeder BALB/c mice that had been primed i.p. with pristane (Sigma). Ascitic fluid containing a monoclonal antibody designated COL2-3/4m which was reactive with both CB11B synthetic peptide of Example 1 and HDC was harvested after 8–10 days. The antibody isotype was determined using a commercial isotype screening kit (Southern Biotechnology Inc., Birmingham, Ala.).

The hybridoma was deposited under the Budapest Treaty at the American Type Culture Collection (ATCC), 10801 University Blvd., Manassas, Va. 20110-2209, USA on Nov. 17, 1992 and was assigned ATCC designation HB 11202.

B. Characteristics of Monoclonal Antibody COL2-3/4m

COL2-3/4m was found to have an IgG$_1$ isotype. The specific epitope sequence recognized by the monoclonal antibody was identified by synthesizing short, overlapping peptides from within the sequence of CB11B and testing these for reactivity with the monoclonal (data not shown). The epitope was identified as peptide CB11B/H, a 13 amino acid sequence containing three hydroxyproline residues (FIG. 3b and SEQ ID NO:4). The sequence of this epitope is as follows:

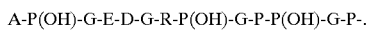

Shortening of the sequence at the amino-terminus by removing one amino acid reduced reactivity with COL2-3/4m by 70% and shortening at the carboxy terminus reduced reactivity by 33% when one amino acid was removed and 92% when two were removed (data not shown). Peptide CB11B/H retained full reactivity with antibody COL2-3/4m in an inhibition assay, even when proline was substituted for any one of the hydroxyproline residues (data not shown). The sequence of epitope CB11B/H was compared to those of all proteins included in release 22 of the Swiss-Prot protein sequence database, using MacMolly Tetra Software. (Soft Gene GmbH, Berlin, Germany). The only protein sequences found to contain the epitope CB11B/H were those of the α$_1$(II) and the α$_3$(XI) chains. Monoclonal COL2-3/4m cross-reacts with denatured type II collagen from all mammalian species so far studied (including mouse), indicating that the epitope contained within peptide α$_1$(II)-CB11B is highly conserved.

EXAMPLE 3
Specificity of COL2-3/4m Monoclonal Antibody for Type II Collagen

Bovine and human type II collagen and bovine types I and III collagens were prepared by differential salt precipitation, as described by Dodge and Poole (1) and Epstein (5). Bovine type XI collagen was prepared following the technique described by Eyre et al (6). Type X collagen can be purified by the method described by Kirsch et al (7).

Bovine native type II collagen was initially dissolved in 0.5M acetic acid and then diluted to a final concentration of 0.5 mg/ml in 100 mM Tris-HCl, pH 7.6, containing 10 mM CaCl$_2$ and recombinant human collagenase which had been activated by incubation with 0.25mM amino-phenyl mercuriacetate for 10 minutes at 37° C. The final molar ratio of collagenase to collagen was 1:5 and the control tube contained type II collagen in the APMA-buffer with no collagenase. The samples were incubated for 20 hours at 30° C. and the collagenase was then inhibited by the addition of EDTA to each tube to a final concentration of 10 mM.

SDS-PAGE of purified collagen was performed using a 7.5%, 1 mm thick, 7 cm×8 cm mini-Protean gel, as described by Dodge and Poole (1). The electrophoresed samples were transferred to a nitrocellulose membrane which was then blocked overnight at 4° C. with PBS containing 3% w/v serum albumin (BSA) (PBS-3% BSA). The membrane was then incubated for 1 hour at room temperature with the COL2-3/4m monoclonal antibody of Example 2 or normal mouse ascitic fluid, each diluted 1 in 100 with PBS-3% BSA. After 3 washes with PBS-0.1% Tween-20, the membrane was incubated for 30 minutes at room temperature with the alkaline phosphatase conjugated goat anti-mouse second-step antibody described above, diluted 1 in 100 with PBS-3% BSA. The membrane was washed well with PBS-Tween and once with distilled water. Alkaline phosphatase substrate solution prepared from a commercial kit (Bio-Rad) was added and incubated with the membrane at room temperature until optimal colour had developed. Further reaction was stopped by washing off the substrate solution with distilled water.

Western blotting analysis confirmed that COL2-3/4m reacts with denatured type II collagen but not with denatured collagen types I, III or X. Antibody COL2-3/4m cross-reacts with the $\alpha_3(XI)$-chain, which is considered to be the same gene product as the $\alpha_1(II)$-chain, although it is more heavily glycosylated (23,24). This cross-reactivity should not interfere with the quantitation of native or denatured type II collagen since there is only one $a_3(XI)$-chain per molecule of type XI collagen, which represents no more than 1% of total collagen α-chains in cartilage (25). The antibody does not cross-react with any other collagen or protein examined. Moreover, the epitope sequence is not present in any other known protein sequence. It did not cross-react with the $\alpha_1(XI)$ or $\alpha2(XI)$-chains (FIG. 4). In a separate immunoblot analysis, the monoclonal antibody was shown to react with the ¾ piece product of collagenase-cleaved type II collagen, but not the ¼ piece product. This confirms that the reactive epitope is on the ¾ piece product of collagenase-cleaved type II collagen.

EXAMPLE 4

Detection of Mouse Antibodies to Synthetic Peptide CB11B and Heat Denatured Type II Collagen Mouse antibodies were tested for reactivity with the synthetic peptide CB11B and with HDC by ELISA according to the following protocol.

HDC was prepared by heating a 1 mg/ml solution of type II collagen for 20 minutes at 80° C. The wells of Immulon-2 ELISA plates (Dynatech) were each coated with 2 μg of synthetic peptide CB11B or HDC, in 50 μl of 0.1M carbonate buffer (pH 9.2), by passive adsorption for 24–48 h at 4° C. The plates were washed three times with PBS containing 0.1% v/v Tween-20 (PBS-Tween) and unreacted sites were blocked by incubation with 50 μl/well of 1% w/v bovine serum albumin (PBS/BSA) for 30 minutes at room temperature. The plates were washed once with PBS-Tween and 50 μl of diluted mouse serum or undiluted hybridoma culture supernatant was added to individual wells. After incubation for 90 minutes at 37° C. the plates were washed three times with PBS-Tween and then alkaline-phosphatase-conjugated goat anti-mouse IgG, IgM and IgA (Zymed) prepared at 1:500 dilution in PBS-BSA-Tween was added at 50 μg/well. The plates were incubated for 90 minutes at 37° C. and then washed three times with PBS-Tween and once with distilled water. Alkaline phosphatase substrate (Sigma) was prepared fresh at 0.5 mg/ml in 9.6% v/v diethanolamine, 49 μg/ml $MgCl_2$, pH 9.8 and incubated in each well for 20–30 minutes at 37° C. The absorbance was measured at 405 nm on a Multiskan plus MKII plate reader (ICN/Flow).

EXAMPLE 5

Inhibition Elisa for Denatured Type II Collagen

A. Assay Procedure

Heat denatured type II collagen (HDC) or standard peptide CB11B or sample to be assayed were incubated with antibody in 96-well round bottom Linbro microtiter plates (Titertek) which were first coated with 100 μl/well of PBS-BSA, as described above. The outermost wells were not used, to minimize the effects of evaporation. There were six non-specific binding (NSB) wells on each plate, which contained 100 μl each of Tris buffer. Fifty μl per well of monoclonal ascitic fluid, diluted appropriately (1 in 5,000–1 in 10,000) with 50 mM Tris, pH 7.6 (Tris buffer) to provide a detectable but inhibitable level of binding was added to 54 wells of the pre-incubation plates. The antibody in 6 of the 54 wells on each plate was mixed with 50 μl/well of Tris buffer, to indicate maximum binding in the absence of inhibitory epitope (MB wells). The antibody in all 48 test wells was mixed with 50 μl/well of standard CB11B peptide or samples containing denatured collagen, diluted appropriately with Tris buffer. All standards and samples were tested in duplicate wells. The plates were sealed with parafilm and incubated overnight at 37° C. in a humidified incubator. A multichannel pipette was used to transfer 50 μl of each pre-incubated sample to the equivalent well of an Immulon-2 ELISA plate, coated with 2 μg/well HDC and blocked with PBS-BSA as described above. It was essential to transfer all the samples from any one plate within a short space of time (about 45 seconds) in order to maximize accuracy. The ELISA plates were each incubated for exactly 30 minutes at room temperature and then washed three times with PBS-Tween. Second antibody and alkaline phosphatase substrate were prepared and added as described above, except that the plates were incubated with the second antibody for 2 hours. The mean of absorbance from the 6 NSB wells was subtracted from the absorbance value of all other wells on the sample plate. The percentage inhibition of binding by samples or standards was calculated relative to the mean absorbance from the 6 MB wells on the same plate, which represented 0% inhibition (100% binding).

B. Characteristics of the CB11B Inhibition ELISA

One sample of HDC was assayed for CB11B 15 times on each of 10 ELISA plates. From this data, the mean coefficient of variation was calculated as 9% for within-plate analysis and 10% for between-plate analysis.

A typical standard curve, plotted as log % inhibition against log CB11B concentration, is shown in FIG. 4. Samples of denatured type II collagen were diluted such that the level of inhibition in the assay fell within the range 20–70%. This represents 0.35–3.5 μg/ml CB11B (approximately 17.5–175 μg/ml denatured type II collagen) in the diluted sample.

Figure 5A:
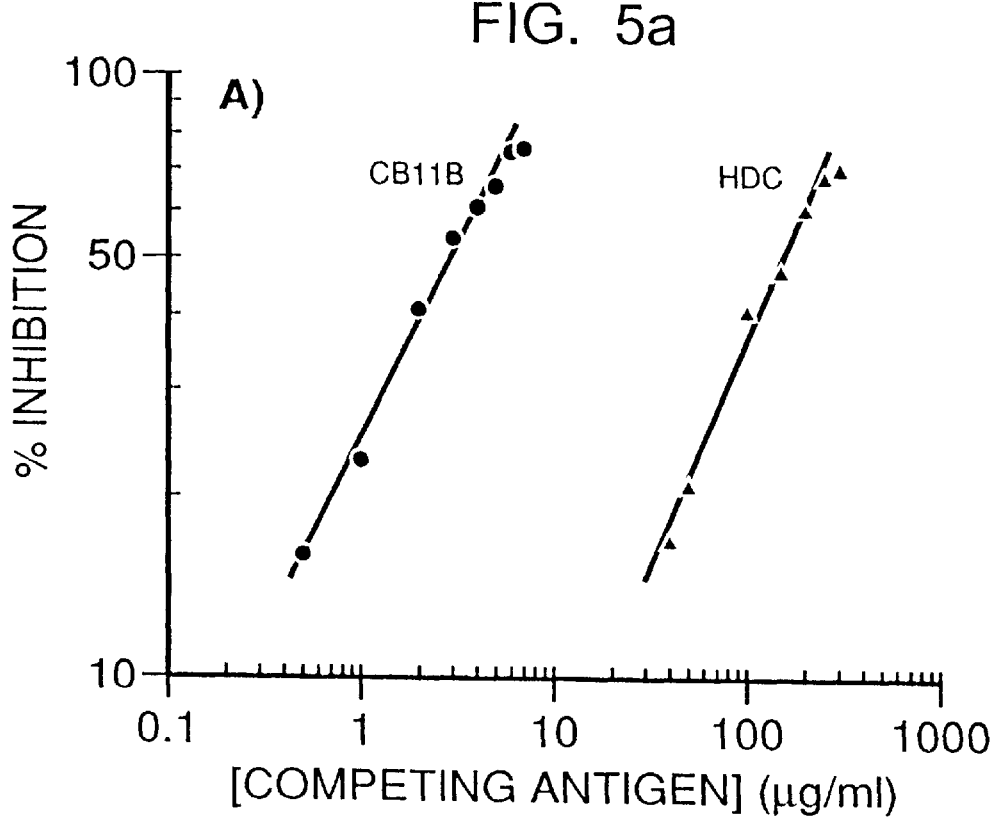
Figure 5B:
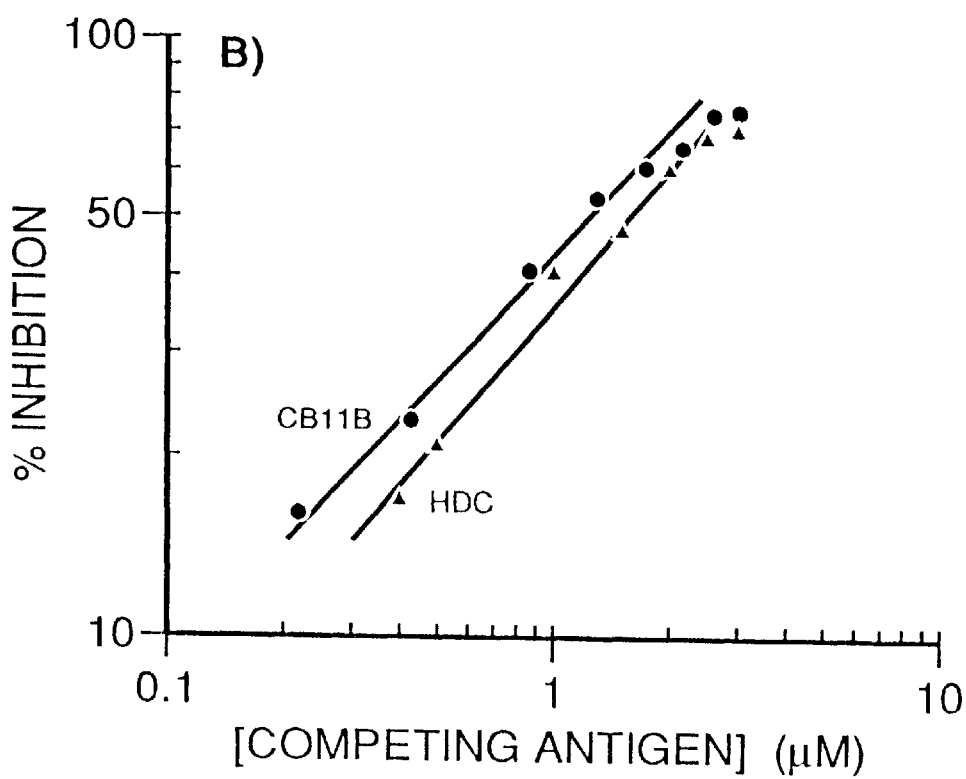

FIG. 5 shows the concentration/response profiles for inhibition in the assay by HDC compared with CB11B. On a μg/ml basis the profiles were parallel (FIG. 5a) and on a molar basis the range of concentrations of antigen producing inhibition were found to be similar for CB11B and HDC (FIG. 5b). Therefore the concentration of CB11B can be used to estimate the concentration of denatured type II collagen, or fragments thereof containing this epitope.

The traditional method of estimating collagen concentrations is on the basis of hydroxyproline content. Therefore, a comparison was made of the concentrations of CB11B and hydroxyproline in different HDC samples. The results (FIG. 6) show a very good correlation between the two methods (r=0.998; p<0.0001).

It was important to demonstrate that the inhibition ELISA did not recognize intact, native type II collagen. The data in FIG. 7 show that when preparations of bovine type II collagen were tested at various concentrations in the native or heat-denatured forms, only the denatured collagen could be detected.

Heat denatured type I and type III collagen were also tested by the above described inhibition ELISA method. Table I provided below shows that heat denatured type I and type III collagens were not detectable in the assay, confirming the finding from Western blotting that COL2-3/4m does not react with type I or type III collagens.

TABLE I

| [HDC] (µg/ml) | [CB11B] BY INHIBITION ASSAY (µg/ml) | | |
| --- | --- | --- | --- |
| | TYPE I HDC | TYPE II HDC | TYPE III HDC |
| 31.25 | 0 | 0 | 0 |
| 62.5 | 0 | 1.53 | 0 |
| 125 | 0 | 2.19 | 0 |
| 250 | 0 | 5.34 | 0 |

EXAMPLE 6

Detection of Type II Collagen in Human Sera and Synovial Fluids Using COL2-3/4m Assay An assay procedure similar to the assay outlined in Example 5 was used to evaluate the presence of collagen II CB11B epitope in sera and synovial fluids (SF) of normal children, children with chondrodysplasias, normal adults and patients with osteoporosis, osteoarthritis and rheumatoid arthritis.

The relative concentrations of the CB11B in sera of normal children (1–12 years) and adults (40–90 years) and in children with chondrodysplasias is shown in FIG. 8. This data indicates relatively high levels of type II cartilage degradation in most children, significantly reduced levels in some adults (39%) but elevated 'childhood' levels in other 'healthy' adults (61%). Hence, the adult levels fall into two categories, one of which is similar to the levels observed in most normal children. In contrast, levels in children with chondrodysplasias, who ordinarily exhibit impaired growth, are generally lower than those found in normal children.

In FIG. 9, relative concentrations of the CB11B epitope in sera from normal adults and patients with osteoporosis (OP), rheumatoid arthritis (RA) and osteoarthritis (OA) are shown. Levels in OP and OA are mostly comparable to those observed in the 'elevated' normal group. In RA a wide variation in levels was observed. It is possible that the 'elevated' normal adult group may exhibit increased cartilage collagen degradation which predisposes to degenerative changes observed in OA. The data also shows that there is a significant increase in cartilage collagen degradation in OP.

FIG. 10 shows the relative concentrations of the CB11B epitope in synovial fluid (SF) and serum of individual patients with rheumatoid arthritis (RA). The levels are always higher in SF. In FIG. 11, relative concentrations of the CB11B epitope in different patients and normal groups in sera and synovial fluids (SF) are shown. The elevations in RA and OA SF over serum levels can be seen.

In order to validate the serum and synovial fluid assay experiments described above, normal human serum (NHS) and sera from patients with rheumatoid arthritis (RA) and osteoarthritis (OA) were diluted and assayed for the presence of the collagen II CB11B epitope. Results shown in FIG. 12 demonstrate that dilution of NHS and sera from patients with RA and OA produces inhibition profiles which exhibit parallelity with inhibition curves for CB11B in the absence of serum. This data demonstrates that the assay of the present invention can be used to quantitate levels of CB11B in sera.

Furthermore, 'spiking' experiments were performed whereby a known amount of denatured collagen was added to normal human sera and rheumatoid sera, following which recovery was measured. Recovery is defined as the sum of collagen CB11B present in the serum and collagen CB11B added. Percentage recoveries (means ± standard deviations of n determinations) were as follows:

RA synovial fluid: 89±20 (n=5)

RA serum: 94±16 (n=5)

normal serum: 85±4 (n=4)

EXAMPLES 7–12

Testing of Biological Tissue

Collagen degradation was also measured in various biological tissues including bovine cartilage discs, bovine cartilage explant cultures and human cartilage using the COL2-3/4m assay. Therefore, a method was developed to extract denatured type II collagen from the tissue in order to use it in the inhibition ELISA assay described in Example 5. The enzyme chymotrypsin was shown to extract unwound collagen from a cartilage sample without degrading the epitope recognized by monoclonal antibody COL2-3/4m. In order to quantitate the amount of unwinding or degradation of collagen in a biological sample, it is necessary to determine the amount of wound collagen in the sample. Therefore, once the unwound collagen was extracted from the samples, the samples were treated with proteinase K to solubilize and unwind remaining native collagen which could also be measured using the inhibition ELISA described in Example 5.

Before using the enzymes chymotrypsin and proteinase K on biological tissues, it was first determined that these enzymes did not cleave the epitope recognized by the monoclonal antibody COL2-3/4m.

EXAMPLE 7

Proteolytic Cleavage of HDC by Chymotrypsin and Proteinase K

Aliquots of HDC at a concentration of 0.25 mg/ml were prepared in Tris buffer containing 0.5 mg/ml of α-chymotrypsin or proteinase K (both from Sigma). Control tubes contained only 0.25 mg/ml HDC, or 0.5 mg/ml chymotrypsin or 0.5 mg/ml proteinase K. The samples were all incubated overnight at 37° C. and then boiled for 10 minutes to inactivate the proteases. Degradation of the HDC by each protease was confirmed by SDS-PAGE. The degraded collagens and control samples were each tested for reactivity in the inhibition ELISA using monoclonal antibody COL2-3/4m.

As shown in Table II below, digestion of HDC with either chymotrypsin or proteinase K had no effect on its reactivity in the inhibition ELISA.

TABLE II

| COMPETING ANTIGEN | [CB11B] by inhibition assay (μg/ml) |
|---|---|
| 250 μg/ml HDC | 5.0 |
| 250 μg/ml HDC + 500 μg/ml CHYMOTRYPSIN | 5.7 |
| 250 μg/ml HDC + 500 μg/ml PROTEINASE K | 6.0 |

This indicates that the CB11B epitope is not cleaved by these proteases. The inhibited proteases themselves did not have any inhibitory activity in the assay. Since chymotrypsin, like all mammalian proteases apart from collagenase, cannot cleave intact, triple helical collagen, as confirmed by the data in Table III this enzyme can be used to selectively degrade and solubilize any collagen in cartilage which has already been unwound in situ. Conversely, cartilage can be fully solubilized by incubation with proteinase K at 56° C. (its optimal temperature) and the extracted collagens can then be completely unwound by heat denaturation.

TABLE III

| | [CB11B] BY INHIBITION ASSAY (μg/ml) | | | |
|---|---|---|---|---|
| [COLLAGEN] (μg/ml) | HDC | HDC + 500 μg/ml CHYMOTRYPSIN | NC | NC + 500 μg/ml CHYMOTRYPSIN |
| 62.5 | 1.27 | 1.55 | 0.2 | 0 |
| 125 | 2.1 | 2.2 | 0 | 0 |
| 250 | 5.8 | 6.6 | 0.1 | 0 |

EXAMPLE 8

Assay of Cartilage Discs for Denatured Collagen Using COL2-3/4m Assay

A. Preparation of Cartilage Discs

Bovine foetal epiphyseal cartilage was obtained from the proximal tibiae of fetuses, determined to be 200–250 days old as described by Pal et al (8), shortly after the sacrifice of pregnant cows at a local slaughter house. A stainless steel cork borer was used to make full-depth plugs of cartilage with a diameter of 6 mm. The plugs were placed in a custom-made tissue slicer, designed to make reproducible discs of tissue, each 1 mm thick, using a razor blade. Discs were cut from the growth plate fracture face of the physis with the metaphysis through to the articular surface (a total depth of 7 mm) and the relative position of each one was noted. A single disc of 4.8 mm diameter was taken from each of the larger ones using the appropriate-sized borer. The resulting 1 mm×4.8 mm discs were weighed prior to tissue culture or extraction with proteases: the approximate mean weight was 30 mg. Parallel plugs were used for the preparation of histological sections so that growth plate, epiphyseal cartilage and articular cartilage could each be accurately located.

B. Extraction of Denatured Collagens from Cartilage

Freshly isolated or cultured discs of bovine foetal epiphyseal cartilage were distributed into Eppendorf tubes. To each tube was added 0.5 ml of 1 mg/ml α-chymotrypsin in Tris buffer containing 1 mM iodoacetamide, 1 mM EDTA and 10 μg/ml pepstatin-A. The samples were incubated overnight at 37° C. and the chymotrypsin was then inhibited by addition of 200 μl per tube of 0.4 mg/ml N-tosyl-L-phenylalanine chloromethyl ketone (TPCK) in Tris buffer containing 4% v/v ethanol. The samples were centrifuged and the chymotrypsin extract was separated from the tissue residues. Each residue was then digested with 0.5 ml of 1 mg/ml proteinase K in Tris buffer containing the same protease inhibitors as described above. After digestion overnight at 56° C., no residue remained. The proteinase K was inactivated and the extracted collagen fully unwound by boiling the samples for 10 minutes. In order to measure any wound collagen extracted by chymotrypsin, 300 μl of each chymotrypsin extract was mixed with 100 μl of the 1 mg/ml proteinase K solution and incubated and then inhibited as described for cartilage residues. Extracts were stored at 4° C. prior to assay for denatured collagen.

The samples prepared above were assayed for denatured collagen according to the assay described in Example 5. The results are shown in FIG. 13. FIG. 13 shows the percentage denatured (unwound) collagen in serial 1 mm thick discs starting from the junction (fracture face) of the hypertrophic zone of the growth plate with the metaphysis (0–1 mm) and extending through the epiphyseal cartilage into superficial articular cartilage (6–7 mm). An elevation in the proportion of unwound type II collagen is observed in the hypertrophic zone, compared to other cartilages.

EXAMPLE 9

Assay of Cartilage Explant Cultures for Denatured Collagen Using COL2-3/4m Assay Cartilage discs were cultured in serum-free Dulbecco's modified Eagles medium (DMEM). The freshly isolated cartilage discs were individually washed 3 times with DMEM containing 5 μg/ml Fungizone (Flow laboratories) and once with regular DMEM. The discs were distributed into the wells of 48-well tissue culture plates (Costar). Discs cut from a defined distance from the growth plate fracture face were used. Each well contained one disc in 500 μl DMEM. Ascorbate was added to all cultures at a final concentration of 50 μg/ml. Where indicated recombinant human IL-1β (Upjohn) was added at 200 U/ml, together with 1 mg/ml of bovine serum albumin (BSA;Sigma). Control wells received only BSA and ascorbate. The explants were cultured for 6 days at 37° C. in an atmosphere of 5% $CO_2$/air. Media were changed every 2 days with the addition of fresh IL-1β as necessary. The media and cartilage discs were stored at −20° C. prior to extraction or immunohistochemical analysis. Media samples or tissue extracts were assayed for denatured (unwound) and total type II collagen as described for the cartilage discs in Example 8.

EXAMPLE 10

Detection of Type II Collagen Degradation in Human Cartilage Using COL2-3/4m Assay The purpose of this study was to analyze type II collagen denaturation (unwinding) in whole depth samples resulting from in vivo cleavage in human femoral condylar articular cartilages. Normal and osteoarthritic (OA) persons were studied.

Cartilage discs, prepared as described in Example 8, were routinely extracted, first with chymotrypsin and then with proteinase K, as described in Example 8. Levels of denatured (unwound) type II collagen were estimated by measuring CB11B in the chymotrypsin extract. Extraction of intact (wound, native) type II collagen by chymotrypsin was determined by measuring CB11B in the proteinase K-digested chymotrypsin extract and subtracting from this value the amount of CB11B extracted by chymotrypsin and immunoreactive in an unwound form. That the chymotrypsin extracts may contain some wound collagen is shown in Table IV. Here the chymotrypsin extract has also been treated with proteinase K to unwind any helical collagen. In human adult cartilages, this amount was low (2.8–3.3% of the total chymotrypsin extractable type II collagen) but in foetal bovine articular cartilage and growth plate it could vary between 7.1 and 24.3% of the total chymotrypsin extractable collagen. These results demonstrate the importance of treating the chymotrypsin extract with proteinase K to distinguish between unwound and wound collagens.

Total type II collagen was estimated by measuring CB11B in the proteinase K-digested residue (after initial chymotrypsin extraction) and adding to this value the amount of CB11B (wound and unwound) extracted by chymotrypsin. Results are shown in FIG. 14 which represents the amount of denatured (unwound) collagen as a percentage of the total collagen present in femoral condylar cartilages where each bar represents one patient. Six specimens (A to F) were taken from normal patients and twelve specimens (A to L) were taken from osteoarthritic patients. There was no denaturation found in specimen B. An increase in collagen denaturation above the highest normal value was observed in 8 of 12 OA patients. The TPCK-inhibited chymotrypsin and boiled proteinase K were found to have no inhibitory effect themselves in the CB11B inhibition ELISA.

TABLE IV

| TISSUE TYPE | NATIVE TYPE II COLLAGEN IN CHYMOTRYPSIN EXTRACT (% OF TOTAL CHYMOTRYPSIN-EXTRACTABLE TYPE II COLLAGEN) | | |
| --- | --- | --- | --- |
| | NUMBER OF SAMPLES | MEAN % | RANGE |
| NORMAL ADULT HUMAN CARTILAGE | 6 | 2.8 | 0–10.9 |
| OSTEOARTHRITIC HUMAN CARTILAGE | 23 | 3.3 | 0–34.6 |
| BOVINE GROWTH-PLATE CARTILAGE | 6 | 24.3 | 0–50 |
| BOVINE FOETAL ARTICULAR CARTILAGE | 6 | 7.1 | 0–22.9 |

EXAMPLE 11

Type II Collagen Degradation in Osteoarthritis

To study damage to type II collagen in articular cartilage in arthritis, we developed an immunoassay using COL2-3/4m based on our earlier experiments described above. In this example, we describe and use this assay to provide the first quantitative evidence for increased damage to type II collagen in situ and decreased content of total type II collagen in OA cartilage. Until we developed this new methodology, unwinding of the triple helix of type II collagen could not be detected in situ.

Tissue

Human articular cartilages were removed from the anterior (loaded) region of the femoral condyles of adult knee joints. OA cartilages were obtained at surgery from patients undergoing total joint arthroplasty. Site-matched nonarthritic articular cartilages of normal appearance were obtained at autopsy within 15 h postmortem from individuals with no known history, nor signs, of arthritic/joint abnormalities. Patient details and Mankin grades of the normal and OA cartilage specimens are shown in Table V. Previously, cartilage from these same sites have been analyzed for the proteoglycan aggrecan (9).

Preparation of Cartilage Plugs

Since cutting cartilage can produce denaturation of type II collagen, care was taken to prepare defined plugs of cartilage using a specially made, standardized, stainless steel punch according to the method described in Hollander et al (46). Wherever possible, a full depth slice of cartilage was taken from each femoral condyle (medial and lateral) and 2 full-depth cylindrical plugs, each approximately 4 mm diameter×2 mm deep, were prepared from each slice using the steel punch. One of the plugs was used for the histological assessment of Mankin grade, as previously described (9,10). This did not include analysis of the calcified cartilage, hence the maximum grade in the group of OA cartilages was only 10. The other plug was used for the extraction and assay of type II collagen. In some experiments the full depth plugs were approximately divided into an upper and a lower half using a scalpel. The upper 1 mm included the articular surface and upper-mid zone whilst the lower 1 mm consisted of lower-mid and deep zone cartilage.

Extraction and Assay of Native and Denatured Collagen from Cartilage Plugs

Cartilage plugs were routinely extracted, first with α-chymotrypsin and then proteinase K as described above in Example 8B. The TPCK-inhibited α-chymotrypsin and boiled proteinase K had no inhibitory effect themselves in the inhibition ELISA.

Determination of Type II Collagen Content Based on Epitope Analysis

The molecular weights of the human type II collagen α-chain and of peptide a (II)-CB11B were each calculated from their amino acid sequences using version 1.00 of Prosis software (Hitachi Software Engineering Co. Ltd., USA). It was assumed that there are 99 hydroxyproline residues and 20 hydroxylysine residues for every 1000 total residues of the $\alpha_1$(II)-chain (21). On this basis, the molecular weights of the $\alpha_1$(II)-chain and $\alpha_1$(II)-CB11B peptide were calculated as 98,291 and 2,231 respectively. Therefore, the µg/mg concentration of type II collagen extracted from cartilage was calculated by multiplying the concentration of extracted $\alpha_1$(II)-CB11B by a factor of 44.

Statistical Analysis

Significance of differences in total and denatured collagen was tested using the Mann-Whitney U-test for comparison between groups and the paired t-test for comparison of upper 1 mm with lower 1 mm zones prepared from the same cartilage plugs.

Total Type II Collagen Content and Content of Denatured Type II Collagen in Full-Depth Samples of Human Femoral Condylar Cartilages The mean type II collagen concentration for the normal cartilages was 139.5 µg/mg. Thus for normal cartilage the total type II collagen accounts for a mean (range) of 14.0% (9.2–20.8%) of the wet weight of the tissue. For OA cartilage the equivalent mean (range) value was 10.3% (7.4–15.0%). The total amount of type II collagen/mg wet weight was significantly decreased in OA compared to normal cartilage.

The proportion of denatured type II collagen was significantly increased in OA compared to normal cartilage. The mean values for % denatured collagen in normal and OA cartilages were 1.1% and 6.0% respectively.

There were no correlations between either total or % denatured type II collagen and the degree of cartilage degradation recorded as the Mankin grade of OA cartilages.

In the present study we show that damage to type II collagen, measured as denaturation (unwinding) of the triple helix, is detectable in adult human femoral condylar cartilage and is increased in OA cartilage. This damage in OA is accompanied by a net reduction in the total type II collagen content. Previously, a loss of tensile properties was observed in OA cartilage, indicative of damage to type II collagen (12–14). The present studies reveal that the reduced tensile strength in part relates to damage to the triple helix of type II collagen leading to denaturation (unwinding). It also correlates with a net loss of this molecule in OA, previously indicated by a reduction in total cartilage collagen content measured as hydroxyproline (19). In contrast, this loss of collagen is not observed in RA femoral condylar cartilage, although there is a similar increase in type II collagen denaturation to that observed in OA (50).

Variation in Total and Denatured Type II Collagen with Depth of Cartilage

From cartilage in which specimens could be obtained (minimum thickness, 2 mm), plugs were divided into the upper 1 mm (articular zone) and lower 1 mm (deeper zone; these are approximate thicknesses) using a scalpel and a specially constructed slicing bed. The total type II collagen concentration was higher in the deeper (lower 1 mm) compared to more superficial (upper 1 mm) cartilage for 4 of 5 normal and 5 of 8 OA specimens. The % denatured collagen did not vary significantly with depth in normal cartilage. In one sample there was a high level of denatured collagen in the more superficial cartilage and increased denaturation in the deeper cartilage too. In 2 of the 4 other specimens, denaturation was enhanced in the more superficial cartilage, otherwise it was similar in each zone or higher in the deeper cartilage. For OA cartilage the % denatured collagen was significantly higher in the upper 1 mm zone. This difference was seen in 6 of 8 specimens. Of the other 2 specimens one showed the opposite trend and the other exhibited similar denaturation in the upper and lower levels. There was no correlation between total or % denatured collagen in either the upper or lower zones and Mankin grade of the full-depth cartilage for normal and OA specimens (data not shown). The mean values of total and denatured collagen in the upper and lower 1 mm zones are shown in Table VIII, for comparison of each zone in OA with the same zone in normal cartilage. In OA, total collagen content was only significantly reduced in the deeper cartilage of OA compared to normal. Similarly, type II collagen denaturation was only significantly increased in the lower zone of OA compared to normal cartilage. This result is probably due to the fact that denaturation in the upper zone was very variable within the normal group (one specimen in particular), which may reflect early, pre-clinical, OA like changes in normal cartilage. Indications from preliminary studies are that there is less denaturation in younger (skeletally mature) cartilages, suggesting that type II collagen denaturation may in part be a function of ageing. This may lead to excessive degenerative changes in some cases (A. Hollander, T. Heathfield and A. R. Poole, unpublished observations). In separate immunohistochemical studies with monoclonal antibody COL2-3/4m we confirm that denaturation in normal and OA cartilages usually starts at and close to the articular surface and progressively extends down into the cartilage with increasing Mankin grade (50). The differences in % denatured collagen in either region were not as marked as the changes seen in full-depth plugs. However it should be noted that for the depth-study, cartilage was taken from the thickest region of OA tissue and this may have been less degraded than cartilage from the thinner tissue sites.

EXAMPLE 12

Digestion of Extracted Collagen with Clostridial Collagenase

It was important to demonstrate that inhibition observed in the al (II)-CB11B ELISA by α-chymotrypsin and proteinase K extracts of human cartilage was due entirely to the $\alpha_1$(II)-CB11B epitope. Since the epitope is destroyed by treatment with clostridial collagenase (see above and Table VI), some extracts were treated with this enzyme as a control for specificity.

Proteolytic Cleavage of HDC and $\alpha_1$(II)-CB11B Peptide by Clostridial Collagenase HDC and $\alpha_1$(II)-CB11B were dissolved in Tris containing 5 mM $CaCl_2$ and 14 U/ml chromatographically purified collagenase form III (bacterial collagenase) from Clostridium histolyticum (Advance Biofactures Corp., Lynbrook, N.Y.). Controls contained HDC or $\alpha_1$(II)-CB11B in Tris with 5 mM $CaCl_2$ but no collagenase, or collagenase in Tris with 5 mM $CaCl_2$ but no HDC, nor $\alpha_1$(II)-CB11B peptide. All the tubes were incubated overnight at 37° C. and the collagenase was then inhibited by the addition of EDTA to a final concentration of 0.1M. The samples were each tested for reactivity in the inhibition ELISA for denatured type II collagen.

Digestion of Extracted Collagen Peptides with Clostridial Collagenase to Confirm Susceptibility of the Extracted CB11B Epitope to Cleavage by this Enzyme Collagens were extracted from plugs of OA cartilage with α-chymotrypsin and proteinase K and the proteinases inhibited as described above. The extracts were each divided into two aliquots. To one of these was added 5 mM $CaCl_2$ and 14 U/ml clostridial collagenase and to the other, 5 mM $CaCl_2$ only. A control tube contained collagenase in Tris with 5 mM $CaCl_2$ but no cartilage extract. All tubes were incubated overnight at 37° C. and the collagenase activity was inhibited with EDTA as described above. The samples were all tested for reactivity in the inhibition ELISA for denatured type II collagen.

Epitope in Peptide $\alpha_1$(II)-CB11B is Cleaved by Clostridial Collagenase

When clostridial collagenase alone was inhibited with 100 mM EDTA and assayed for $\alpha_1$(II)-CB11B it produced a small amount of inhibition, equivalent to a background level of 0.85 μg/ml $\alpha_1$(II)-CB11B (Table VI). This inhibition was probably due to cleavage of some of the HDC bound to the ELISA plate, by residual clostridial collagenase activity. HDC or $\alpha_1$(II)-CB11B alone incubated in Tris with $CaCl_2$ at 37° C. for 24 h produced good inhibition in the assay for $\alpha_1$(II)-CB11B, but the amount of $\alpha_1$(II)-CB11B detected was reduced to the background level when HDC or $\alpha_1$(II)-CB11B were treated with clostridial collagenase (Table VI), demonstrating hydrolysis of the epitope by clostridial collagenase. Therefore this property can be used to confirm the identity of the epitope in ELISA inhibition assays of samples containing it.

There was a loss of immunoreactivity in each case (Table VII), demonstrating the specificity of the assay for the $\alpha_1$(II)-CB11B epitope in the cartilage extracts.

EXAMPLE 13

Guanidinium Chloride Extracts of OA Cartilage

In order to determine if the type II collagen extracted from cartilage by α-chymotrypsin was mostly derived from fibril-associated, cross-linked collagen or from non-fibrillar, non-cross-linked α-chains, a comparison was made of extraction by α-chymotrypsin and 4M guanidinium chloride. The latter is a chaotropic reagent which can only extract the non-fibrillar, non-cross-linked collagen molecules. Adjacent plugs of cartilage from 5 OA patients were extracted with α-chymotrypsin or guanidinium chloride. Far less type II collagen was extracted with 4M guanidinium chloride than with α-chymotrypsin. For the 5 OA specimens examined the mean ± SD (total native+denatured) type II collagen extracted by guanidinium chloride and α-chymotrypsin was 0.019±0.003 and 0.164±0.012 μg/mg wet weight respectively. Therefore the amount of type II collagen extracted by 4M guanidinium chloride is 11.6% of that extracted by α-chymotrypsin, suggesting that most of the denatured material extracted with α-chymotrypsin is derived from cross-linked fibrils rather than a pool of newly synthesized, non-cross-linked α-chains or peptides thereof. Of the type II collagen extracted with guanidinium chloride or α-chymotrypsin, only a small proportion (10.5% and 7.3% respectively) was native collagen (detected after digestion with proteinase K). However, we have found that incubation of purified native type II collagen for 72 h at 4° C. in 4M guanidinium chloride, followed by dialysis into Tris, causes over 90% of the collagen to denature, as judged by assaying for $\alpha_1$(II)-CB11B (data not shown). Therefore, it is likely that most of the $\alpha_1$(II)-CB11B extracted with guanidinium chloride is contained within newly synthesized molecules that are denatured by the extraction procedure. If the guanidinium chloride extractable pool represents denatured, newly synthesized collagen then the amount of this which is present in the cartilage accounts for a very small proportion of the denatured collagen.

Extraction of Cartilage Plugs with Guanidinium Chloride to Determine the Content of Non-Cross-Linked Collagen In one experiment, two adjacent full-depth plugs were taken from each of 5 OA cartilages. One of the plugs from each specimen was extracted with α-chymotrypsin as described above. The other plug from each specimen was extracted for 72 h at 4° C. with gentle rocking in 4 mM guanidinium chloride, 0.1M Tris-HCl, pH 7.3 containing 1 mM iodoacetamide, 1 mM EDTA and 10 μg/ml pepstatin-A. The guanidinium chloride extracts were dialysed exhaustively against Tris using membrane with a molecular weight cut-off of 3,500. A 300 μl aliquot of each of the α-chymotrypsin and guanidinium chloride extract was mixed with 100 μl of 1 mg/ml proteinase K, incubated overnight at 56° C. and then boiled to inhibit the proteinase. All the extracts were tested for reactivity in the inhibition ELISA for denatured type II collagen.

EXAMPLE 14
Location of $\alpha_1$(II)-CB11B on Cyanogen Bromide Peptide CB11

Since the $\alpha_1$(II)-CB11B epitope amino acid sequence only occurs in the CB11 peptide of type II collagen, the antibody should only recognize CB11. Cleavage of type II collagen with cyanogen bromide produced a number of peptides, including CB8, CB10 and CB11, as seen by SDS-PAGE and silver staining. The only peptide detected by immunoblotting with monoclonal COL2-3/4m was, as expected, based on the location of the epitope, CB11.

EXAMPLE 15
Enhanced Damage to Type II Collagen in Normal Adult Human L5-S1 Intervertebral Discs Compared to Articular Cartilage From Same Individuals Although there is histological evidence of collagen degradation in ageing intervertebral discs, these changes have not previously been quantitated, nor compared to articular cartilages. There are 23 intervertebral discs in the adult human spine and each one is structurally characterized by 2 integrated tissues: the nucleus pulposus (NP) and the annulus fibrosus (AF). There is good documentation of the gross morphological changes in the intervertebral disc with age and in disease, including the formation of splits and clefts in the NP, tearing of the AF, marginal osteophyte formation and an overall thinning of the disc which is seen as a loss of disc height (27,28). Histological changes have also been observed, including a loss of staining for proteoglycan and increased damage to collagen fibrils (29). However, biochemical analyses of these changes have been limited to a few studies in which total content of water, collagen and proteoglycan (31,31), or the relative proportion (32) and distribution (33) of different collagens, have been measured. In human intervertebral disc, the NP contains collagen types II, VI and XI whilst the AF contains collagen types I, II, III, V, VI and XI (34). Type IX collagen is found in the AF and NP of intervertebral disc from some species, but has not been reported in human disc tissue (33). We used the COL2-3/4m immunochemical assay to measure the content of denatured and total type II collagen in macroscopically normal adult annulus fibrosus (AF) and nucleus pulposus (NP) of the L5-S1 intervertebral disc and in macroscopically normal articular cartilage obtained at autopsy from 7 individuals, including 1 male and 6 females, aged 33–76 years.

Sources of Tissues

Human knee articular cartilage and intervertebral disc tissue were obtained at autopsy (within 15 h post-mortem) from 7 adults who were without macroscopic signs of arthritic/joint/spinal abnormalities. Table IX shows the age, sex and cause of death of each individual.

Full-depth specimens of articular cartilage were taken from the anterior (loaded) region of the femoral condyles (medial and lateral compartments) of each individual. Specimens of the L5-S1 intervertebral disc from the same individuals were obtained by removing a wedge-shaped block of tissue from the anterior region of the AF, extending into the NP. The disc specimens all had normal gross morphology for their age and were classified as grades II or III (out of a maximum of V) by the morphological grading system of Thompson et al (27). All tissue samples were wrapped in plastic immediately after collection to maintain humidity and they were maintained at room temperature prior to immediate processing and weighing.

Preparation of Tissue

Three full depth adjacent blocks of tissue, each approximately 3 mm×5 mm, were cut from the articular cartilage and from standardized regions of the AF and NP specimens using a scalpel. The wet weight of each block of tissue was immediately recorded. Extraction of collagens was initiated without storage. One block from each tissue site was used for the extraction of denatured and native type II collagens and the subsequent assay of the $\alpha_1$(II)-CB11B epitope and of hydroxyproline. A second, adjacent block was used for the extraction and assay of proteoglycans and the third block was prepared for immunohistochemical analysis of denatured type II collagen.

Extraction Of Denatured And Native Type Ii Collagens and Determination of Total Type II Collagen Content Tissue blocks (30–40 mg wet weight) were routinely extracted, first with α-chymotrypsin (to solubilize denatured collagen) and then proteinase K (to digest remaining native collagen α-chains), as described above in Example 8B. The TPCK-inhibited α-chymotrypsin and boiled proteinase K had no effect on the immunoassay.

The tissue extracts were assayed for hydroxyproline by a calorimetric method (40). The total collagen content (all types) was estimated on the basis that the hydroxyproline content of the collagens is equivalent to 10% of the weight of each α-chain (41).

Tissue extracts were assayed for denatured collagen as previously described in the above examples, using the $\alpha_1$(II)-CB11B peptide as a standard. Briefly, the samples were preincubated with antibody COL2-3/4m overnight at 37° C., transferred to ELISA plates coated with heat denatured type II collagen and incubated for a further 30 min at room temperature. Inhibition by the samples of antibody-binding to the heat denatured collagen was detected using an alkaline phosphatase labelled goat anti-mouse immunoglobulin second-step antibody and alkaline phosphatase substrate.

The total type II collagen content of each tissue specimen was calculated on the basis of the measured concentration of $\alpha_1$(II)-CB11B, as previously described.

Extraction and Assay of Proteoglycans

Blocks of tissue were distributed individually into Eppendorf tubes and digested directly with proteinase K, as described above. Aliquots of the digested tissues were assayed for glycosaminoglycans by a micro-colorimetric assay using dimethylmethylene blue, as previously described (41).

Immunohistochemistry

Tissue blocks were mounted in OCT embedding media (Miles Laboratories, Naperville, Ill.), frozen and 6 μm thick sections were cut at −20° C. using a Tissue-Tek II cryostat (Miles Laboratories). Sections were picked up on glass microscope slides precoated with aminoalkylsilane as described by Henderson (42), to ensure complete adherence of the tissues sections to the slides. This is very important in these studies since the COL2-3/4m monoclonal antibody will detect denatured type II collagen at the surfaces or edges of the section. Thus complete adherence is essential to ensure uniformity of immunoreactivity.

Sections were either immediately frozen and stored at −20° C. or used immediately. Similar results were obtained in either case. The sections were fixed for 5 min in 4% formaldehyde, freshly prepared from paraformaldehyde in phosphate buffered saline (PBS) (43) and washed in several changes of PBS for 15 min. These and subsequent manipulations were at room temperature. Unreactive aldehyde groups were blocked with 1% w/v normal pig serum in PBS for 15 min. Endogenous peroxidase activity was blocked by incubation of the sections with freshly prepared 0.5% v/v $H_2O_2$ in absolute methanol for 10 min followed by washing in PBS for 15 min. To enhance permeability of the tissue, sections were treated with chondroitinase ABC (ICN/Flow, Mississauga, ON) at 0.0125 U/50 μl per section in 0.1M Tris-acetate buffer, pH 7.6, for 90 min at 37° C. in a humidified environment to remove chondroitin sulfate (44). After washing in PBS for 15 min the sections were incubated with 0.2M EDTA in 50 mM Tris, pH 7.6 for 1 h at room temperature in order to ensure removal of any calcific deposits in the specimens. They were then washed for 15 min with PBS containing 0.1% w/v BSA.

Sections were incubated for 30 min at room temperature in a humidified chamber with 50 μl/section of monoclonal antibody COL2-3/4m ascitic fluid (diluted 1/100) or control, non-immune ascitic fluid, each diluted in PBS containing 1% w/v BSA. An additional specific control was prepared by absorbing monoclonal antibody COL2-3/4m before use with 100 μg/ml of peptide a1(II)-CB11B, or an unrelated peptide of the same length and concentration, at 37° C. for 1 h and centrifugation before use to remove any precipitate. Sections were washed 3 times for 10 min each with PBS containing 0.1% w/v BSA. A biotin-streptavidin detection system (Amersham Corp., Arlington Heights, Ill.) was used consisting of pig F(ab')$_2$ anti-mouse Ig labelled with biotin and peroxidase-conjugated streptavidin as the indicator. The biotinylated pig anti-mouse F(ab')$_2$ (prepared and labelled in this laboratory) was used at a dilution of 1/20 in PBS with 1% w/v BSA at 50 μl/section for 30 min. After washing with azide-free PBS, the sections were treated with 50 μl/section of the peroxidase-conjugated streptavidin at a dilution of 1/150 in azide-free PBS with 1% w/v BSA for 20 min at room temperature. The sections were washed twice for 10 min in azide-free PBS, post-fixed by incubating with 2% v/v gluteraldehyde in azide-free PBS and then stored in 50 mM Tris, pH 7.6, for 24 h. The peroxidase reaction was performed with copper-$H_2O_2$/silver intensification of the nickel-diaminobenzidine end-product of the peroxidase reaction, as previously described (45).

Statistical Analysis

Significance of differences in the content of collagen, hydroxyproline and proteoglycan in the AF and NP compared to paired cartilage from each individual case were treated using the 2-tailed paired t-test. Correlations were made using spearman rank regression analyses.

Contents of Total Type II Collagen and Hydroxyproline

The total type II collagen content determined by the $\alpha_1$(II)-CB11B assay and expressed as μg/mg wet weight of tissue was significantly lower in both the AF and NP than in the articular cartilage and the same trend was noted in all 7 cases. The mean (SD) values for cartilage, AF and NP were 188.3 (36.5) μg/mg, 94.8 (21.6) μg/mg and 82.5 (26.9) μg/mg respectively. Surprisingly, the total type II collagen concentration in the AF was not significantly different from the NP.

The hydroxyproline content expressed as μg/mg wet weight of tissue was also significantly lower in both the AF and NP compared to the cartilage. There was a trend towards higher levels of hydroxyproline in the AF than in the NP, seen in 6 of 7 cases, but this difference was not significant. The mean (SD) values for cartilage, AF and NP were 20.1 (1.0) μg/mg, 15.0 (3.2) μg/mg and 10.9 (4.6) μg/mg respectively.

The ratio of μg type II collagen:μg hydroxyproline was lower in the AF than in the cartilage of all 7 cases and this difference was significant, demonstrating that a significant proportion of collagen in the AF is not type II. In contrast, there was no significant difference in this ratio in the NP compared to cartilage. The mean (SD) values for cartilage, AF and NP were 9.4 (1.9), 6.4 (0.70) and 8.2 (3.0) respectively. Assuming that the hydroxyproline content of the fibrillar collagens is 10% of the weight of each α-chain (14), the ratios indicate that type II collagen accounts for approximately 82% of the total collagen in NP, but only 64% of total collagen in the AF of the L5-S1 intervertebral disc, whereas in the articular cartilage type II collagen represents 94% of the total collagen content. This data is similar to that of Eyre and Muir, who found that in the adult human intervertebral disc over 85% of the collagen in NP was type II and in articular cartilage over 95% was type II, whereas in AF type II collagen represented 50–65% of total collagen (32).

These results show that although the absolute concentration of type II collagen is essentially the same in the AF as in the NP, its proportion relative to other collagens varies. Therefore, the previously reported differences in the ratio of type I to type II collagens in these 2 regions of the disc (32) must be accounted for by a higher content of type I collagen rather than a lower content of type II collagen in the AF.

Contents of Denatured Type II Collagen in Cartilage and Intervertebral Disc

The % denatured type II collagen content determined by the α1(II)-CB11B assay was always higher in both the AF and NP than in the corresponding articular cartilage of all 7 cases (A–G). As a group, these differences were significant (p<0.01). There was no significant difference in the content of denatured type II collagen in the AF compared to NP. More denaturation was noted in the AF than the NP in 3 of the cases, the reverse trend in 1 case and similar levels of denaturation in the AF and NP in 3 cases. The mean (SD) values for cartilage, AF and NP were 1.6(1.0)%, 5.1(6.6)% and 3.6(1.7)% respectively. These results clearly show that type II collagen in adult, morphologically normal L5-S1 intervertebral disc (AF and NP) is more damaged than in the articular cartilage of the same individual.

Contents of Type II Collagen Relative to Proteoglycans

The proteoglycan content, measured as GAG and expressed as μg/mg wet weight of tissue, was significantly higher in the NP than in the articular cartilage of all 7 cases and this difference was significant. There was no significant difference in the GAG content of the AF compared to cartilage. The mean (SD) values of GAG content for cartilage, AF and NP were 48.4(13.3) μg/mg, 58.3(12.0) μg/mg and 80.2(19.5) μg/mg respectively. This data is in agreement with previous studies showing a higher proteoglycan concentration in the NP than the AF (26).

Correlations between the concentrations of type II collagen and GAG indicated that there was no significant trend in this relationship in either cartilage (r=0.41, NS) or AF (r=0.68, NS). However, in NP there was a significant trend towards lower concentrations of type II collagen in specimens with a low concentration of proteoglycan (r=0.78, p<0.05). The results show that although these intervertebral discs all had a normal gross morphology (see above), some of them nevertheless exhibit biochemical signs of matrix deterioration, demonstrated as a loss of proteoglycan accompanied by a loss of type II collagen in the NP.

Immunohistochemistry

Staining of the articular cartilage with monoclonal antibody COL2-3/4m was either absent or limited to diffuse staining in the superficial zone. In contrast, there was intense staining throughout the matrix and in pericellular regions of both the AF and NP. Specimens treated with non-immune ascitic fluid or COL2-3/4m pre-absorbed with peptide α₁(II)-CB11B showed minimal staining.

Using newly developed methodology we show here, for the first time, that the damage to type II collagen in morphologically normal adult human L5-S1 intervertebral disc is significantly greater than in paired, normal articular cartilage. This may have relevance to the degenerative changes which are commonly observed in the intervertebral disc with ageing. The increased denaturation of type II collagen in the disc was similar to the damage seen in articular cartilage from patients with osteoarthritis or rheumatoid arthritis (46), suggesting that there is considerable potential for collagen degradation in clinically normal adult disc. Damage was much more pronounced in some discs than in others and in some cases the damage was more pronounced in the AF than in the NP. The extensive damage revealed by immunohistochemical staining with monoclonal antibody COL2-3/4m throughout the AF and NP also contrasts to the more limited and restricted staining seen in articular cartilage.

We also show that the lower proportion of type II collagen relative to other collagens in the AF, demonstrated here and previously (32), is probably due to a higher content of type I collagen in the AF, in view of the similar type II collagen contents in the AF and NP. Absolute concentrations of each collagen have not previously been measured and so there is no data available to indicate if the observed differences in the relative proportions in the AF and NP represent differences in the content of type I, type II or both collagens. The total collagen content, measured as hydroxyproline, is approximately twice as high on a μg/mg dry weight basis in the AF as in the NP of the human intervertebral disc (26,35). Confirmation of this finding must await the development of methodology for measuring denatured and total type I collagen.

Studies comparing the biochemical changes of ageing human intervertebral discs with changes in their gross morphology or magnetic resonance imaging profiles have shown that damage to the disc correlates with a decreased proteoglycan concentration (30,31). There was either no correlation with total collagen, measured as hydroxyproline, or possibly an increased collagen concentration with increased damage to the disc in these studies. However, histological analysis has shown clearly that there is increased fraying and fragmentation of collagen in ageing human intervertebral disc (29). Therefore measurements of collagen denaturation and fragmentation may correlate better with morphological changes than does total hydroxyproline content.

We show that in the NP a loss of proteoglycans is associated with a loss of type II collagen in discs with normal gross morphology. These changes are indicative of alterations within the structure of the disc matrix that would be expected to be detrimental to disc function. Indeed, Pearce et al (30) have reported that a decrease in proteoglycan content accompanies disc degeneration and may precede overt morphological damage. Similarly, it is likely that the increased level of type II collagen damage observed in the morphologically normal disc in this study may also be a prelude to degeneration.

EXAMPLE 16

Preparation of an Antigen Peptide for Raising an Antibody to a Site Near the Site of Collagenase Cleavage An antigen peptide was designed having a sequence which corresponds to the carboxy terminus of the three quarter fragment remaining after cleavage of triple helical type II collagen by collagenase-1 (MMP-1), collagenase-2 (MMP-8) or collagenase-3 (MMP-13). Its amino acid sequence was based on published amino acid sequences (48) of fibroblast collagenase (MMP-1) cleaved human type II collagen α1-chains and of collagenase-2 and collagenase-3 cleaved type II collagen α1-chains (49) with the following exception. The assignment of the fourth residue of the collagen antigen peptide sequence as hydroxylated proline (Hyp) was based on the assumption that proline residues in the Y position of the repeating Gly-X-Y triplets that make up the helical portions of collagen molecules are potential hydroxylation sites within the collagen α-chains (52). Moreover, antisera generated to peptides containing a non-hydroxylated proline at this position react poorly to the cleaved three quarter fragment of type II collagen.

The sequence of the immunizing peptide antigen is as follows:

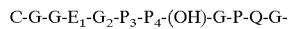

P-(OH) represents hydroxyproline. The E-G-P-P-(OH)-G-P-Q-G portion of the sequence is the natural sequence immediately amino terminal to the collagenase cleavage site in type II collagen, as shown in FIG. 15.

The immunizing peptide antigen was chemically synthesized at a 0.25 mmol scale, using standard Fmoc (9-fluoroenylmethoxycarbonyl) chemistry on a solid-phase peptide synthesizer (model 431A: Applied Biosystems Model 431A, Foster City, Calif.) The residues G-G represent a spacer arm with an amino-terminal cysteine for coupling to ovalbumin with N-hydroxysuccinimidyl bromoacetate. Coupling to ovalbumin was performed as described above in Example 1.

EXAMPLE 17
Preparation of Monoclonal Antibodies to Cleavage Site Epitope

Hybridoma cells were prepared as described above in Example 2. The isotype of the monoclonal antibody was determined using a commercial isotype screening kit (Southern Biotechnology Inc. Birmingham, Ala.).

Hybridoma cells from the best clone produced an antibody designated COL2-3/4C$_{long(mono)}$. A sample of these hybridoma cells were deposited at the American Type Culture Collection (ATCC), 10801 University Blvd., Manassas, Va. 20110-2209, USA, on Nov. 11, 1997, under accession number ATCC HB-12429. The antibody had an IgG isotype.

EXAMPLE 18
Determination of Antibody Titres

Reactivity of the monoclonal antibody was tested using ELISA according to the method described by Billinghurst et al (49). Briefly, various concentrations (1000, 250, 62.5, 15.6, 3.9, 1, 0.25 and 0 ng/ml) of the antigen peptide conjugated to keyhole limpet haemocyanin in 1% BSA were combined with the COL2-3/4C$_{long(mono)}$ monoclonal antibody. Bound COL2-3/4C$_{long(mono)}$ monoclonal antibody was visualized using a goat anti-mouse IgG,M,A (H+L) alkaline phosphatase conjugate (from Zymed) along with an amplifier (ELISA Amplification System—Gibco BRL).

EXAMPLE 19
Determination of Epitope Binding Sites

The specific sequence of the epitope recognized by the monoclonal antibody was identified by synthesizing variants of the immunizing peptide shortened and lengthened at the carboxy terminus. Binding of the monoclonal to these short peptides was evaluated using an inhibition ELISA assay constituted with the immunizing peptide coupled to keyhole limpet haemocyanin (KLH), in the same way as it was coupled to ovalbumin, through the amino terminal cysteine residue as in Example 1. Five ng/well of peptide conjugated with KLH was added as 50 μl/well and incubated overnight to bind at 4° C. Thereafter the procedure described Billinghurst et al (49) was followed. The results are shown in FIG. 16.

As FIG. 16a illustrates, the peptide sequence which corresponds to the sequence of the antigen peptide provides strong inhibition of antibody binding to the antigen peptide. Addition of the next residue in the sequence of uncleaved collagen α$_1$(II), namely a leucine (L) residue to the carboxy terminus of the peptide has little or no effect on antibody reactivity with the antigen peptide. Addition of leucine (L) and alanine (A) partially reduces reactivity, indicating that the reactivity is particularly reduced if the free carboxy terminus is blocked by addition of at least two residues.

Figure 16B:
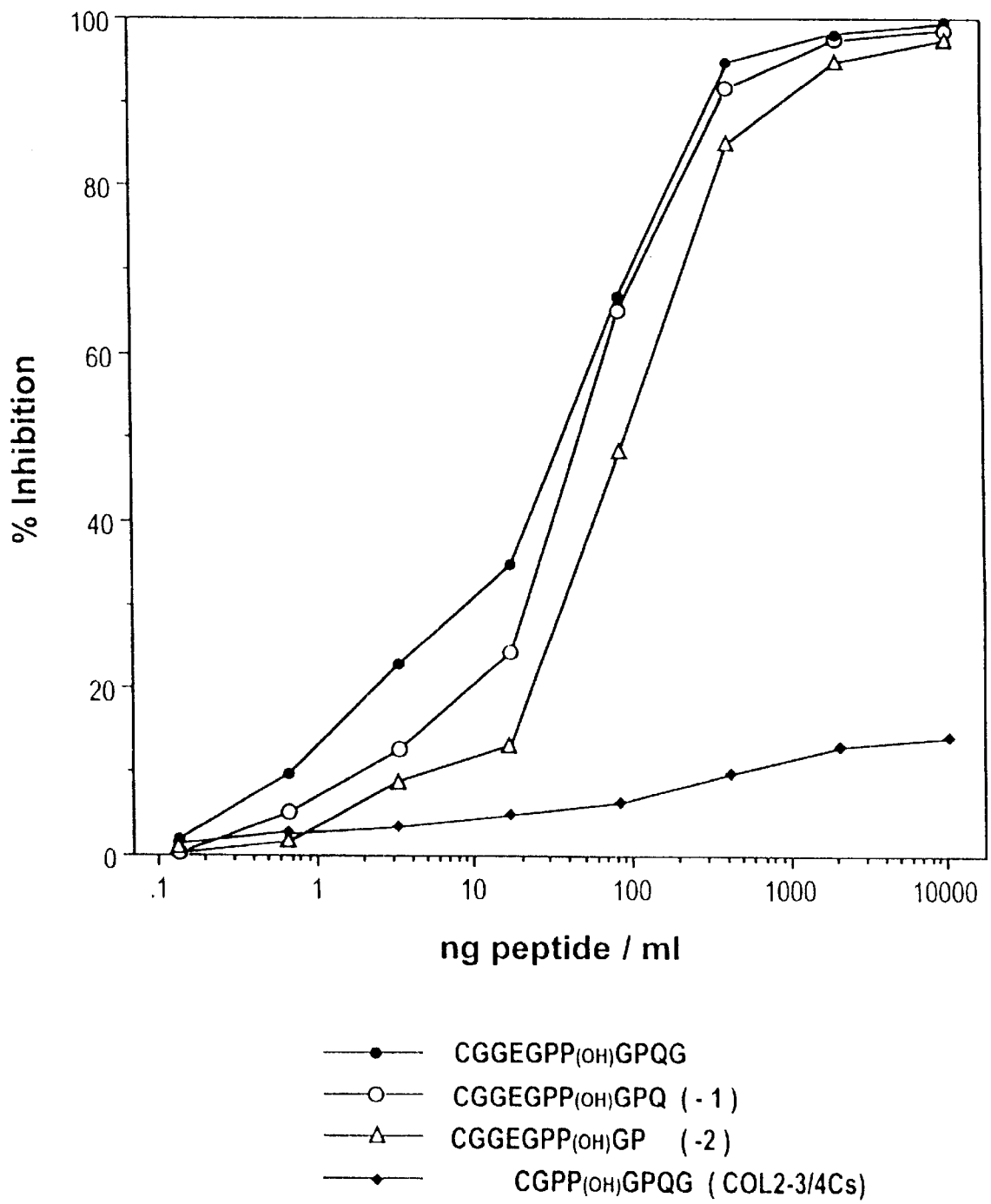

Removal of residues from the antigen peptide at the carboxy terminus reveals that removal of the terminal glycine residue has little effect on reactivity, see FIG. 16b. Removal of the terminal glutamine (Q) and glycine (G) residues reduced reactivity relatively little. Together these observations indicate that the reactivity of the antibody does not have an absolute requirement for both the free carboxy terminal glycine residue and the adjacent glutamine (Q) present at the carboxy terminus. However, removal of the glutamate (E) residue results in an almost complete loss of reactivity, indicating that this residue is essential to the epitope.

EXAMPLE 20
Specificity of the COL2-3/4C$_{long(mono)}$ Monoclonal Antibody for Type II Collagen Cleavage Site In order to assess if the antibody was specific for the collagenase cleavage site of type II collagen, the reactivity of the antibody was evaluated with type I and type II collagen cleaved between residues 775 and 776 by collagenase and type I and type II collagen which had been heat denatured at 80° C. for 20 minutes but not cleaved. Binding of the COL2-3/4C$_{long(mono)}$ monoclonal antibody was evaluated using inhibition ELISA according to the method described by Billinghurst et al (49). The results are summarized in FIG. 17. As is evident from FIG. 17, denatured type I and II collagen were essentially non-reactive with the COL2-3/4C$_{long(mono)}$ monoclonal antibody. Reactivity, on a molar basis, almost comparable to that observed with the antigen peptide, was observed for type II collagen following cleavage by the collagenase-1 or MMP-1 (+MMP-1) and collagenase-3 or MMP-13 (+MMP-13) which enzymes cleave at the same site. Cleavage of type I collagen by MMP-13 resulted in no significant reactivity. Similar results for non-reactivity were obtained for type I collagen cleaved by MMP-1.

Specificity for type II collagen was further evaluated using SDS-PAGE gel electrophoresis and Western immunoblotting of types I, II and III collagen, cleaved (+) or uncleaved (-) with MMP-1 or MMP-13 according to the method described by Billinghurst et al (49). The SDS-PAGE revealed that treatment with MMP-1 (+1) or MMP-13(+13) resulted in cleavage of the α$_1$-chain of type II and type III collagen and of the α$_1$ and α$_2$-chains of type I collagen to produce ¾ (TC$^A$) and ¼ (TC$^B$) length cleavage products. Transfer of these collagens and fragments thereof to nitrocellulose and treatment with the COL2-3/4C$_{long(mono)}$ antibody revealed that the antibody reacted only with type II collagen and further only with the ¾ length digestion product produced by either MMP-1 or MMP-13. The antibody did not react with the intact α-chain. In addition, smaller breakdown products (between the TC$^A$ (75 KD) and TC$^B$ (25 KD) fragments) containing the epitope were also recognized by the COL2-3/4C$_{long(mono)}$ antibody.

These observations demonstrate that the assay will detect only degradation products generated by collagenase cleavage of type II collagen.

EXAMPLE 21
Comparison of the COL2-3/4C$_{Long(Mono)}$ Monoclonal Antibody to Polyclonal Antibody Designated COL2-3/4C$_{Short}$ Billinghurst et al (49) described the development of a polyclonal antibody (COL2-3/4C$_{short}$) to a neoepitope of sequence (SEQ ID NO:6) G-P-P(OH)-G-P-Q-G. The epitope binding site of the polyclonal COL2-3/4C$_{short}$ was compared to that of the COL2-3/4C$_{long(mono)}$ monoclonal by comparing the effect of removing residues on reactivity. The results for the COL2-3/4C$_{long(mono)}$ monoclonal are summarized above at Example 18. The results for the COL2-3/4C$_{short}$ were summarized by Billinghurst et al (49). Briefly, reactivity of the polyclonal COL2-3/4C$_{short}$ was lost following removal of only the glycine (G) at the carboxy terminus. This differs from Example 19, where reactivity of the COL2-3/4C$_{long(mono)}$ monoclonal antibody was reduced relatively little by removal of the terminal glycine (G) or by removal of the terminal glutamine (Q) and glycine (G) from the antigen peptide.

The peptide used to generate the COL2-3/4C$_{short}$ polyclonal antibody was tested in an assay with the COL2-3/4C$_{long(mono)}$ monoclonal antibody. The results, shown in FIG. 16b indicate that the monoclonal antibody does not recognize this peptide COL2-3/4Cs.

These results indicate that the COL2-3/4C$_{long(mono)}$ monoclonal antibody does not bind to the same epitope as the COL2-3/4C$_{short}$ polyclonal antibody. It is likely that the COL2-3/4C$_{long(mono)}$ monoclonal antibody recognizes a conformational epitope generated by collagenase that is specific for type II collagen.

EXAMPLE 22

Use of the COL2-3/4C$_{Long(Mono)}$ Monoclonal Antibody Assay To Analyse Type II Collagenase Generated Fragments of Type II Collagen in Human and Animal Body Fluids Analysis of body fluids requires the ability to accurately detect the epitope recognized by the antibody in these fluids and to ensure that the immuno-reactivity of the epitope in these fluids exhibits the same characteristics as the epitope (i.e. the antigen peptide) recognized by the antibody.

Analyses were performed using ELISA according to the method described in Example 19 to ascertain whether the COL2-3/4C$_{long(mono)}$ monoclonal antibody demonstrated reactivity in body fluids parallel to the reactivity shown with the antigen peptide. The body fluids analyzed were human urine, synovial fluid and serum. The results are summarized in FIG. 18. Corresponding analyses were conducted on urine and serum from rabbits. The results are shown in FIG. 19. In each case, the inhibition curves obtained using ELISA were essentially parallel for the antigen peptide and the body fluid tested and acceptable for an assay of this kind.

Next, the capacity of the COL2-3/4C$_{long(mono)}$ monoclonal antibody to detect the antigen peptide when added to each of four different body fluids was assessed. Antigen peptide was added to each of four samples of urine, four of synovial fluid and four of serum from humans. Each sample was assayed for endogenous epitope and added epitope. This amount of added epitope usually corresponded to between 50 and 100% of the amount of epitope already present in the body fluid. For each sample n=4. The peptide was added once at 20 ng/ml and once at 40 ng/ml. This represents eight measurements in total on four different samples.

The results are plotted in FIG. 20a. They are represented by boxes, the upper and lower limits of which represent the 75% and 25% percentiles; the whiskers represent 90% and 10% percentiles. The individual data points are the outliers above and below 90% and 10% respectively. The medians are shown within the boxes. The results reveal that excellent recovery is ordinarily observed in studies of synovial fluids. Recoveries are somewhat reduced or elevated for urine and serum, respectively. However, the median recovery is within ±20% of the expected value, namely endogenous plus exogenous (added) epitope, and hence the recovery is considered acceptable for an assay of this kind.

Similar studies were performed on body fluids of rabbits since these animals are frequently used to study experimental inflammatory (rheumatoid) arthritis and osteoarthritis. As FIG. 19 shows, acceptable parallellity to the standard curve (immunizing epitope) was observed for urine (FIG. 19a) and serum (FIG. 19b) samples. In FIG. 20b it can be seen that excellent recovery was usually observed for rabbit serum samples and acceptable recovery was observed for rabbit urine samples. These experiments on recovery were conducted in the manner described for human samples.

EXAMPLE 23

Use of the COL2-3/4C$_{Long(Mono)}$ Monoclonal Antibody Assay To Study Cartilage Type II Collagen Degradation Products in Body Fluids of Patients with Arthritis Patients with rheumatoid arthritis were studied using the COL2-3/4C$_{long(mono)}$ assay to determine the content of the epitope in relation to non-arthritic controls and to alterations in disease activity.

Analyses of sera and urine from non-arthritic adult controls and patients with rheumatoid arthritis obtained at clinic visits revealed that the content of the recognized epitope by COL2-3/4C$_{long(mono)}$ is significantly elevated in serum (FIG. 21a) and to a lesser extent in urine (FIG. 21b) of patients with rheumatoid arthritis. Specifically, normal patients showed median values of 37.0 pmol peptide/ml in serum and 6.34 pmol peptide/ml in urine whereas patients with rheumatoid arthritis showed 62.1 pmol peptide/ml in serum and 10.9 pmol peptide/ml in urine. The results suggest that we can detect increased type II collagen degradation in cartilage in patients with arthritis. There was a significant correlation between serum values and those for urine in all persons both normal and arthritic (r=0.282, p=0.0032, n=110). Significant Spearman rank correlations were also found for the serum epitope with total joint count determined by the total number of painful and tender joints (r=0.334, p=0.0023, n=84) and the total number of swollen joints (r=0.35, p=0.0014, n=84) and for physicians' global assessment of disease activity (r=0.216, p=0.0376, n=94). These correlations with joint inflammation and disease activity were not observed for urine samples. They suggest that the increase in collagen epitope in serum reflects increased cartilage damage in these inflamed joints.

In a separate study we examined each patient on at least two separate occasions to see if epitope content in serum was correlated with disease activity. We measured the C2-3/4C$_{long(mono)}$ epitope content in serum.

The total number of painful and tender joints was determined on two consecutive clinic visits when serum samples were obtained. Patients were divided into those in which there was no change in the total number of painful and tender joints (no clinical change), those in which total joint count decreased (clinically improved) and those in which joint count increased (clinically worse) by at least 20%. The changes were recorded as the mean coefficient of percentage variation % CV±S.D. In the group showing clinical improvement (joint count decreased), there was a clear majority of patients (19/27 or 70%) which exhibited a percentage CV change (26.3±20.8, mean ± S.D.) characterized by a decrease in the epitope content (see Table X).

These preliminary observations indicate that the measured clinical improvement reflective of decreased joint inflammation is observed in a majority of patients which show a decrease in serum epitope content, suggesting a reduction in the cleavage of cartilage type II collagen in the diseased joints of these patients. Hence the new assay can be used to provide an early indication of cartilage damage and of clinical response to treatment at the level of cartilage matrix degradation. The results indicate that the assay can be useful in providing a prognosis for a patient. In addition, the assay can be used to assist in ascertaining the appropriate dosage and effectiveness of medication based on patient response, by examining responses in patients and healthy volunteers in clinical trials.

EXAMPLE 24

Use of the COL2-3/4C$_{Long(Mono)}$ Monoclonal Antibody Assay To Study Cartilage Type II Collagen Degradation Products in Cell Culture Studies in Culture Medium We have shown that it is possible to culture articular cartilages and measure the release of a collagen epitope into culture media which reflects degradation of collagen (49). This new epitope, COL2-3/4C$_{long(mono)}$, can also be measured by immunoassay in culture media. Thus it could be used to detect type II collagen cleavage in cultured articular cartilage and to detect or measure the effects of inhibitors on collagenases or other proteinases producing this epitope. This can be useful in screening drugs for their ability to arrest degradation of cartilage collagen caused by collagenases.

EXAMPLE 25

Imaging of Cartilage Type II Collagen Cleavage Using Antibody COL2-3/4C$_{Long(Mono)}$ The COL2-3/4C$_{long(mono)}$ antibody was used in conjunction with microscope sections of healthy and osteoarthritic articular cartilages. The sections were cut with a freezing microtome, then were contacted with the mouse monoclonal antibody COL2-3/4C$_{long(mono)}$. The antibody binds much more to the sections of osteoarthritic cartilage than to the normal cartilage. Binding of the COL2-3/4C$_{long(mono)}$ is visualized by subsequent treatment with a second pig anti-mouse antibody which has been labelled with biotin. Excess pig antibody (unbound) is removed by washing and the biotin is subsequently reacted with streptavidin labelled with horseradish peroxidase. Binding of the streptavidin-peroxidase complex to the biotin labelled second pig antibody (and hence binding of first mouse antibody) produces a brown/black unsoluble reaction product at the site in the tissue where the mouse monoclonal antibody originally bound. Thus, the appearance of brown/black coloration is indicative of the presence of epitope generated by collagenase-mediated cleavage of type II collagenase. Furthermore, increases or decreases in the amount of the epitope are indicated by corresponding increases or decreases in the amount of brown/black coloration in the tissue. The methodology used to study tissue sections is described in Hollander et al, (1995) (50) and Gallyas and Merchanthaler, (1988) (45) and Example 14.

Comparing normal tissue to osteoarthritic tissue, the normal tissue showed little or no brown/black coloration except for a trace amount present at the articular surface. In osteoarthritic cartilage, very strong brown/black staining was observed at and close to the damaged articular surface and around the cells (chondrocytes) elsewhere in the cartilage.

These observations demonstrate that it is possible to use the COL2-3/4C$_{long(mono)}$ antibody to detect increased cleavage of type II collagen by collagenase within arthritic cartilage.

Furthermore, these results indicate that type II collagen degradation can be detected in a patient in vivo by direct labelling of the COL2-3/4C$_{long(mono)}$ antibody using a label that can be detected in vivo. Alternatively, the smaller and more diffusible antibody Fab sub-unit containing the antibody binding site could be introduced to a patient intravenously. The COL2-3/4C$_{long(mono)}$ antibody or its fragment can then be allowed to diffuse out of blood vessels into extravascular sites where it is free to react with and bind to collagenase-generated epitope in cartilage. Binding to epitope in cartilage leads to its accumulation. Labelling the antibody with gadolinium, (a label used to create a strong signal for magnetic resonance imaging (MRI)), (51) or with technetium, would enable the antibody to be detected using a γ-camera as in scintigraphy, (which is also commonly used clinically) thus indicating sites in arthritic or damaged cartilage where cleavage of collagen by collagenase is excessive. It may be necessary to allow for a suitable time delay between administration of the antibody and imaging to allow for the labelled antibody to bind and accumulate in cartilage and to allow for unbound labelled antibody to diffuse away, thus reducing background. Direct detection of the COL2-3/4C$_{long(mono)}$ in vivo would be applicable to the study of damaged or diseased large and small joints or the spine (intervertebral disc) to detect cartilage damage, just as scintigraphy is used clinically to detect increased vascularity associated with inflammation in joints and for the detection of increased bone turnover associated with joint inflammation and damage. By imaging with magnetic resonance in conjunction with gadolinium, a more specific interpretation of the MRI signal in studies of joint damage and disease can be obtained than that which is presently possible.

EXAMPLE 26

Humanized COL2-3/4$_{Long(Mono)}$ Monoclonal Antibody

The COL2-3/4C$_{long(mono)}$ can be humanized using techniques which are known in the art (54). Briefly, the amino acid sequences from the six complementarity determining regions (CORs) of the COL2-3/4C$_{long(mono)}$ are grafted onto a human antibody framework. In order to produce a humanized antibody with optimal binding to the desired epitope, variants of the humanized antibody can be generated by randomizing residues of the human framework known to be critical to antigen binding. A library of antibody molecules can be expressed on the surface of filamentous phage. Antibodies demonstrating optimal binding can be identified by affinity-based selection (54).

Humanization of the COL2-3/4C$_{long(mono)}$ antibody would have the effect of reducing the anti-mouse immunogenicity that may be observed when murine antibodies are administered to humans. It would also prolong the serum half-life of the antibody in humans.

TABLE V

Patient details

| Disease group | n | Mean age in years | Age range | % Male-Female | Median Mankin grade | Range of Mankin grades |
|---|---|---|---|---|---|---|
| Normal | 8 | 56 | 28–81 | 50:50 | 2 | 0–6 |
| OA | 16 | 69 | 57–84 | 57:84 | 5 | 2–10 |

TABLE VI

Clostridial collagenase cleaves the α$_1$ (II)-CB11B epitope

| Sample | Treatment | [α1(II)-CB11B] by immunoassay (μg/ml) |
|---|---|---|
| Tris | Bacterial collagenase | 0.85 |
| HDC | Tris/CaCl$_2$ | 3.80 |
| HDC | Clostridial collagenase | 0.84 |
| α1(II)-CB11B | Tris/CaCl$_2$ | 4.44 |
| α1(II)-CB11B | Clostridial collagenase | 0.83 |

HDC and α1(II)-CB11B were dissolved in Tris containing 5 mM CaCl$_2$ and 14 U/ml chromatographically purified bacterial collagenase. Control tubes contained HDC or α1(II)-CB11B in Tris with 5 mM CaCl$_2$ but no bacterial collagenase or bacterial collagenase in Tris with 5 mM CaCl$_2$ but no HDC or α1(II)-CB11B. The samples were incubated overnight at 37° C. and the bacterial collagenase was inactivated by addition of EDTA to a final concentration of 100 mM (this concentration was required to ensure maximal inhibition of the proteinase).

TABLE VII

The inhibition observed in cartilage extracts is lost on treatment with Clostridial collagenase

| Sample | Proteinase Digestion | [α1(II)-CB11B] by immunoassay (μg/ml) | |
|---|---|---|---|
| | | Digested sample treated with Tris/CaCl$_2$ | Digested sample treated with Tris/CaCl$_2$ + collagenase |
| Tris | None | 0.00 | 0.46 |
| OA-(i) | α-chymotrypsin | 1.39 | 0.47 |
| OA-(ii) | α-chymotrypsin | 3.22 | 0.45 |
| OA-(iii) | α-chymotrypsin | 2.11 | 0.43 |
| OA-(iv) | α-chymotrypsin | 3.53 | 0.48 |
| OA-(v) | α-chymotrypsin | 2.86 | 0.47 |
| OA-(i) | Proteinase K | 53.4 | 0.49 |
| OA-(ii) | Proteinase K | 93.2 | 0.47 |
| OA-(iii) | Proteinase K | 82.5 | 0.47 |
| OA-(iv) | Proteinase K | 148.9 | 0.40 |
| OA-(v) | Proteinase K | 61.7 | 0.56 |

OA cartilages (i–v) were extracted/digested with α-chymotrypsin and proteinase K. The digested samples were then treated with Tris/5 mM CaCl$_2$ with or without 14 U/ml Clostridial collagenase at 37° C. Clostridial collagenase activity was inhibited with 100 mM EDTA. The samples were assayed for $\alpha_1$(II)-CB11B.

TABLE VIII

Total and denatured collagen in different depths of normal and OA cartilage

| Disease group | [Total type II collagen] μg/mg | | % Denatured type II collagen | |
|---|---|---|---|---|
| | Zones | | Zones | |
| | Upper | Lower | Upper | Lower |
| Normal | 139.9 | 179.5 | 2.42 | 1.12 |
| OA | 92.4$^{NS}$ | 128.9* | 3.2$^{NS}$ | 2.2** |

Zones are 1 mm thick. Values are the mean result for cartilage from 5 normal and 8 OA patients. NS=not significant, *p<0.03; **p<0.02 v. normal cartilage; Mann-Whitney U-test. Results for the individual patients and statistical comparisons of data for upper versus lower zones in each patient group are shown in Table VIII.

TABLE IX

Details of individual cases

| AUTOPSY CASE | AGE (YEARS) | SEX | CAUSE OF DEATH |
|---|---|---|---|
| A | 76 | Male | Cardiac Arrest |
| B | 72 | Female | Brain Tumor |
| C | 33 | Female | Brain Tumor |
| D | 67 | Female | Gastric Carcinoma |
| E | 60 | Female | Aspiration |
| F | 72 | Female | Lymphoma |
| G | 39 | Female | Breast Carcinoma |

TABLE X

| Clinical parameter Joint count for Pain and Tenderness | Patient Number | COL2-3/4C$_{long\ (mono)}$ | No | m CV % | SD |
|---|---|---|---|---|---|
| unchanged | 10 | no change | 0 | | |
| | | increase | 6 | 26.3 | 26.83 |
| | | decrease | 4 | 15.85 | 8.04 |
| decreased | 26 | no change | 1 | 0 | |
| | | increase | 8 | 15.03 | 12.11 |
| | | decrease | 18 | 26.19 | 20.84 |
| increased | 9 | no change | 0 | | |
| | | increase | 4 | 9.9 | 6.64 |
| | | decrease | 5 | 35.34 | 30.72 |

The mean percentage coefficient of variation (mCV %) for the number of patients indicated is shown +/– standard deviation

REFERENCES

1. Dodge, G. R., and Poole, A. R. (1989). Immunohistochemical detection and immunochemical analysis of type II collagen degradation in human normal, rheumatoid and osteoarthritic cartilages and in explants of bovine articular cartilage cultured with interleukin-1. *J. Clin. Invest.* 83:647–661.
2. Fell, H. B., Barratt, M. E. J., Welland, H., Green, R., and Poole, A. R. (1976). The capacity of pig articular cartilage in organ culture to regenerate after breakdown induced by complement-sufficient antiserum to pig erythrocytes. *Calcif. Tiss. Res.* 20:3–21.
3. Scott, P. G., Telser, A. G. and Veis, A. (1976) Semi-quantitative determination of cyanogen bromide peptides of collagen in SDS-polyacrylamide gels. *Anal. Biochem.* 70:251–257.
4. Fazekas de St. Groth, S. and Scheidigger, D. (1980) Production of monoclonal antibodies: strategy and tactics, *J. Immunol. Meth.* 35: 1–21.
5. Epstein, E. H., Jr. (1974). Alpha 1(3)3 human skin collagen. Release by pepsin digestion and preponderance in fetal life. *J. Biol. Chem.* 249:3225–3231.
6. Eyre, D. R., Wu, J- J. and Woolley, D. E. (1984) All three chains of 1α2α3α collagen from hyaline cartilage resist human collagenase. *Biochem. Biophys. Res. Comm.* 118:724–729.
7. Kirsch, T. and von der Mark, K. (1991) Isolation of human type X collagen and immunolocalization in fetal human cartilage. *Europ. J. Biochem.* 196:575–580.
8. Pal, S., Tang, L- H., Choi, H., Habermann, E., Rosenberg, L., Roughley, P. and Poole, A. R. (1981) Structural changes during development in bovine fetal epiphyseal cartilage. *Collagen Relat. Res.* 1:151–176.
9. Rizkalla, G., Reiner, A., Bogoch, E. and Poole, A. R. (1992) Studies of the articular cartilage proteoglycan aggrecan in health and osteoarthritis. Evidence for molecular heterogeneity and extensive molecular changes in disease. *J. Clin. Invest.* 90:2268–2277.
10. Mankin, H. J., Dorfman, H., Lippiello, L. and Zarins, A. (1971). Biochemical and metabolic abnormalities in articular cartilage from osteoarthritic human hips. *J. Bone Joint Surg.* 53A:523–537.
11. Poole, A. R., Alini, M. and Hollander, A. P. (1994). Cartilage degradation. In Mechanisms and Models in Rheumatoid arthritis. B. Henderson, J. Edwards and R. Pettipher, editors. Academic Press, London. In Press.
12. Kempson, G. E., Muir, H., Pollard, C. and Tuke, M. (1973). The tensile properties of the cartilage of human femoral condyles related to the content of collagen and glycosaminoglycans. *Biochimica et Biophysica Acta* 297:465–472.
13. Akizuki, S., Mow, V. C., Muller, F., Pita, J. C. and Howell, D. S. (1986). Tensile properties of human knee joint cartilage. I. Influence of ionic conditions, weight bearing and fibrillation on the tensile modulus. *J. Orthop. Res.* 4:379–392.
14. Mow, V., Howell, D. S. and Buckwalter, J. A. (1990). Structure-function relationships of articular cartilage and the effects of joint instability and trauma on cartilage function. In Cartilage Changes in Osteoarthritis. K. D. Brandt, editor. Indiana University School of Medicine, Ciba-Geigy Co. 22–42.
15. Poole, A. R. (1993). Cartilage in health and disease. In Arthritis and Allied Conditions. A Textbook of Rheumatology. D. J. McCarty and W. J. Koopman, editors. Lea and Febiger, Phila., 279–333.
16. Kempson, G. (1980). The mechanical properties of articular cartilage. In The Joints and Synovial Fluid, Vol. 2. L. Solokoff, editor. Academic Press Inc., N.Y. 177–238.
17. Schmidt, M. B., Mow, V. C., Chun, L. E. and Eyre, D. R. (1990). Effects of proteoglycan extraction on the tensile behaviour of articular cartilage. *J. Orthop. Res.* 8:353–363.
18. Kempson, G. E. (1991). Age-related changes in the tensile properties of human articular cartilage: a comparative study between the femoral head of the hip joint and the talus of the ankle joint. *Biochimica et Biophysica Acta* 1075:223–230.
19. Venn, M., and Maroudas, A. (1977). Chemical composition and swelling of normal and osteoarthritic femoral head cartilage. I. Chemical composition, *Ann. Rheum. Dis.* 36:121–129.
20. Mohtai, M., Smith, R. Lane, Schurman, D. J., Tsuji, Y., Torti, F. M., Hutchinson, N. I., Stetler-Stevenson, W. G and Goldberg, G. I. (1993). Expression of 92-kD type IV collagenase/gelatinase (gelatinase B) in osteoarthritic cartilage and its induction in normal human articular cartilage by interleukin 1. *J. Clin. Invest.* 92:179–185.
21. Dodge, G. R., Pidoux, I. and Poole, A. R. (1991). The degradation of type II collagen in rheumatoid arthritis: An immunoelectron microscopic study. *Matrix* 11:330–338.
22. Poole, A. R., Mort, J. S. and Roughley, P. J. (1993). Methods for evaluating mechanisms of cartilage breakdown. In Joint Cartilage Degradation. J. F. Woessner Jr., and S. D. Howell, editors. Marcel Dekker, Inc., N.Y. 225–260.
23. Morris, N. P., and Bächinger, H. P. (1987). Type XI collagen is a heterotrimer with the composition ($1\alpha 2\alpha 3\alpha$) retaining non-triple-helical domains. *J. Biol. Chem.* 262:11345–11350.
24. Eyre, D. R., and Wu, J. -J. (1987). Type XI or $1\alpha 2\alpha 3\alpha$ collagen. In Structure and Function of Collagen Types, R. Mayne, and R. E. Burgeson, editors. Academic Press Inc. N.Y. 261–281.
25. Eyre, D. R., Wu, J. -J. and Apone, S. (1987). A growing family of collagens in articular cartilage: Identification of 5 genetically distinct types. *J. Rheumatol.* 14 (Suplt.) :25–27.
26. Humzah, M. D., Soames, R. W.: Human intervertebral disc: structure and function. *Anat. Rec.* 220:337–356, (1988).
27. Thompson, J. P., Pearce, R. H., Schechter, M. T., Adams, M. E., Tsang, I K Y, Bishop, P. B.: Preliminary evaluation of a scheme for grading morphology of the human intervertebral disc. Spine 15:411–415, (1990).
28. Vernon-Roberts, B.: Disc pathology and diseases states. The biology of the intervertebral disc. Vol. 2. Edited by P. Ghosh. Florida, CRC Press Inc., (1988), pp. 73–119.
29. Bernick, S., Walker, J. M., Paule, W. J.: Age changes to the annulus fibrosus in human intervertebral discs. *Spine* 16:520–524, (1991).
30. Pearce, R. H., Beverley, J. G., Adams, M. E.: Degeneration and the chemical composition of the human lumbar intervertebral disc. *J. Orthop. Res.* 5:198–205, (1987).
31. Pearce, R. H., Thompson, J. P., Bebault, G. M., Flak, B.: Magnetic resonance imaging reflects changes of aging degeneration in the human intervertebral disc. *J. Rheumatol.* (Suppl. 27) 18:42–43, (1991).
32. Eyre, D. R., Muir, H.: Quantitative analysis of types I and II collagens in human intervertebral discs at various ages. *Biochim. Biophys. Acta.* 492:29–42, (1977).
33. Roberts, S., Menage, J., Duance, V., Wotton, S., Ayad, S.: Collagen types around the cells of the intervertebral disc and cartilage end plate: an immunolocalization study. *Spine* 16:1030–1038, (1991).
34. Eyre, D.: Collagens of the disc. The biology of the intervertebral disc. Vol. 1. Edited by P. Ghosh, Florida, CRC Press Inc., (1988), pp.171–188.
35. Roberts, S., Menage, J., Urban, J. P.: Biochemical and structural properties of the cartilage end-plate and its relation to the intervertebral disc. *Spine* 14:166–174, (1989).
36. McDevitt, C. A.: Proteoglycans of the intervertebral disc. The biology of the intervertebral disc. Vol. 1. Edited by P. Ghosh, Florida, CRC Press Inc., (1988), pp. 151–170.
37. Mort, J. S., Dodge, G. R., Roughley, P. J., Liu, J., Finch, S. J., DiPasquale, G., Poole, A. R.: Direct evidence for active metalloproteinases mediating matrix degradation in interleukin 1-stimulated human articular cartilage. *Matrix* 13:95–102, (1993).
38. Dodge, G. R., Pidoux, I., Poole, A. R.: The degradation of type II collagen in rheumatoid arthritis: An immunoelectron microscopic study. *Matrix* 11:330–338, (1991).
39. Dodge, G. R., Poole, A. R.: Immunohistochemical detection and immunological analysis of type II collagen degradation in human normal, rheumatoid and osteoarthritic articular cartilages and in explants of bovine articular cartilage cultured with interleukin 1. *J. Clin. Invest.* 83:647–661, (1989).
40. Burleigh, M. C., Barrett, A. J., Lazarus, G. S.: Cathepsin Bl. A lysosomal enzyme that degrades native collagen. *Biochem J.* 137:387–398, (1974).
41. Hollander, A. P., Atkins, R. M., Eastwood, D. M., Dieppe, P. A., Elson, C. J.: Human cartilage is degraded by rheumatoid arthritis synovial fluid but not by recombinant cytokines in vitro. *Clin. Exa. Immunol.* 83:52–57, (1991).
42. Henderson, C.: Aminoalkylsilane: an inexpensive, simple preparation for slide adhesion. *J. Histotech.* 12:123–124, (1989).
43. Poole, A. R., Pidoux, I., Reiner, A., Tang, L- H., Choi, H., Rosenberg, L.: Localization of proteoglycan monomer and link protein in the matrix of bovine articular cartilage. *J. Histochem. Cytochem.* 28:621–635, (1980).
44. Scott, P. G., Telser, A. G., Veis, A.: Semiquantitative determination of cyanogen bromide peptides of collagens in SDS-poly acrylamide gels. *Anal. Biochem.* 70:251–257, (1976).
45. Gallyas, F., Merchenthaler, I.: Copper-$H_2O_2$ oxidation strikingly improves silver intensification of the nickel-diaminobenzidene (Ni-DAB) end-product of the peroxidase reaction. *J. Histochem. Cytochem.* 36:807–810, (1988).

46. Hollander, A. P., Heathfield, T. F. Pidoux, I., Fisher, W., Bogosh, E., Poole, A. R.: Increased denaturation but no change in the total content of type II collagen in cartilage from patients with rheumatoid arthritis. *Arthritis Rheum.* (Unpublished).
47. Nimni, M. E.: Collagen: Structure and function and metabolism in normal and fibrotic tissues. *Semin. Arthritis Rheum.* 13:1–86, (1983).
48. Birkedal-Hansen, H. et al (1993) Matrix Metalloproteinases: A review. *Crit. Rev. Oral Biol. Med.* 4:197–250.
49. Billinghurst, R. C. et al, Enhanced Cleavage of Type II Collagen By Collagenases in Osteoarthritic Articular Cartilage (1997) *J. Clin Invest.* 99: 1534–1545.
50. Hollander, A. P., Pidoux, I., Reiner, A., Rorabeck, C., Bourne, R., and Poole, A. R. (1995). Damage to type II collagen in aging and osteoarthritis starts at the articular surface, originates around chondrocytes, and extends into the cartilage with progressive degeneration. *J. Clin. Invest.,* 96:2859–2869.
51. Chandnani, V. P., Ho, C., Chu, P., Trudell, D., Resnick, D. Knee hyaline cartilage evaluated with MR imaging: A cadaveric study involving multiple imaging sequences and intraarticular injection of gadolinium and saline solution. *Radiology,* (1991), 178:557–561.
52. Kielty, C. M. et al, Collagen: The Collagen Family: Structure, Assembly and Organization in the Extracellular Matrix In Royce, P. M. et al eds. Connective Tissue and its Heritable Disorders. New York: Wiley-Liss Inc., (1993) at 103–147.
53. Timpl, R. Immunology of Collagens. In Extracellular Matrix Biochemistry. K. Piez and A. H. Reddi, editors. Amsterdam: Elsevier/North Holland Publishers, (1984).
54. Baca, M., Presta, L. G., O'Connor, S. J., Wells, J. A. Antibody Humanization Using Monovalent Phage Display. *J. Biol. Chem.,* (1997), 272:10678–10684.

We claim:

1. A method for detecting cartilage degradation in a biological sample by identifying the presence of unwound type II collagen in the biological sample, said method comprising:

contacting the biological sample with a monoclonal antibody which does not bind to native helical collagen but which does bind to an epitope on unwound type II collagen chains or fragments thereof, wherein said epitope has the following sequence (SEQ ID NO: 4):

A-P(OH)-G-E-D-G-R-P(OH)-G-P-P(OH)-G-P; and detecting the presence of the bound monoclonal antibody.

2. The method according to claim 1 wherein said monoclonal antibody is produced by the cell line ATCC HB 11202.

3. The method according to claim 1, wherein said biological sample is a biological fluid.

4. A method for the determination of cartilage degradation in a biological sample by quantifying the amount of unwound type II collagen in the biological sample, said method comprising:

(a) contacting the biological sample with a first enzyme which cleaves unwound type II collagen chains in the biological sample into collagen fragments without cleaving an antibody-reactive epitope on said unwound type II collagen chains;

(b) extracting the collagen fragments produced by said enzyme from said biological sample to produce an enzyme extract and remaining biological sample;

(c) treating said remaining biological sample with a second enzyme to solubilize and unwind remaining native collagen contained therein without degrading the epitope to produce a solubilized biological sample;

(d) separately contacting said extract and said solubilized biological sample with a monoclonal antibody which binds an epitope on unwound type II collagen chains or fragments thereof containing said epitope, wherein said monoclonal antibody does not bind to native helical collagen;

(e) determining the amount of unwound type II collagen and fragments thereof in said extract and said solubilized biological sample by separately determining the amount of bound monoclonal antibody; and (f) quantifying the amount of type II collagen that is unwound in said sample by comparing the amount of unwound type II collagen in said extract to the amount of type II collagen in said solubilized biological sample.

5. The method of claim 4, further comprising the step of determining the amount of wound collagen extracted by the first enzyme, said method comprising,
   (a) removing an aliquot of said enzyme extract;
   (b) treating said aliquot with said second enzyme;
   (c) contacting said aliquot with a monoclonal antibody which binds an epitope on unwound type II collagen chains or fragments thereof containing said epitope, wherein said monoclonal antibody does not bind to native helical collagen; and
   (d) determining the amount of unwound type II collagen and fragments thereof in said aliquot by determing the amount of bound monoclonal antibody.

6. The method according to claim 4, wherein said first enzyme is chymotrypsin.

7. The method according to claim 4, wherein said second enzyme is proteinase K.

8. A method according to claim 4, wherein said monoclonal antibody is produced by the cell line ATCC HB 11202.

9. A method for measuring total type II collagen content in a biological sample, said method comprising:
   (a) treating the biological sample to solubilize and unwind collagen contained therein, without degrading an epitope that binds to a monoclonal antibody to produce a solubilized biological sample containing unwound collagen;
   (b) measuring the amount of unwound collagen present in said solubilized biological sample by contacting said solubilized biological sample with the monoclonal antibody which binds an epitope on unwound type II collagen chains or fragments thereof containing said epitope, wherein said monoclonal antibody does not bind to native helical collagen; and
   (c) determining the amount of said unwound collagen and fragments thereof bound to said monoclonal antibody.

10. The method according to claim 4, wherein said biological sample is osteoarthritic cartilage.

11. The method according to claim 4, wherein said biological sample is intervertebral discs.

12. A kit for the measurement of cartilage degradation products in a biological sample, said kit comprising:
   (a) a monoclonal antibody which does not bind to native helical type II collagen but which does bind to an epitope on unwound type II collagen chains or fragments thereof containing said epitope;
   (b) a solid support for binding proteins;
   (c) a labelled antibody to measure the binding of monoclonal antibody to said unwound collagen; and
   (d) an enzyme which solubilizes and unwinds native helical type II collagen without degrading the antibody reactive epitope on unwound type II collagen.

13. The kit according to claim 12, wherein said enzyme is proteinase K.

14. The kit according to claim 12, further comprising:
   a second enzyme which selectively cleaves unwound type II collagen chains in said biological sample without cleaving the antibody-reactive epitope on said unwound type II collagen chains.

15. The kit according to claim 14, wherein said second enzyme is chymotrypsin.

16. The kit according to claim 12, wherein said monoclonal antibody is produced by the hybridoma cell line ATCC HB 11202.

17. A monoclonal antibody which binds to an epitope on unwound type II collagen chains or fragments thereof containing said epitope, wherein said epitope has the following sequence (SEQ ID NO:4):

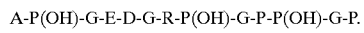

A-P(OH)-G-E-D-G-R-P(OH)-G-P-P(OH)-G-P.

18. The monoclonal antibody produced by the hybridoma cell line ATCC HB 11202.

19. A cell line producing a monoclonal antibody which does not bind to native helical collagen type II but which does bind to an epitope on unwound collagen type II chains or fragments thereof containing said epitope, said epitope having the following sequence (SEQ ID NO:4):

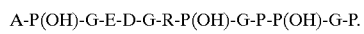

A-P(OH)-G-E-D-G-R-P(OH)-G-P-P(OH)-G-P.

20. A cell line according to claim 19, which has all the identifying characteristics of ATCC HB 11202.

21. The method according to claim 1, wherein said monoclonal antibody detects approximately the same amount of collagen as that detected by measuring hydroxyproline content.

22. The method according to claim 4, wherein said monoclonal antibody detects approximately the same amount of collagen as that detected by measuring hydroxyproline content.

23. The kit according to claim 12, wherein said monoclonal antibody detects approximately the same amount of collagen as that detected by measuring hydroxyproline content.

24. The method according to claim 4, wherein the biological sample is a biological fluid.

25. The method according to claim 4, wherein said biological sample is a biological tissue.

26. A method for detecting collagenase induced cartilage degradation in a biological sample by identifying the presence of an epitope on type II collagen which only becomes detectable following cleavage of said collagen by collagenase, said method comprising:
   contacting the biological sample with a monoclonal antibody which binds to said epitope on type II collagen chains or fragments thereof containing said epitope; and
   detecting the presence of said monoclonal antibody bound to the type II collagen and fragments.

27. The method of claim 26, wherein said epitope has the following sequence (SEQ ID NO: 7):

C-G-G-E-G-P-P-(OH)-G-P-Q-G.

28. The method of claim 26, wherein said biological sample is a biological fluid.

29. The method of claim 28, wherein said biological fluid is selected from the group consisting of synovial fluid, serum and urine.

30. The method of claim 26, wherein said monoclonal antibody is produced by the cell line ATCC HB-12429.

31. A kit for detecting collagenase induced cartilage degradation in a biological sample, said kit comprising:
  (a) a monoclonal antibody which binds to an epitope on type II collagen, or fragments thereof, which only becomes detectable following cleavage of said collagen by collagenase;
  (b) a solid support for binding proteins; and
  (c) a labelled antibody to measure the binding of monoclonal antibody to said unwound collagen.

32. A kit according to claim 31, wherein said monoclonal antibody is produced by the hybridoma cell line ATCC HB-12429.

33. A monoclonal antibody which binds to an epitope on type II collagen, or fragments thereof, which epitope only becomes detectable following cleavage of said collagen by collagenase.

34. The monoclonal antibody of claim 33, produced by the hybridoma cell line ATCC HB-12429.

35. A cell line producing a monoclonal antibody which binds to an epitope on type II collagen, or fragments thereof, which epitope only becomes detectable following cleavage of said collagen by collagenase.

36. The method according to claim 26, wherein said biological sample is articular cartilage.

37. The method according to claim 36, wherein said articular cartilage is in vivo.

* * * * *